US011772331B2

(12) United States Patent
Lucas

(10) Patent No.: US 11,772,331 B2
(45) Date of Patent: *Oct. 3, 2023

(54) SYSTEM AND METHOD FOR PRODUCING DENTAL SOLUTIONS INCORPORATING A GUIDANCE PACKAGE

(71) Applicant: Kelly Lucas, Wasilla, AK (US)

(72) Inventor: Kelly Lucas, Wasilla, AK (US)

(*) Notice: Subject to any disclaimer, the term of this patent is extended or adjusted under 35 U.S.C. 154(b) by 0 days.

This patent is subject to a terminal disclaimer.

(21) Appl. No.: 17/240,900

(22) Filed: Apr. 26, 2021

(65) Prior Publication Data

US 2021/0245444 A1 Aug. 12, 2021

Related U.S. Application Data

(63) Continuation of application No. 16/329,549, filed as application No. PCT/US2017/049545 on Aug. 31, 2017, now Pat. No. 10,987,872.

(Continued)

(51) Int. Cl.
*B29C 64/393* (2017.01)
*B33Y 50/02* (2015.01)
(Continued)

(52) U.S. Cl.
CPC .......... *B29C 64/393* (2017.08); *A61C 7/002* (2013.01); *A61C 11/00* (2013.01); *A61C 19/045* (2013.01);
(Continued)

(58) Field of Classification Search
CPC ....... B29C 64/393; A61C 7/002; A61C 11/00; A61C 19/045; A61C 19/05; A61C 1/084;
(Continued)

(56) References Cited

U.S. PATENT DOCUMENTS

2008/0096151 A1* 4/2008 Cinader, Jr. ............. A61C 7/12
433/24
2011/0276159 A1* 11/2011 Chun ................. A61C 13/0004
700/98
(Continued)

FOREIGN PATENT DOCUMENTS

CN 105982747 A * 10/2016
EP 2604220 A1 6/2013
(Continued)

OTHER PUBLICATIONS

Notice of Reasons for Refusal issued with corresponding Japanese Patent Application No. 2019-531605 dated Sep. 28, 2021 (including English Translation).

(Continued)

*Primary Examiner* — Thomas C Lee
*Assistant Examiner* — Michael Tang
(74) *Attorney, Agent, or Firm* — Troutman Pepper Hamilton Sanders LLP; Dustin B. Weeks; Brandon M. Reed

(57) ABSTRACT

A method of producing a retention piece having a guidance package configured to provide a desired movement profile including: obtaining data descriptive of mandibular and maxillary arches, an index position of the mandibular arch at a maximum closure position, and a temporomandibular joint of a recipient; specifying an appropriate guidance package based on the desired movement profile; positioning a retention piece comprising at least a portion of the specified guidance package about virtual representations of at least one of the mandibular and maxillary arches within a virtual articulator; modeling relative movement of the virtual representations of the mandibular and maxillary arches within the virtual articulator; and generating data that can be used by a computer aided machining (CAM) process to create at least one physical retention piece comprising the (Continued)

specified guidance package configured to provide the desired movement profile.

19 Claims, 57 Drawing Sheets

Related U.S. Application Data

(60) Provisional application No. 62/382,106, filed on Aug. 31, 2016.

(51) Int. Cl.
*G16H 50/50* (2018.01)
*A61C 19/05* (2006.01)
*G05B 19/4099* (2006.01)
*A61F 5/56* (2006.01)
*A61C 19/045* (2006.01)
*G16H 20/00* (2018.01)
*A61C 11/00* (2006.01)
*A61C 7/00* (2006.01)
*A61C 1/08* (2006.01)
*A61C 7/08* (2006.01)
*A61C 7/36* (2006.01)

(52) U.S. Cl.
CPC ............. *A61C 19/05* (2013.01); *A61F 5/566* (2013.01); *B33Y 50/02* (2014.12); *G05B 19/4099* (2013.01); *G16H 20/00* (2018.01); *G16H 50/50* (2018.01); *A61C 1/084* (2013.01); *A61C 7/08* (2013.01); *A61C 7/36* (2013.01); *A61F 2005/563* (2013.01); *G05B 2219/35134* (2013.01); *G05B 2219/49007* (2013.01)

(58) Field of Classification Search
CPC ... A61C 7/08; A61C 7/36; A61F 5/566; A61F 2005/563; B33Y 50/02; G05B 19/4099; G05B 2219/35134; G05B 2219/49007; G16H 20/00; G16H 50/50
See application file for complete search history.

(56) References Cited

U.S. PATENT DOCUMENTS

| | | | |
|---|---|---|---|
| 2012/0115107 A1* | 5/2012 | Adams | A61B 5/4542 |
| | | | 433/215 |
| 2013/0122448 A1 | 5/2013 | Kitching | |
| 2014/0060549 A1 | 3/2014 | Lucas | |
| 2014/0370465 A1* | 12/2014 | Lucas | A61C 5/007 |
| | | | 433/214 |
| 2017/0312064 A1* | 11/2017 | Jaisson | A61B 5/1079 |
| 2018/0304540 A1* | 10/2018 | Tobia | B29C 64/35 |

FOREIGN PATENT DOCUMENTS

| | | | | |
|---|---|---|---|---|
| JP | 2007037687 A | * | 2/2007 | |
| JP | 2007037687 A | | 2/2007 | |
| JP | 2014-133134 A | | 7/2014 | |
| JP | 2014133134 A | * | 7/2014 | ............. A61C 7/002 |

OTHER PUBLICATIONS

Extended European Search Report for European Patent Application No. 17847528.1 dated Feb. 7, 2020.
International Search Report and Written Opinion for PCT Application No. PCT/US17/49545 dated Nov. 16, 2017.

* cited by examiner

FRONT

SYSTEM AND METHOD FOR PRODUCING DENTAL SOLUTIONS INCORPORATING A GUIDANCE PACKAGE

CROSS-REFERENCE TO RELATED APPLICATIONS

This application is a continuation of U.S. patent application Ser. No. 16/329,549, filed 28 Feb. 2019, which is a U.S. National Stage Application of and claims the benefit pursuant to 35 U.S.C. § 371 of, International Patent Application No. PCT/US2017/049545, filed 31 Aug. 2017, which claims priority to U.S. Provisional Patent Application No. 62/382,106, filed 31 Aug. 2016, the entire contents and substance of which are incorporated herein by reference in their entirety as if fully set forth below.

TECHNICAL FIELD

The various embodiments of the present disclosure relate generally to systems and methods for producing oral retention pieces having guidance packages to provide a desired movement profile for the mandibular arch in relation to the maxillary arch.

BACKGROUND

Dentists are often faced with the problem of trying to change the movement of a patient's mandibular arch with respect to their maxillary arch. For example, a new index position of the mandibular arch to the maxillary arch may be established to solve a number of problems. A different movement profile to a different index position may be used to address different problems, such as bruxism, sleep apnea, and Temporomandibular Dysfunction (TMD). Also, a new movement profile to a new index position is often prescribed by dentists when optimizing, rehabilitating, reconstructing, or restoring the stomatognathic system to include the jaws and teeth.

For example, bruxism is an involuntary or habitual grinding of the teeth, typically during sleep, which undesirably causes many dental and medical problems. Bruxism has been known to cause myo-facial pain syndrome, damage to teeth, and damage to the temporomandibular joints (TMJs). Incorrect or inadequate treatment of bruxism can amplify its effects. Many types of night guards have been designed to help address the negative impacts of bruxism. Some night guards simply cover the teeth to prevent wear, while others aim to correct the centric relation (CR)/centric occlusion (CO) discrepancy to allow the TMJ to relax in its most anatomically appropriate and best stress bearing position (centric relation for most patients. Other night guards provide anterior guidance, which, among other benefits, significantly reduces the inappropriate muscle force associated with bruxism and guides the jaw to avoid posterior interferences. Generally speaking, night guards protect the teeth, address the CR/CO discrepancy, and provide anterior guidance, as failing to address all three aspects can often increase the severity of bruxism.

Traditionally, dental professionals have constructed customized night guards, which are typically attached to the maxillary and/or mandibular teeth, by hand. The customized night guard allows the dental professional to consider a patient's particular malocclusion and other factors to place the patient's jaw in centric relation or another predetermined index position (a new prescribed maximum closure position).

Another condition, obstructive sleep apnea is caused by an airway that is restricted. Often this condition can be treated with an oral appliance. Certain appliances may address this condition by changing the index (e.g., resting) position of the mandible in regard to the maxilla to a more protrusive position in a closing or closed position to keep the mandible anterior in relation to the maxilla to also therefore pull the tongue anteriorly to also therefore open the airway. For example, a sleep apnea appliance may change the position of the mandible to a prescribed protrusive orientation (new maximum closure position) by a prescribed route.

As another example, TMD (temporomandibular dysfunction), may be expressed in a number of ways that will cause pain and further damage for the patient if left untreated. Often this condition can be treated with an oral appliance. This appliance may preclude the mandible from movement that would put stress on the damaged area of one or both TMJs, or in general change the index position of the mandible to the maxilla and the movement profile to that new indexed position as part of a TMD treatment.

Another example circumstance would be optimizing, rehabilitating, reconstructing or restoring the stomatognathic system to include the jaws and teeth. Many patients suffer a major CO centric occlusion/CR centric relation discrepancy due to a malocclusion or other issue. In other words, the jaw position when the teeth or arches closed together may be incompatible with the patients' TMJs or may be in conflict with some other aspect of the stomatognathic system. When a dentist is in the process of a patient optimization, rehabilitation, reconstruction or restoration, it may be advantageous for the patient to change this problematic maximum intercuspation position (index position of the mandible to the maxilla in the maximum closure position) and the movement profile to that different position. This may involve modification of the maxillary and/or mandibular arch. The dentist may modify the tissue of the arch with the use of restorative, surgical and/or implant placement guides. The dentist may provide restorations that when the teeth or arches are closed together, this new position and the continuum of guidance to this different position is now compatible with the patient's TMJs (or to correct some other circumstance of incompatibility in the stomatognathic system).

These example appliances, restorations, and restorative/surgical/implant placement guides may be effective, and may guide the patient's mandible to a new maximum closure position by a prescribed route. However, in the related art, it typically requires substantial time and effort to create and modify the appliances, restorations and surgical/restorative/implant placement guides for a particular patient. Bruxism appliances, TMD appliances and sleep apnea appliances in the related art may also be of limited use for patients with missing or periodontally weakened teeth or specific malocclusions, and only provide limited anterior guidance.

The inventor of the embodiments described herein has invented numerous guidance packages and systems for making and using guidance packages to provide a number of desired movement profiles, which are described in U.S. patent application Ser. Nos. 13/573,283, 13/774,033, 13/774,920, 13/918,754, 14/083,467, and 14/748,805, which are incorporated herein by reference in their entireties as if fully set forth below. However, many related art solutions suffer from some of the issues discussed above in that it can be difficult to customize a guidance package to a particular patient in an efficient manner.

Accordingly, there is a need for improved systems and methods to address the above mentioned deficiencies. Embodiments of the present disclosure are directed to these and other considerations.

SUMMARY

The present disclosure relates to systems and methods for producing retention pieces having a guidance package to correct a movement profile of a patient. The movement profile may be corrected to appropriately guide the patient's mandible to a new index position (e.g., a rest, or therapeutic assigned position) of the mandible in relation to the maxilla (e.g., a new maximum closure position).

According to an example embodiment, there is provided a method of producing a guidance-equipped solution configured to provide a desired movement profile for the mandibular and maxillary arches of a recipient relative to each other, the method including: obtaining data descriptive of the mandibular and maxillary arches, an index position of the mandibular arch with respect to the maxillary arch, and one or more boundaries of a three-dimensional region; specifying an appropriate virtual guidance package based on the desired movement profile, the virtual guidance package associated with a movement profile; positioning the specified virtual guidance package in virtual space; parameterizing the positioned guidance package across the three-dimensional region to create at least one virtual guidance equipped solution; and generating data that can be used to create at least one physical guidance-equipped solution configured to provide the movement profile associated with the specified virtual guidance package for the mandibular and maxillary arches relative to each other.

The method may further include generating a virtual model of the maxillary and mandibular arches, and the specified virtual guidance package may be positioned in virtual space within the virtual model.

The method may further include customizing the specified virtual guidance package by adjusting at least one of a size, position, and orientation of the specified virtual guidance package within the virtual space, creating a customized movement profile, and the at least one physical guidance-equipped solution may be configured to provide the customized movement profile for the mandibular and maxillary arches relative to each other.

The boundary of the three-dimensional region may include tissue surfaces of at least one of the mandibular arch and the maxillary arch.

The boundary of the three-dimensional region may include a region embedded within surfaces of at least one of the mandibular arch and the maxillary arch.

Parameterizing the positioned guidance package across the three-dimensional region may provide a plurality of virtual guidance equipped solutions formed across a spectrum.

The plurality of virtual guidance equipped solutions may include a plurality of synergistically shaped guidance solutions each configured to provide the movement profile associated with the specified virtual guidance package.

The parameterizing may include forming a series of virtual guidance equipped solutions designed to progressively or correct damage of the recipient.

The at least one virtual guidance equipped solution may include at least one of a surgical guide, a restorative guide, and an implant placement guide for at least one of the mandibular arch and the maxillary arch.

The surface of the three-dimensional region may define a maximum possible depth of the surgical guide, restorative guide, and implant placement guide.

The physical guidance-equipped solution may include a therapeutic device.

The therapeutic device may include a clear-aligner type orthodontic appliance.

The method may further include selecting a virtual guidance equipped solution from the at least one virtual guidance equipped solution based on a desired response from a neuromuscular system of the recipient.

The method may further include selecting a virtual guidance equipped solution from the at least one virtual guidance equipped solution based on appropriate curves of occlusion for the recipient.

The at least one virtual guidance equipped solution may include a retentive piece for one of the mandibular and maxillary arches comprising surfaces configured to interact with tissue of the other one of the mandibular and maxillary arches to provide the movement profile associated with the specified virtual guidance package for the mandibular and maxillary arches relative to each other.

The method may further include generating the data descriptive of the one or more boundaries of the three-dimensional region based on the data descriptive of the mandibular and maxillary arches.

The method may further include generating a virtual model of the maxillary and mandibular arches, and the boundary of the three dimensional space may be embedded within surfaces of at least one of the virtual mandibular arch and the maxillary arch.

The method may further include identifying a desired form of the at least one virtual guidance equipped solution, and the created at least one virtual guidance equipped solution may conform to the desired form.

The method may further include generating the data descriptive of the one or more boundaries of the three-dimensional region based on the data descriptive of the mandibular and maxillary arches and the desired form of the at least one virtual guidance equipped solution.

According to some example embodiments, there is provided a computer readable apparatus may have stored thereon computer program code for performing one or more of the methods described herein.

According to an example embodiment, there is provided a method of producing a retention piece having a guidance package configured to provide a desired movement profile for the mandibular and maxillary arches of a recipient relative to each other, the method including: obtaining data descriptive of the mandibular and maxillary arches, an index position of the mandibular arch with respect to the maxillary arch at a predetermined maximum closure position, and at least one temporomandibular joint of the recipient; specifying an appropriate guidance package based on the desired movement profile for the mandibular and maxillary arches relative to each other; positioning a virtual representation of a retention piece comprising at least a portion of the specified guidance package about virtual representations of at least one of the mandibular and maxillary arches within a virtual articulator; modeling, with the virtual representation of the retention piece positioned about the at least one of the mandibular and maxillary arches, relative movement of the virtual representations of the mandibular and maxillary arches within the virtual articulator to determine whether the specified guidance package provides the desired movement profile, the relative movement resulting from the guidance provided by the virtual representation of the specified guidance package; and generating data that can be used by a computer aided machining (CAM) process to create at least one physical retention piece comprising the specified guidance package configured to provide the desired movement profile.

The appropriate guidance package may be specified from a plurality of guidance packages, each preprogrammed to provide a different movement profile.

The data descriptive of the at least one temporomandibular joint may be specific to a temporomandibular joint of the recipient.

The method may further include using a three-dimensional printer to create the at least one physical retention piece based on the generated data.

The method may further include selecting a transverse, sagittal and frontal size for the specified appropriate guidance package based on at least a portion of the data.

The retention piece may include at least one from among of a denture or a partial denture comprising at least a portion of the guidance package, a crown comprising at least a portion of the guidance package, and a bridge comprising at least a portion of the guidance package.

The retention piece may include a guidance component including a concave portion surrounded by a bumper-shaped perimeter dimensioned to prevent lips of the recipient being pinched by the guidance component when the recipient closes his mouth.

The method may further include scaling the specified guidance package, based on at least a part of the obtained data, and the virtual representation of the retention piece may include the scaled specified guidance package.

The method may further include: positioning a virtual representation of another retention piece comprising at least another portion of the specified guidance package about the virtual representations of the other of the mandibular and maxillary arches within the virtual articulator; and modeling, with the virtual representation of the retention piece and another retention piece positioned about the mandibular and maxillary arches, relative movement of the virtual representations of the mandibular and maxillary arches within the virtual articulator to determine whether the specified guidance package provides the desired movement profile, the relative movement resulting from the guidance provided by the virtual representation of the specified guidance package.

The at least one physical retention piece may be configured to provide the desired movement profile based on interference with at least a portion of tissue in a mouth of the patient.

The method may further include creating the at least one physical retention piece utilizing at least one of additive and reductive CAM technologies.

The data that can be used by a CAM process to create at least one physical retention piece may include data that can be used to create a plurality of physical retention pieces for progressively treating damage.

The at least one retentive piece may include a therapeutic device.

The therapeutic device may include a clear-aligner type orthodontic appliance.

According to some embodiments, there is provided a method of producing a retention piece having a guidance package configured to provide a desired movement profile for a recipient. The method may include obtaining data descriptive of: (1) the recipient's mandibular and maxillary arches, (2) an index position of the mandibular arch with respect to the maxillary arch of the recipient at a predetermined maximum closure position, and (3) at least one temporomandibular joint. The method can further include modeling movement of virtual representations of the mandibular arch with respect to the maxillary arch of the recipient within a virtual articulator based at least in part on at least a portion of the data, and specifying an appropriate guidance package based at least on the data and a desired movement profile for the mandibular arch relative to the maxillary arch.

The method may further include generating one or more virtual points based on one or more of the index position and a position, orientation, or position of one or more of the retentive pieces. A virtual guidance package may be positioned in virtual space based on the one or more virtual points. In some cases, the one or more virtual points indicate not only position, but also orientation of the virtual guidance package relative to one or more of the retentive pieces (e.g., virtual retentive pieces). The guidance package may include a virtual maxillary guidance component and a virtual mandibular guidance component. After positioning the guidance package in virtual space, the virtual maxillary guidance component may be connected to the virtual maxillary retentive piece to form a first part of a virtual AGP equipped splint. Similarly, the virtual mandibular guidance component may be connected to the virtual mandibular retentive piece to form a second part of the virtual guidance package equipped appliance.

The method may further include positioning a virtual representation of at least one retention piece including the specified guidance package about the virtual representations of the mandibular and maxillary arches within a virtual articulator at a position achieving a desired movement profile. The method may further include modeling relative movement of the virtual representations of the mandibular and maxillary arches within a virtual articulator to ensure the desired movement profile is achieved, the movement resulting from the guidance provided by the virtual or mathematical representation of the specified guidance package. The method can further include customizing the movement profile using patient specific data.

In some embodiments, the guidance package derived appliance may be an appliance that provides three-dimensional control, guidance and limits to the front end of the mandible. The guidance package may be indexed within a wide range in the frontal, sagittal and transverse planes in the retentive piece system to produce a superior, seamless guidance package derived appliance for the bruxism patient, a sophisticated Temporomandibular Disorders (TMDs) guidance package derived appliance produced with specific jaw repositioning and guidance limitations as prescribed by a dental professional, or a mandibular protrusive repositioning sleep apnea appliance. The guidance package derived appliance may have a unique ability to provide anterior guidance in the retentive piece system within a broad transverse, frontal and sagittal range to include anterior to the teeth therefore enhancing the mechanical advantage over the muscles of mastication. The guidance package derived appliance can provide three-dimensional anterior guidance to the jaw and the elimination of posterior interferences (e.g., collisions) without any limitations due to the conditions, malocclusion, presence, or absence of the teeth (e.g., anterior teeth). The guidance package may be indexed and then attached to retentive pieces within the retentive piece system, not directly to the teeth or arch. The guidance package derived appliance may provide this guidance to the jaw with a minimal vertical dimension penalty when the jaw is in centric relation (CR) because the guidance package may be placed anterior to and independent of teeth. The guidance package derived appliance may provide unprecedented control of the anterior guidance and limitations of the jaw to the operator because the selection (or design) of guidance by the dental professional is three dimensional and may be independent of teeth.

In some embodiments, the disclosed guidance package may reduce patient time required to initially receive a guidance package derived appliance or to obtain a new guidance package derived appliance when the previous one becomes worn out or damaged. Certain embodiments of the disclosed methods may minimize the time and effort of both the patient and the dentist to get a new guidance package derived appliance specially designed for the patient. Using a virtual articulator and CAD (Computer Aided Design)-CAM (Computer Aided Manufacturing) technology combined with a guidance package, a dental professional can provide, to a patient, a guidance package derived appliance that can be produced from an unprecedented wide range of three-dimensional guidance and limit parameters. Digital records from the patient can be analyzed and then, taking advantage of the flexibility of the guidance package system, a plethora of design possibilities regarding guidance and limits for the mandible dependent upon the dental professional's goals for that patient can be realized. When combined with data from, for example, a Jaw Motion Analyzer, these appliances may be highly accurate to a particular patient. According to some embodiments, there is provided a method for producing, as non-limiting examples, a superior, seamless guidance package derived bruxism appliance, a sophisticated TMD guidance package derived appliance produced with specific jaw repositioning and guidance limitations as prescribed by a dental professional, or a mandibular protrusive repositioning sleep apnea appliance.

According to some embodiments, there is provided a method of automatically producing or reproducing a customized guidance package derived appliance for a patient with or without a severe malocclusion. The method may combine Virtual Articulation technology, Jaw Motion Analyzer technology and/or CAD-CAM methods with the unique attributes of the guidance package system and retentive piece technology. The method may enable a patient with or without a severe malocclusion and bruxism to receive a customized guidance package derived bruxism appliance, a sophisticated customized guidance package derived TMD appliance produced with specific jaw repositioning and guidance limitations, or a guidance package derived mandibular protrusive repositioning sleep apnea appliance automatically without visiting the dental professional repeatedly.

The disclosed methods can be applied to a wide range of stock guidance packages, and/or stock guidance packages that are subsequently modified, and/or a custom designed guidance package for a specific patient and a specific purpose. The guidance package could be any of a wide selection of sizes, shapes or styles to address a very wide range of problems and/or malocclusions. The maxillary component and/or the mandibular component of the guidance package can be designed or modified to any of a wide selection of shape, size, or style either individually or as a group to achieve the effect the operator desires. For instance, a TMD therapist will have available an unprecedented range of options regarding both limits and guidance to the mandible. In contrast to other systems, the guidance package system can provide a wide range of three-dimensional anterior guidance, and limits to the mandible and may be independent of the condition, position, presence or absence of teeth. Also, the position of the guidance package (and therefore guidance and limits of the mandible) within the guidance package retentive piece system can be controlled to maximize or minimize different properties to include increase or decrease of the mechanical advantage over the muscles of mastication of the guidance package derived appliance. Considering the unprecedented three-dimensional selection and design potential of the guidance package system, and the extreme flexibility regarding the position of the guidance package within the guidance package retentive piece system, the CAD-CAM guidance package derived appliance, the CAD-CAM TMD guidance package derived appliance, and CAD-CAM sleep apnea guidance package derived appliance are far superior to existing night guards, TMD appliance systems, or sleep apnea systems.

The method can further include a parameterization of the customized movement profile whose boundary is an envelope region and selection of different synergistically shaped guidance packages. The method can further include generating data that can be used by a computer aided manufacturing ("CAM") process to create at least one physical retention piece including the specified guidance package to achieve the desired movement and stop profile.

In some embodiments of the present disclosure, the method can further include using additive technologies such as the three-dimensional printer and/or reductive processes such as CNC routing, laser cutting, or water jet cutting to create the at least one physical retention piece.

In some embodiments of the present disclosure, the method can further include selecting a transverse, sagittal and frontal size for the specified appropriate guidance package based at least in part on at least a portion of the data.

According to some embodiments, there is provided a system for producing a retention piece having a guidance package to provide a desired movement profile for a recipient. In an example embodiment of the present disclosure, the system can include at least one processor and at least one memory. The at least one memory can include instructions that, when executed by the processor, cause the system to perform the various steps of the one or more methods described above. For example, the instructions may, when executed by the processor, control the system to obtain data descriptive of (1) the recipient's mandibular and maxillary arches, (2) an index position of the mandibular arch with respect to the maxillary arch of the recipient at a predetermined maximum closure position, and (3) at least one temporomandibular joint.

The at least one memory can further include instructions that, when executed by the processor, cause the system to allow an operator of the system to model movement of virtual representations of the mandibular arch with respect to the maxillary arch of the recipient within a virtual articulator based at least in part on at least a portion of the data. The at least one memory can further include instructions that, when executed by the processor, cause the system to allow an operator of the system to specify an appropriate guidance package based at least on the data and a desired movement profile for the mandibular and maxillary arches relative to each other.

In some cases, the instructions may, when executed by the processor, instruct the system to identify one or more virtual points to position a virtual specified guidance package in virtual space in relation to a virtual representation of one or more retentive pieces. In some cases, the one or more virtual points may identify both a location on the one or more retentive pieces and a relative orientation of the specified guidance package. In some cases, the one or more virtual points may be specified or modified by an operator of the system (e.g., a dental professional). The instructions may provide a user interface for the specification or modification of the virtual points by the operator.

The at least one memory can further include instructions that, when executed by the processor, cause the system to allow an operator of the system to position a virtual representation of at least one retention piece including the specified guidance package about the virtual representations of the mandibular and maxillary arches within a virtual articulator at a position achieving a desired movement profile.

The at least one memory can further include instructions that, when executed by the processor, cause the system to allow an operator of the system to model relative movement of the virtual representations of the mandibular and maxillary arches within a virtual articulator to ensure the desired movement profile is achieved, the movement resulting from the guidance provided by the virtual and/or mathematical representation of the specified guidance package.

The at least one memory can further include instructions that, when executed by the processor, cause the system to allow an operator of the system to customize the movement profile using patient specific data.

The at least one memory can further include instructions that, when executed by the processor, cause the system to allow an operator of the system to conduct a parameterization of the customized movement profile within a bounded envelope region (a virtual three-dimensional (3D) region) and selection of different synergistically shaped guidance packages. In some cases, the virtual 3D region may include space for generation of one or more retentive pieces, the guidance package, and all other functions of the guidance package system, and may be referred to as a global 3D region.

The at least one memory can further include instructions that, when executed by the processor, cause the system to generate data that can be used by a CAM process to create at least one physical retention piece including the specified guidance package to achieve the desired movement profile.

In some embodiments of the present disclosure, the memory can further include instructions that, when executed by the processor, cause the system to use additive and/or reductive CAM technologies to include the 3D printer to create the at least one physical retention piece.

In some embodiments of the present disclosure, the memory can further include instructions that, when executed by the processor, cause the system to allow an operator of the system to select a transverse, sagittal and frontal size for the specified appropriate guidance package based at least in part on at least a portion of the data.

In some embodiments of the present disclosure, the appropriate guidance package can be specified from a plurality of guidance packages, each preprogrammed to provide a different movement and stop profile.

In some embodiments of the present disclosure, the data descriptive of the at least one temporomandibular joint can be specific to a temporomandibular joint of the recipient.

In some embodiments of the present disclosure, the data descriptive of the at least one temporomandibular joint can be descriptive of a generic temporomandibular joint.

In some embodiments of the present disclosure, the retention piece can include one of a denture or a partial denture including at least a portion of the guidance package.

In some embodiments of the present disclosure, the retention piece can include a crown including at least a portion of the guidance package.

In some embodiments of the present disclosure, the retention piece includes a bridge including at least a portion of the guidance package.

In some embodiments of the present disclosure, the guidance package can include at least one protrusion extending away from the retention piece, the protrusion having a geometrical shape that causes the mandibular arch to move in the desired movement profile when the protrusion mechanically contacts a surface of the other of the mandibular and maxillary arches or another retention piece in contact therewith. The guidance package or movement and stop profile may be a virtual representation and/or a mathematical object.

In some embodiments of the present disclosure, the retention piece includes prosthetics that may include one or more of a crown, bridge, removable partial denture ("RPD"), denture, other fixed or removable prosthetics, and combinations thereof.

In some embodiments of the present disclosure, the retentive piece includes an appliance that may be smoothly flowing plastic or other material that may include one or more of a bruxism appliance, sleep apnea appliance, TMD appliance, or other therapeutic, restorative, or protective appliance. In some embodiments of the present disclosure, the guidance package solution to include a defined space (envelope region) may enable creation of surgical guides, restorative guides, and implant placement guides. In some embodiments, a surface of the retentive piece (for example, a device to define an envelope region) located within the tissue for defining an envelope region serves as the base of both that parameterization but also the limit of potential modification of tissue. In other words, in some embodiments, the envelope region not only defines the defined space for parametrical consideration of a guidance package solution, but also may dictate to what depth surgical, restorative and implant placement guides may be used to modify tissue.

These and other aspects of the present disclosure are described in greater detail in the Detailed Description with reference to the accompanying figures. Other aspects and features of example embodiments will become apparent to those of ordinary skill in the art upon reviewing the following description of specific, example embodiments of the present disclosure in concert with the figures. While features of the present disclosure may be discussed relative to certain embodiments and figures, embodiments of the present disclosure can include one or more of the features discussed herein. Further, while one or more embodiments may be discussed as having certain advantageous features, one or more of such features may also be used with the various embodiments. In similar fashion, while example embodiments may be discussed below as device, system, or method embodiments, it is to be understood that such example embodiments can be implemented in various devices, systems, and methods of the present disclosure.

BRIEF DESCRIPTION OF THE DRAWINGS

The following Detailed Description is better understood when read in conjunction with the appended drawings. For the purposes of illustration, there is shown in the drawings example embodiments, but the subject matter is not limited to the specific elements and instrumentalities disclosed.

DETAILED DESCRIPTION

Figure 1:
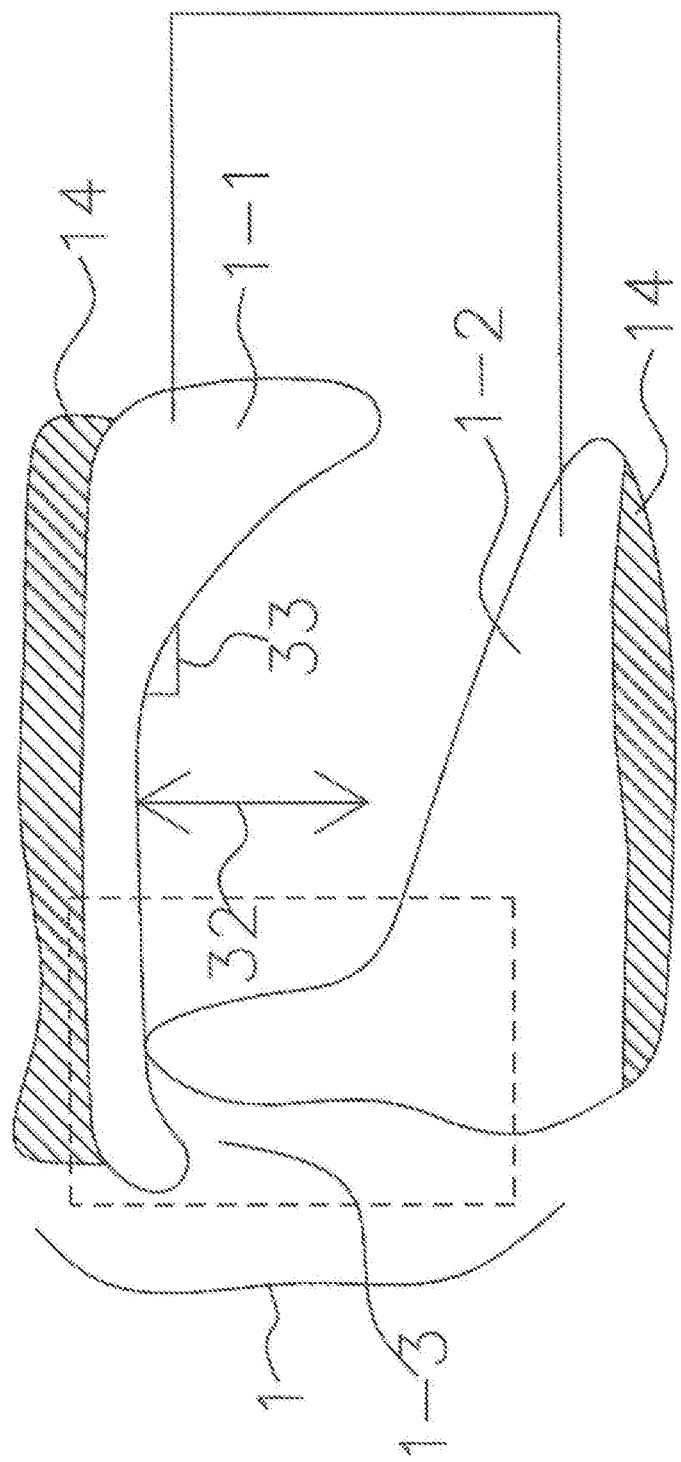
FIG. 1 is a side view of a simple guidance package for the amelioration of the damage and pain caused by bruxism in accordance with an example embodiment.

To facilitate an understanding of the principles and features of the present disclosure, various illustrative embodiments are described below. To simplify and clarify explanation, the example embodiments are described below as applied to guidance packages and oral retention pieces including guidance packages for obtaining a desired movement profile for a recipient's, e.g., a patient's, mandibular arch in relation to the maxillary arch. In some cases, the guidance packages or oral retention pieces may be used for, as non-limiting examples, treating a patient with bruxism, TMD, sleep apnea, or treating a patient that needs full mouth reconstruction or optimization, due to dental caries, periodontal disease, edentulism, or other medical and/or dental issues.

The components, steps, and materials described hereinafter as making up various elements of example embodiments are intended to be illustrative and not restrictive. Many suitable components, steps, and materials that would perform the same or similar functions as the components, steps, and materials described herein are intended to be embraced within the scope of the invention. Such other components, steps, and materials not described herein can include, but are not limited to, similar components or steps that are developed after development of the invention.

As discussed above, medical practitioners, such as dentists, have routinely used many devices and prosthetics in an attempt to obtain a desired movement and stop profile, perhaps to a new index position of the mandible in relation to the maxilla, for a patient mandible in relation to the maxilla, such as to correct for bruxism, sleep apnea, TMD, patient reconstruction, rehabilitation, restoration or optimization. However, conventional systems are inefficient in customizing these devices for particular patients.

Accordingly, some example embodiments make the use of virtual articulators that allow devices to be designed and customized in a virtual environment prior to the creation of the physical device to be used by a patient. For example, various embodiments provide systems and methods for employing a virtual articulator to design and produce retention pieces having a guidance package to provide a desired movement profile for a patient, often to a new index position of the mandible relative to the maxilla. Various embodiments can use different virtual articulators known in the art, such as Exocad and 3Shape, or articulators later developed.

According to an example embodiment, there is provided a method for producing one or more retention pieces having a guidance package to provide a desired movement profile for a recipient, such as a patient. The method includes obtaining data descriptive of (1) mandibular and maxillary arches of a patient, (2) an index position of the mandibular arch with respect to the maxillary arch of the patient at a predetermined (prescribed) maximum closure position, (3) at least one temporomandibular joint, and (4) range of motion data for the mandible of the patient. The data descriptive of the mandibular and maxillary arches can be obtained a number of ways known in the art. In some embodiments, the data can result from imaging of maxillary and mandibular impressions or models from a patient. In some embodiments, the data can result from direct scanning systems. Examples of direct scanning systems include, but are not limited to, Planmeca/E4D Planscan, 3shape Trios, and Cadent Itero. In some embodiments, the data can result from imaging, e.g., x-ray, of a patient's mandible and maxilla. In some embodiments, the data can result from systems that combine 3D x-ray with scanning, including, but not limited to, the Planmeca system. In some embodiments of the present disclosure, the data descriptive of the mandibular and maxillary arches can be used to create a visual representation of the patient's mandibular and maxillary arches within a virtual articulator.

The data descriptive of an index position of the mandibular arch with respect to the maxillary arch of the patient at a predetermined (prescribed) maximum closure position can also be obtained in a number of ways. In some embodiments, the data can result from measurements taken by an examiner, e.g., a dentist, when examining a patient. In some embodiments, the dentist may use other means to determine the appropriate index position such as 3D radiography, the combination (fusion) of 3D radiography and scanning (Planmeca), and a Jaw Motion Analyzer.

The data descriptive of the at least one temporomandibular joint (TMJ), and mandibular range of motion data can also be obtained in many different ways and can include many different pieces of information. In some embodiments, the TMJ and range of motion data can be unique to a particular patient. In some embodiments, the TMJ and mandibular range of motion data can be generic TMJ and range of motion data to a class of people, e.g., taken based on average measurements from a number of people. In some embodiments, the TMJ and mandibular range of motion data can be indicative of how the TMJ hinges, slides, and/or rotates and further is indicative of the movement and envelope of function of the mandible. This data may be collected by a Jaw Motion Analyzer such as Zebris or Planmeca 4D, or by other methods.

In certain embodiments, the method further includes modeling movement of virtual representations of the mandibular arch in relation to the maxillary arch of the patient within a virtual articulator based at least in part on at least a portion of the data. As discussed above, the data can be used to create virtual representations of the mandibular and maxillary arches of a patient. Additionally, based on the TMJ data and index data, the virtual articulator can be used to model how a particular patient's mandible moves relative to their maxilla, which can be helpful to visualize locations where grinding of teeth occur in a virtual environment. By modeling the movement, it can be determined how that movement might be altered to obtain a desired effect, i.e., a desired movement profile.

In some embodiments, the method further includes specifying an appropriate guidance package based at least on a desired movement profile for the mandible relative to the maxilla. The guidance package (canonical movement and stop profile) can be a virtual representation and/or a mathematical object. In some embodiments, the appropriate guidance package is specified based on at least a portion of the data (or information indicated/represented by the data) and a desired movement profile. Various embodiments of the present disclosure can make use of many different guidance packages based on many different desired movement profiles for a patient, some of which are discussed below.

Accordingly, in some embodiments, the appropriate guidance package can be specified from a plurality of guidance packages, each preprogrammed to provide a different movement profile. A preprogrammed guidance package may be "preprogrammed" in that the relative movement when the guidance components are in contact may be determined beforehand. For example, a guidance package may include a mandibular guidance component and a maxillary guidance component configured to mate with one another. When the guidance components are positioned on respective retentive pieces in a correct orientation, the guidance components may appropriately guide in the "preprogrammed" way a movement of the retentive pieces (and therefore the mandible) as the guidance components come together and/or function together in a vertical, protrusive, and/or lateral movement of the retentive pieces (therefore the mandible relative to the maxilla) when the guidance components are in contact.

As non-limiting examples, one guidance package (or class of guidance packages, e.g., canine guidance and/or a group function guidance) may be useful for obtaining a desired movement profile for a patient suffering from bruxism while a different guidance package (or a different class of guidance packages, e.g., a bilateral anterior repositioning guidance package) may be useful for obtaining a desired movement profile for a patient suffering from sleep apnea. In the case of TMJ dysfunction ("TMD"), within the range of motion of the plurality of the TMJs, there might be preexisting damage or disease to one or both of the TMJs. A guidance package (e.g., canine guidance package, group function guidance package, asymmetric guidance package, bilateral anterior repositioning guidance package, or a asymmetric protrusive guidance package) could arrange guidance in many therapeutic strategies, for example, to avoid the area of damage or to provide gradual step therapy of the damaged area by a sequence of TMD appropriate guidance package derived therapeutic appliances. In the case of a patient rehabilitation, an ideal movement guidance package (e.g., a canine guidance package or a group function guidance package) may be useful to aid in the patient surgical, restorative, and implant placement management (by providing surgical, implant placement, and/or restorative guide[s]), and also to design and produce a solution (e.g., restoration or appliance) for reconstruction, rehabilitation, restoration, or optimization. Accordingly, the present disclosure allows for a user to specify an appropriate guidance package, e.g., a canine guidance package, to be used for a particular patient to achieve the desired movement and stop profile for that patient.

In some embodiments of the present disclosure, the method further includes selecting one or more virtual points to facilitate placement and orientation of the guidance package in virtual space inside the virtual articulator. In some implementations, the one or more virtual points may correspond to a position and orientation of the guidance package with regards to mandibular and maxillary retentive pieces.

In some embodiments, the method further includes positioning a virtual representation of at least one retention piece including the specified guidance package about the virtual representations of the mandibular and maxillary arches within the virtual articulator at a position specified to achieve the desired movement profile. For example, if a user specifies a guidance package to correct for bruxism, the user could use a virtual articulator to place a virtual representation of one or more retention pieces around the virtual representations of the mandibular and maxillary arches. The one or more retention pieces may include a mandibular retention piece for interfacing with the mandibular arch (or a portion thereof) of a user and a maxillary retention piece for interfacing with the maxillary arch (or a portion thereof) of the user. Each of the one or more retention pieces may include at least a portion of the specified guidance package at a specified location (e.g., at a virtual point) about the mandibular and/or maxillary arches of the user to achieve the desired movement profile that would ameliorate the negative effects of the user grinding his or her teeth.

For example, a mandibular retention piece can include a portion of a guidance package defined by a convex protrusion, and a maxillary retention piece can include a portion of the guidance package defined by a concave indention positioned to interface with the convex protrusion.

The one or more retention pieces (or the location of the guidance package on the one or more retention pieces) can be positioned at many different locations depending at least in part on the desired movement profile (and may also depend at least in part on the nature of the mandibular and/or maxillary arches). For example, a retentive piece on a given arch may involve only space on the guidance side of the retentive piece or may involve tissue that may or may not be modified on the guidance side of the retentive piece. The guidance package including the guidance and stops can be positioned at many different locations on the retentive pieces. For example, the guidance package (e.g., the preset guidance package, the customized with patient data guidance package, a parameterized guidance package, or the various components of guidance and stops that make up the guidance package) could be positioned at an anterior side of the arches, at a lateral side of the arches, or at locations between the arches, i.e., where the mandibular and maxillary arches interface and contact each other.

In some embodiments, the method can further include selecting a transverse, sagittal and/or frontal size for the specified guidance package based at least in part on at least a portion of the data. For example, based on the data that allows the virtual representation of mandibular and maxillary arches to be created, a user can determine the appropriate sizing of the guidance package necessary to achieve the desired movement profile.

In some embodiments, the method can further include modeling relative movement of the virtual representations of the mandibular and maxillary arches within a virtual articulator to ensure the desired movement profile is achieved, the relative movement resulting from the guidance provided by the virtual and/or mathematical representation of the specified guidance package. This can allow the user to verify that the specified guidance package, selected location, size, and/or modification of the guidance package will provide the desired movement profile for the patient when a guidance solution is implemented.

In some embodiments, after modeling the relative movement of the arches the user may determine that additional adjustments should be made, for example, as to which guidance package should be specified, the location at which that guidance package should be placed, the size of the specified guidance package, and/or a modification of the guidance package. The user can then make any changes using the virtual articulator and model the relative movement that results from those adjustments. This process can be repeated until the user, e.g., dentist, is satisfied with the movement profile produced by the guidance package.

In some embodiments, the method can further include a parameterization of the retentive piece(s) and/or by parameterization of the customized movement profile whose boundary is an envelope region (limited or global 3D space) and selection of different synergistically shaped guidance packages.

In some embodiments, the method can further include generating data that can be used for CAM to create one or more physical retention pieces containing the specified guidance package to achieve the desired movement profile. In certain embodiments, the method further includes using CAM to create the physical retention piece(s). Various example embodiments of the present disclosure allow the data generated to be stored locally such that the user can use a local CAM system to create one or more retention pieces for the patient. Additionally, various example embodiments may allow the generated data to be sent to a remote location for the physical retention piece(s) to be printed.

Various embodiments of the present disclosure can make use of many different retention pieces which can include the guidance packages used to provide the desired movement. For example, in some embodiments, the retention piece(s) can take the form of one or more trays to interface with the mandibular and maxillary arches of the patient. In some embodiments, the retention piece includes a denture or a partial denture including all or a subset of the guidance package. In some embodiments, the retention piece includes a crown including a subset of the guidance package. In some embodiments of the present disclosure, the retention piece includes a bridge including all or a subset of the guidance package. In some embodiments of the present disclosure, the retention piece includes other fixed or removable prosthetic components including all or a subset of the guidance package. In some embodiments of the present disclosure, the retention piece includes a bruxism appliance, a sleep apnea appliance, a TMD appliance, or other therapeutic, restorative, or protective appliance including all or a subset of the guidance package.

Various embodiments of the present disclosure can also make use of many different guidance packages, including, but not limited to those guidance packages described in U.S. patent application Ser. Nos. 13/573,283, 13/774,033, 13/774,920, 13/918,754, 14/083,467, and 14/748,805, as would be understood by one of ordinary skill.

In an example embodiment of the present disclosure, the guidance package includes at least one protrusion extending away from the retention piece(s), the protrusion having a geometrical shape that causes the mandibular arch relative to the maxillary arch to move in the desired movement profile when the protrusion mechanically contacts a surface of the other of the mandibular and maxillary arches (or a surface of the guidance package interfacing with the other of the mandibular and maxillary arches). In some implementations, the guidance package may be a virtual representation and/or a mathematical object.

In addition to methods, the present disclosure also provides systems for producing a retention piece or pieces having a guidance package to correct a movement profile of a patient. In an example embodiment of the present disclosure, the system includes at least one processor and at least one memory. In accordance with various embodiments of the present disclosure, the at least one memory can store instructions that, when executed by the processor, cause the system to perform and/or allow a user to perform one or more of the various method steps discussed above.

For example, in some embodiments of the present disclosure, the memory includes instructions that, when executed by the processor, cause the system to: obtain data descriptive of (1) mandibular and maxillary arches of a patient, (2) an index position of the mandibular arch with respect to the maxillary arch of the patient at a predetermined (prescribed) maximum closure position, and (3) the TMJs; enable modeling of movement of virtual representations of the maxillary and mandibular arches of the patient on a virtual articulator based at least in part on at least a portion of the data (e.g., by an operator); provide selection of a guidance package based at least on a portion of the data and a desired movement profile for the mandibular arch relative to the maxillary arch; allow an operator to customize the movement profile (e.g., with patient specific, average, generic, or other data); allow an operator to determine one or more virtual points for placement and orientation of retentive pieces and the specified guidance package; allow an operator of the system to position a virtual representation of the retention pieces including the specified or customized guidance package about the virtual representations of the mandibular and maxillary arches on the virtual articulator at a position specified to achieve the desired movement profile; allow an operator of the system to model determined movement of the virtual representations of the maxillary and mandibular arches on the virtual articulator to ensure the desired movement profile is achieved, the determined movement resulting from guidance provided by the virtual representation of the specified and customized guidance package; and generate data that can be used in CAM to create a physical retention piece or physical retentive pieces containing both the parameterized retentive piece(s) and the sized, indexed, adjusted, attached and parameterized respective components of the specified guidance package to achieve the desired movement profile. In some cases, the instructions, when executed by the processor, may further cause the system to parameterize the retentive piece(s)

and/or the movement profile specification with a boundary of a global envelope region (3D region) or multiple 3D regions and different synergistically shaped guidance packages.

In some embodiments of the present disclosure, the memory further includes instructions that, when executed by the processor, cause the system to use CAM to create the physical retention piece.

In some embodiments of the present disclosure, the memory further includes instructions that, when executed by the processor, cause the system to allow an operator of the system to select a transverse, sagittal and/or frontal size for the specified guidance package based at least in part on at least a portion of the data.

In some embodiments, it may be important to understand the shape of the volume of space between the mandibular and maxillary arches of a particular individual (e.g., patient). The combination of hinge and sliding motions makes the TMJ arguably among the more complex joints in the body. For a particular patient, the plurality of movement of both TMJs completely defines the range of motion of a mandible, until the range of motion is influenced by the interferences and guidance of teeth or prosthetics or appliances, which occurs as the mandible closes and contact is made between the opposing arches. As the mandible closes, within the range of motion of the TMJs, the first contact is made between the mandibular arch and the maxillary arch. From first contact until maximum closure are pathways that are defined by the interferences and guidance of both arches (e.g., teeth, other tissue, existing prosthetics, and/or appliances of the patient).

For many reasons in dentistry, medicine, and elsewhere it is desirable to affect change in providing a different maximum closure position of the mandible in relation to the maxilla and to provide prescribed pathways (a therapeutic, corrective, preventive, or protective movement profile) to move the mandible to that prescribed position. Some examples of these could include bruxism appliances, sleep apnea appliances, and TMD appliances. Other examples include a patient optimizing, rehabilitating, reconstructing or restoring by establishing a position of maximum closure and a guidance profile to that position as the mandible closes through selection by a clinician for that patients' mandible as intended by the clinician.

Embodiments of the present disclosure provide a way to apply (e.g., virtually attach) a sized, indexed, and adjusted guidance package to one or more retentive pieces to achieve a prescribed guidance profile for a specific patient. Afterwards, an appliance could be manufactured (e.g., printed using 3-D printing) having the applied guidance package.

Unfortunately, the position of the guidance package on the retentive piece(s) may be in conflict with some other consideration for the recipient, or the clinician has a specific end product like an implant retained denture, in which, although the guidance package system has provided the appropriate guidance profile to the prescribed maximum closure position, the topography and contact areas of that appliance or restoration must be different. These other considerations may guide a selection of potential solutions or limit a universe of acceptable solutions. For example, if a sleep apnea patient feels anxious about anteriorly placed guidance (e.g., in front of the front teeth), parameterization may be used to place the guidance on the posterior lateral aspects of the retentive pieces to achieve no interference with breathing as perceived by the patient. As another example, when creating one or more restorations with "prosthetic teeth" and implant retained dentures, it may be desirable to implement all guidance functionality with the shapes and inclinations of the prosthetic teeth so that a separate guidance package (e.g., retention piece) is not required.

The total working space for retentive pieces, guidance packages, and all other functions of the guidance package system is referred to as a global 3D region. Alternatively, multiple 3D regions may be defined for guidance package system calculations and modifications. The space between (or including) the mandibular retentive piece and the maxillary retentive piece at the prescribed maximum closure position of the mandible in relation to the maxilla has a geometric shape of an arch form that comports to that patients' skeletal frame of maxilla and mandible. It is further understood that within that total area and volume of that space (a 3D region that may be in a shape of a hyperbolic paraboloid) exists both the maxillary and mandibular guidance portions (that attach to their respective retentive pieces). Within this space the two interacting guidance pieces may be in contact but may not be connected. Those contact areas may involve the entire arch form of one or both arches, or only portions thereof.

Using various embodiments of the present disclosure, a desired guidance profile from first contact to maximum closure can be established within a virtual environment using a virtual articulator. The guidance profile provided by the interacting shapes upon closure of the mandible to the maximum closure position (or index position) in the context of range of motion of the plurality of the TMJs defines a region of space, and as such, may be considered a mathematical or virtual object that is amenable to parametrical representation achieving an arbitrary degree of precision in its approximation of this intrinsic object. By parameterizing the space between the maxillary and mandibular retentive pieces, an envelope (3D region) within which the areas, volumes, and the topography of the contact surfaces of the guidance and stop components can now be changed in concert with each other in a way that maintains the determined movement profile of the indexed, sized, adjusted and attached guidance package. The space between the retentive pieces may be considered a limited 3D region used for parameterization of the guidance package solutions. The space that includes room for parameterizing retentive piece(s), the guidance package solution, and other functions of the guidance package system may be considered a global 3D region. In different embodiments, these parameterizations may occur in various sequential or overlapping orders or simultaneously.

Various embodiments of the present disclosure allow for the production of many different retentive pieces, which can be used by a user/patient to obtain a desired movement profile. In some embodiments, the retentive piece(s) can be fixed or removable appliances such as bruxism, sleep apnea, and TMD appliances. In some embodiments, the retentive piece(s) can be a complete arch of fixed prosthetics like crowns and bridges mounted on teeth and/or implants. In some embodiments, the retentive piece(s) can be a removable appliance like a tooth or implant borne removable partial denture, or complete denture. In some embodiments, the retentive piece(s) can be a combination of any of the above prosthetic or patient features or modified patient features that reflect the full arch mechanics of the present disclosure system. In some embodiments, restorative, surgical, and implant placement guides may be derived from the guidance package system.

Certain embodiments discussed herein refer to placing a patient's jaws in a predetermined index position (e.g., a prescribed maximum closure position), such as centric relation (CR). It is to be understood that, while CR is a relaxed position for many bruxism patients, a predetermined index position (e.g., prescribed maximum closure position) may also refer to other relaxed positions such as a position chosen and/or refined by muscle testing or a relaxed position chosen by the dental professional using 3D radiography, MRI, sonography, other imaging, or a Jaw Motion Analyzer. Further, it should be understood that the predetermined index position may also refer to a position that is not necessarily relaxed but is, for example, otherwise chosen for its therapeutic value, including, but not limited to, a position selected by the dental/medical professional based on the damage or disease profile of the patient, a position selected by the dental/medical professional that adequately moves the mandible protrusively to address sleep apnea, and a therapeutic position selected by the dental professional using 3D radiography, MRI, sonography, other imaging, and/or a Jaw Motion Analyzer.

One or more virtual points may be generated based on one or more of the index position and one of the retentive pieces. A virtual guidance package may be positioned in virtual space based on the one or more virtual points. For example, in one embodiment, the virtual guidance package may be positioned based on a single virtual point without the need for orientation, alignment, or position data of either virtual retentive piece. In this fashion, the virtual guidance package may be a stock (e.g., preformed or pre-programmed) guidance package that is customized after it is positioned or a customized guidance package.

In another embodiment, the virtual guidance package may be positioned based on a single virtual point along with one or more of orientation, alignment, and position data of at least one of the virtual retentive pieces. The orientation, alignment, and/or position data of the virtual retentive piece(s) provide context for relative positioning of the virtual point in virtual 3D space. In this fashion, the virtual guidance package may be a stock guidance package that does not require customization, or a virtual guidance package that may require a reduced customization effort which may decrease the time and cost associated with producing the guidance package derived product for a particular patient.

In another embodiment, the virtual guidance package may be positioned based on three or more virtual points, which collectively provide context for relative positioning of the guidance package in three dimensions without requiring orientation, alignment, or position of the virtual retentive pieces. In this fashion, the virtual guidance package may be a stock guidance package that does not require customization, or may reduce the customization effort, which may decrease the time and cost associated with producing the guidance package derived product for a particular patient.

The guidance package may include a virtual maxillary guidance component and a virtual mandibular guidance component. After positioning the guidance package in virtual space, the virtual maxillary guidance component may be connected to the virtual maxillary retentive piece to form a first part of a virtual guidance package equipped appliance. Similarly, the virtual mandibular guidance component may be connected to the virtual mandibular retentive piece to form a second part of the virtual guidance package equipped appliance. The virtual maxillary guidance component and the virtual maxillary guidance component may be pre-oriented towards one another in a correct orientation. The correct orientation may be maintained until the virtual guidance components are connected to the respective virtual retentive pieces. Guidance package equipped appliance production data based on the first and second parts of the virtual guidance package equipped appliance can then be transmitted. For example, the guidance package equipped appliance production data may be transmitted to a manufacturer equipped with one or more of CAM, CNC technology, an in-office 3D printer, mill, and other additive and/or reductive CAM production device(s).

In other embodiments, generating the one or more virtual points may include positioning the one or more virtual points to provide a threshold clearance (e.g., 1 mm or more) between the virtual maxillary retentive piece and the virtual mandibular retentive piece.

In some embodiments, the method may also include virtually simulating movement of the virtual guidance package equipped appliance. For example, in some embodiments, movement of a stock guidance package may be simulated to help determine which stock guidance package is most appropriate for a particular patient for a particular purpose, and/or whether customization of the selected stock guidance package is required. If a guidance package is customized, the movement of the customized guidance package may be simulated to confirm that it will operate as intended and, if necessary, indicate a need for further customization prior to producing a physical guidance package derived appliance. This can help decrease time and cost associated with producing the customized guidance package for a particular patient, as it avoids multiple iterations of testing movement of a physical guidance package derived appliance in a patient's mouth. It may also provide increased accuracy as the dental practitioner may have improved visibility in the virtual model compared to a physical model placed within a patient's mouth.

In some embodiments, generating the one or more virtual points may include positioning two virtual points that are bilaterally equidistant from a reference plane. The reference plane may be perpendicular to a mid-sagittal plane and positioned at a specific distance (in some examples about 6 mm) from a most anterior aspect of one of the virtual retentive pieces (e.g., the maxillary retentive piece) along an occlusal plane mid-sagittally. Further, connecting one of the virtual guidance components (e.g., the maxillary guidance component) to one of the virtual retentive pieces (e.g., the maxillary retentive piece) may be based on the two virtual points and an orientation, alignment, and/or position of the other virtual retentive piece (e.g., the mandibular retentive piece)

In other embodiments, generating the one or more virtual points may include positioning one virtual point proximate a reference plane positioned at a specific distance (in some examples about 6 mm) from a most anterior aspect of one of the virtual retentive pieces (e.g., the maxillary retentive piece) along an occlusal plane mid-sagittally. The reference plane may be perpendicular to a mid-sagittal plane. Further, connecting one of the virtual guidance components (e.g., the maxillary guidance component) to its respective virtual retentive piece (e.g., the maxillary retentive piece) may be based on the virtual point and an orientation, alignment, and/or position of the other virtual retentive piece (e.g., the mandibular retentive piece). In some embodiments, the virtual point may be placed 3Dly (e.g., as a 3D vector) so that a guidance package may be used without modification or to minimize modification. If the virtual point is a 3D vector, the direction may indicate an orientation of a movement profile and its magnitude may indicate a scaling of the movement profile.

In some embodiments, obtaining patient data may further include obtaining TMJ data associated with left and right TMJs of the patient.

Positioning the virtual guidance package in virtual space may include positioning the virtual guidance package in a guidance package index position such that the mandible is adjusted outside of centric relation based on the virtual point. By adjusting the mandible, the guidance package index position may be configured to protrusively, laterally, and vertically recapture the left and right TMJ discs. Further, connecting one of the virtual guidance components (e.g., the maxillary guidance component) to its respective virtual retentive piece (e.g., the maxillary retentive piece) may be based on the guidance package index position and an orientation, alignment, and/or position of the other virtual retentive piece (e.g., the mandibular retentive piece).

In some embodiments, one of the left and right TMJ condyles must travel further than the other TMJ condyle for the recapture of its relative disc.

In other embodiments, obtaining patient data may further include obtaining TMJ data associated with left and right TMJs of the patient, one of the left and right TMJ discs being anteriorly displaced or damaged. Generating the one or more virtual points may include asymmetrically positioning one or more virtual points in relation to a mid-sagittal plane proximate a plane perpendicular to the mid-sagittal plane that is positioned at a specific distance (in some examples about 6 mm) from a most anterior aspect of one of the virtual retentive pieces (e.g., the maxillary retentive piece) along an occlusal plane mid-sagittally. Positioning the virtual guidance package in virtual space may include positioning the virtual guidance package in a guidance package index position such that the mandible is configured to recapture the damaged TMJ disc based on the one or more virtual points. Further, connecting one of the virtual guidance components (e.g., the maxillary guidance component) to its respective virtual retentive piece (e.g., the maxillary retentive piece) may be based on the guidance package index position and an orientation, alignment, and/or position of the other virtual retentive piece (e.g., the mandibular retentive piece).

In some embodiments, the guidance package index position may adjust the mandible such that it is configured to recapture the damaged TMJ disc while allowing the other TMJ disc to remain in a centric relation position, or other rest position.

In other embodiments, obtaining patient data may further include obtaining damaged structure data associated with the patient. Generating the one or more virtual points may include positioning one virtual point proximate a mid-sagittal plane and proximate a plane perpendicular to the mid-sagittal plane that is positioned at a specific distance (in some examples about 6 mm) anterior to a most anterior aspect of one of the virtual retentive pieces (e.g., the maxillary retentive piece) along an occlusal plane mid-sagittally. In other embodiments, generating one or more virtual points may include positioning one or more virtual point(s) 3Dly within the frontal, sagittal, and transverse planes. Positioning the virtual guidance package in virtual space may include positioning the virtual guidance package in a guidance package index position configured to treat one or more of a mandible, a TMJ, and a stomatognathic condition of the patient based on the damaged structure data, or a reconstruction due to caries, periodontal disease, edentulism, and/other medical and/or dental reasons. In some embodiments, the guidance package index position may be configured to adjust the mandible out of centric relation. Further, connecting one of the virtual guidance components (e.g., the maxillary guidance component) to its respective virtual retentive piece (e.g., the maxillary retentive piece) may be based on the guidance package index position and an orientation, alignment, and/or position of the other virtual retentive piece (e.g., the mandibular retentive piece).

In some embodiments, the damaged structure data may indicate that one of a left side or a right side of a mandible of the patient is damaged. Further, positioning the virtual AGP package in virtual space may include protrusively moving the damaged side of the mandible to advance a condyle of the damaged side out of a centric relation position while allowing the undamaged side of the mandible to keep a condyle of the undamaged side in the centric relation (or other rest) position.

According to some implementations, instructions for steps or functions of one or more example embodiments may be stored in data modules. In some cases, the data modules may be executed by a processor or system to perform a method according to an example embodiment of the present disclosure. In some implementations, there may be provided a system that includes one or more processors and a memory having software code that, when executed by the one or more processors, is configured to control the system to execute functions or methods according to one or more example embodiments.

Reference will now be made to the figures, to further describe aspects of one or more example embodiments. One of ordinary skill will understand that the features described with reference to the drawings are merely examples, and certain implementations may include fewer, additional, or modified elements are anticipated by this disclosure. In some cases, certain well-known elements may be omitted for compactness.

Referring to FIG. 1, FIG. 1 illustrates an example guidance package kit. The guidance package kit 1 of FIG. 1 may include a guidance package 4-S. The guidance package 4-S may be a "simple" guidance package (e.g., a preformed physical guidance package). The simple guidance package 4-S may be used to ameliorate damage and pain caused by bruxism, or other purpose. The guidance package kit 1 could be delivered from the manufacturer, as shown in FIG. 1, or the guidance package may be already attached to a retentive piece for one arch (e.g., the maxillary or mandibular arch) and then indexed onto a retentive piece molded to the other arch. In some embodiments, the simple guidance package 4-S may be indexed by a dental professional onto a shelf or shelves of the retentive piece or pieces. The guidance package kit 1 may include a maxillary guidance component 1-1, a mandibular guidance component 1-2, and a holder 1-3 that temporarily holds the two components 1-1 and 1-2 together at a desired position. A physical guidance package in any form may include a maxillary guidance component 1-1, a mandibular guidance component 1-2, and the temporary holder 1-3, and may constitute a simple guidance package 4-S. As with any guidance package 4 construction, the guidance package 4 may be represented and manipulated virtually and/or mathematically in a virtual environment.

In some embodiments, as with any guidance package 4 construction, steepness 33 and depth 32 of the areas of lateral and protrusive guidance on the maxillary component 1-1 of the simple guidance package 4-S can be controlled or modified to provide anterior stops and guidance to the mandible for a very wide range of treatment goals that the operator may have in mind.

Figure 2A:
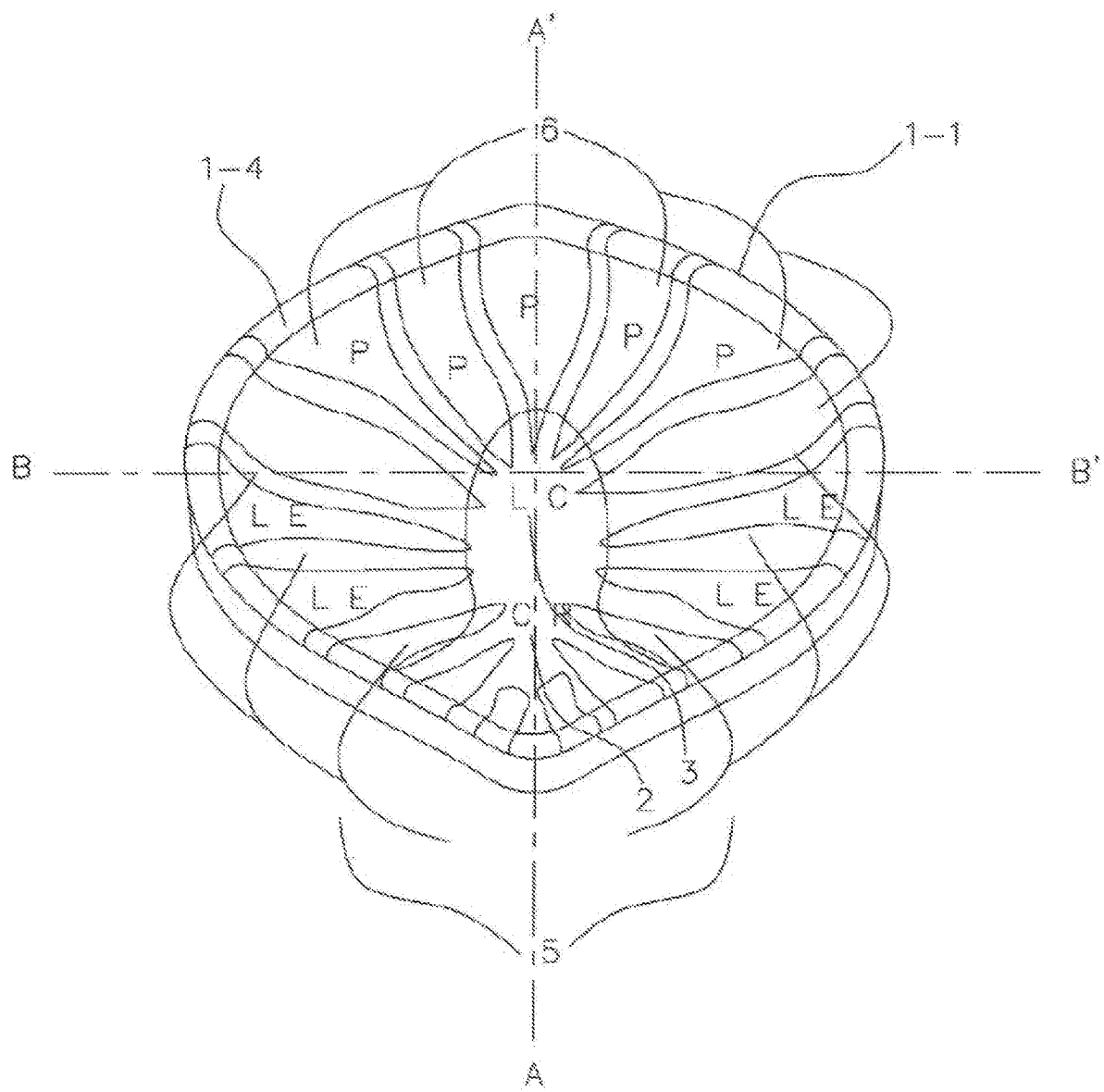
FIG. 2A is an overhead view of the internal topography of a maxillary guidance component of a guidance package in accordance with an example embodiment.
Figure 2B:
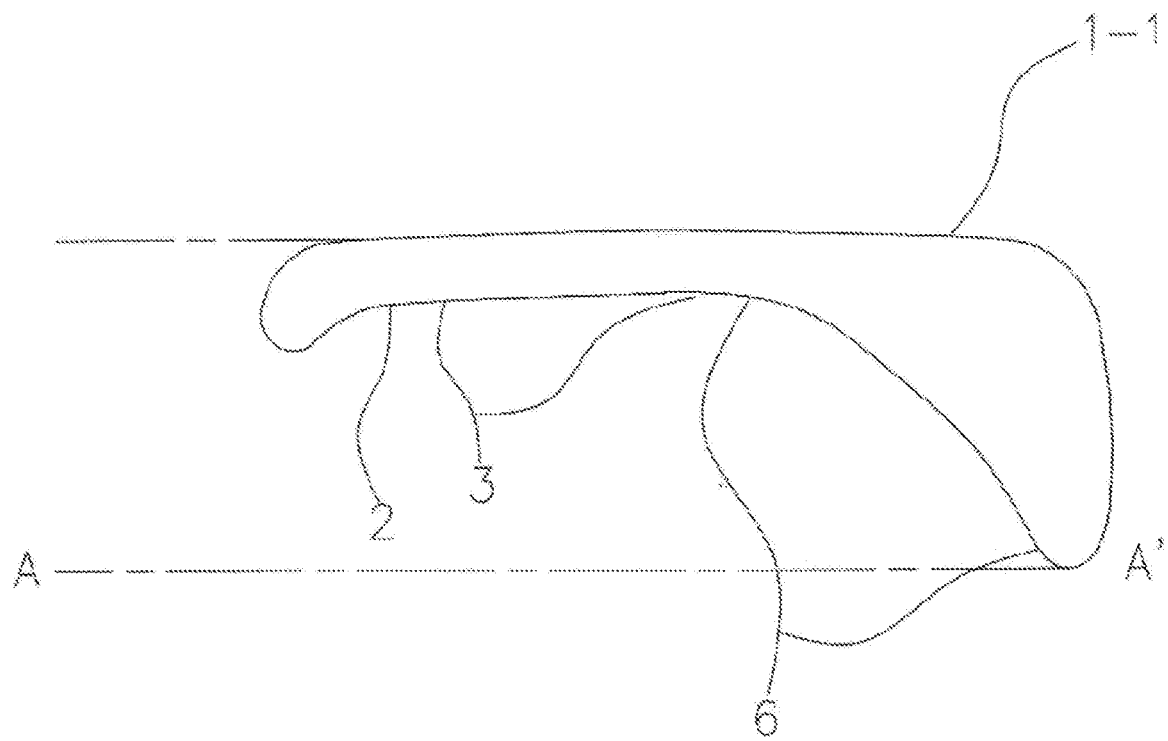
FIG. 2B is an enlarged cross-sectional view of a maxillary guidance component of a simple guidance package along line A-A' of FIG. 2A in accordance with an example embodiment.
Figure 2C:
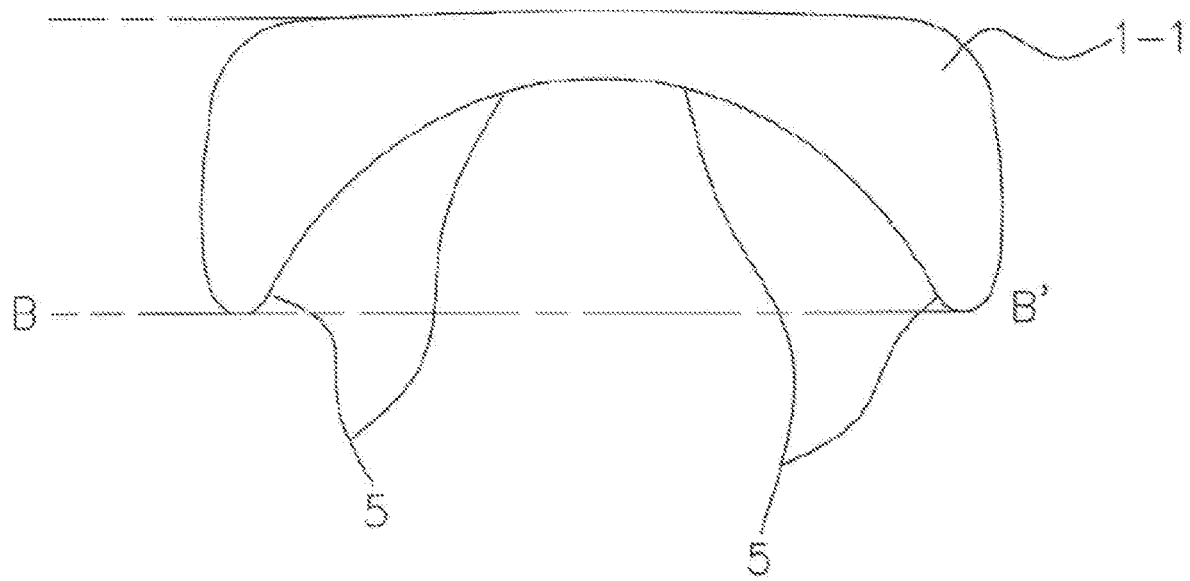
FIG. 2C is an enlarged cross-sectional view of a maxillary guidance component of a simple guidance package along line B-B' of FIG. 2A in accordance with an example embodiment.

FIGS. 2A-2C shows the internal topography of the maxillary guidance component 1-1 of an example simple guidance package 4-S according to an example embodiment.

FIG. 2A is an overhead view of the internal topography of a maxillary guidance component of a guidance package in accordance with an example embodiment. FIG. 2B is an enlarged cross-sectional view of a maxillary guidance component of a simple guidance package along line A-A' of FIG. 2A in accordance with an example embodiment. FIG. 2C is an enlarged cross-sectional view of a maxillary guidance component of a simple guidance package along line B-B' of FIG. 2A in accordance with an example embodiment. The internal topography includes a specific guidance of a CR stop 2, a long centric (LC) area 3, a lateral excursion (LE) guidance 5, and a protrusive (P) guidance 6. As shown in FIGS. 2A-2C, the maxillary guidance component 1-1 of the simple guidance package 4-S may have a flat area for a stable CR stop 2 extended into a further area of flat for the LC position 3 of the mandible extending laterally and anteriorly into blended inclines of a concave inferiorly oriented shape for LE guidance 5 (FIG. 2C) and protrusive (P) excursion guidance 6 (FIG. 2B) to provide ideal anterior guidance to the patient's mandible by the mandibular guidance component 1-2 against these features of the maxillary guidance component 1-1 to minimize muscular force and avoid all posterior interferences. This feature of appropriate anterior guidance, which moves the mandible downward (inferiorly) in its excursions, may allow for a night guard of significantly less vertical dimension at rest than other designs, much like an ideal occlusion would. It is contemplated that the maxillary guidance component 1-1 may take on any size based on a patient's range of motion.

Figure 3:
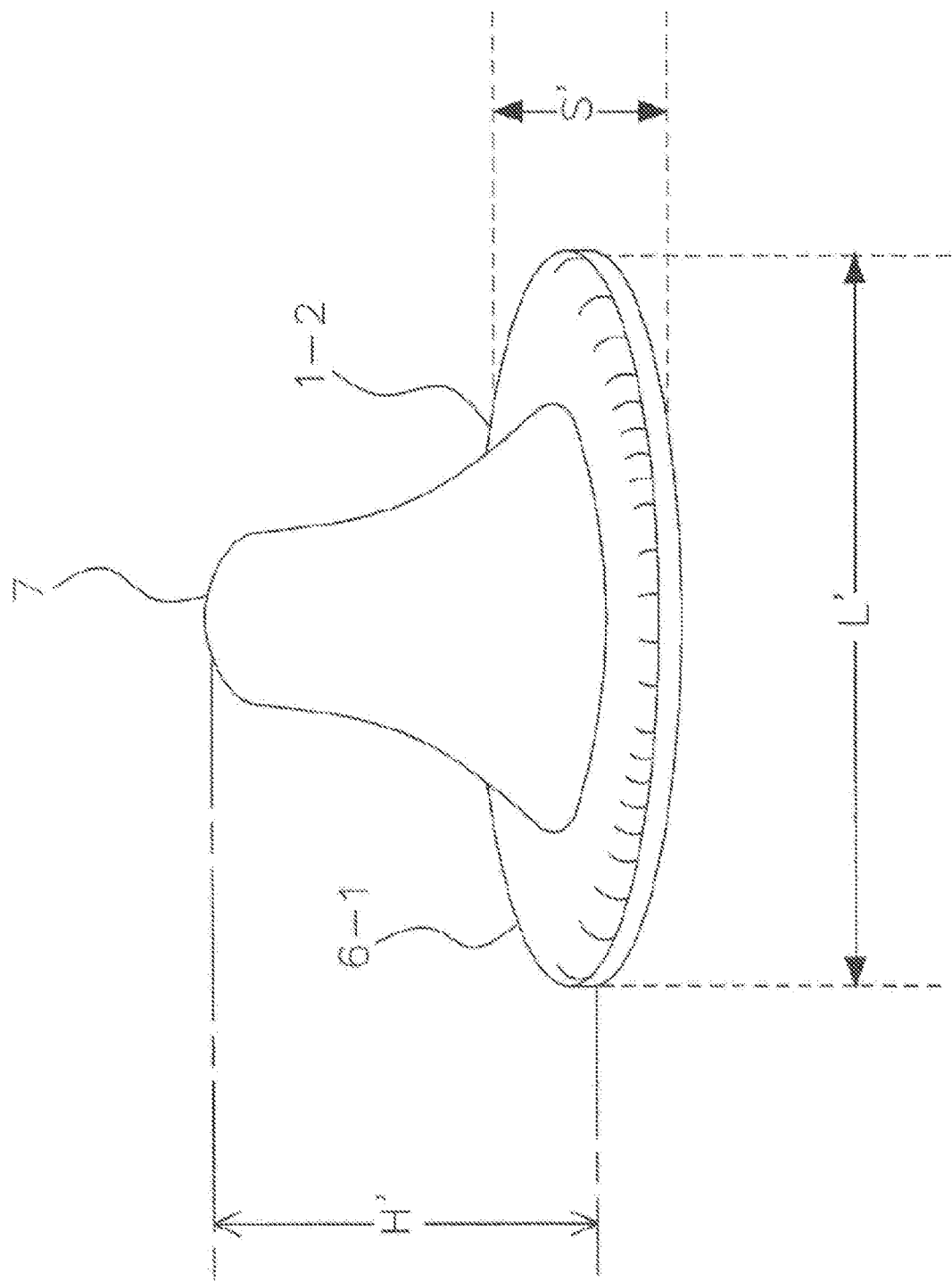
FIG. 3 is a perspective view of a mandibular guidance component of a simple guidance package in accordance with an example embodiment.

FIG. 3 shows the mandibular guidance component 1-2 of the simple guidance package 4-S kit 1. A base 6-1 of the mandibular guidance component 1-2 may have a superellipse or arch form shape and a same dimension or similar as the maxillary guidance component 1-1, as shown in FIG. 2A.

In some embodiments, the length of the long axis L' of the oval shaped mandibular guidance component 1-2 may be, including but not limited to, between 15 to 35 mm. The length of the short axis (S') of the oval shaped mandibular guidance component 1-2 may be, including but not limited to, between 8 to 20 mm. A smooth rounded protrusion 7 may be developed on one surface of the mandibular guidance component 1-2. A tip of the protrusion 7 may become engaged in the flat to concave inner surface of the maxillary guidance component 1-1 and guide and limit the movement of a patient's mandible. In some embodiments, the height H' of the smooth protrusion may be, including but not limited to, between I to 6 mm. For example, in one embodiment, the height H' may be about 5 mm. As with any guidance package 4 construction, the steepness and depth of the protrusion(s) 7 of the mandibular component 1-2 of the simple guidance package 4-S can be controlled to provide anterior stops and guidance to the mandible for a wide range of treatment goals the dental professional may have in mind.

Figure 4:
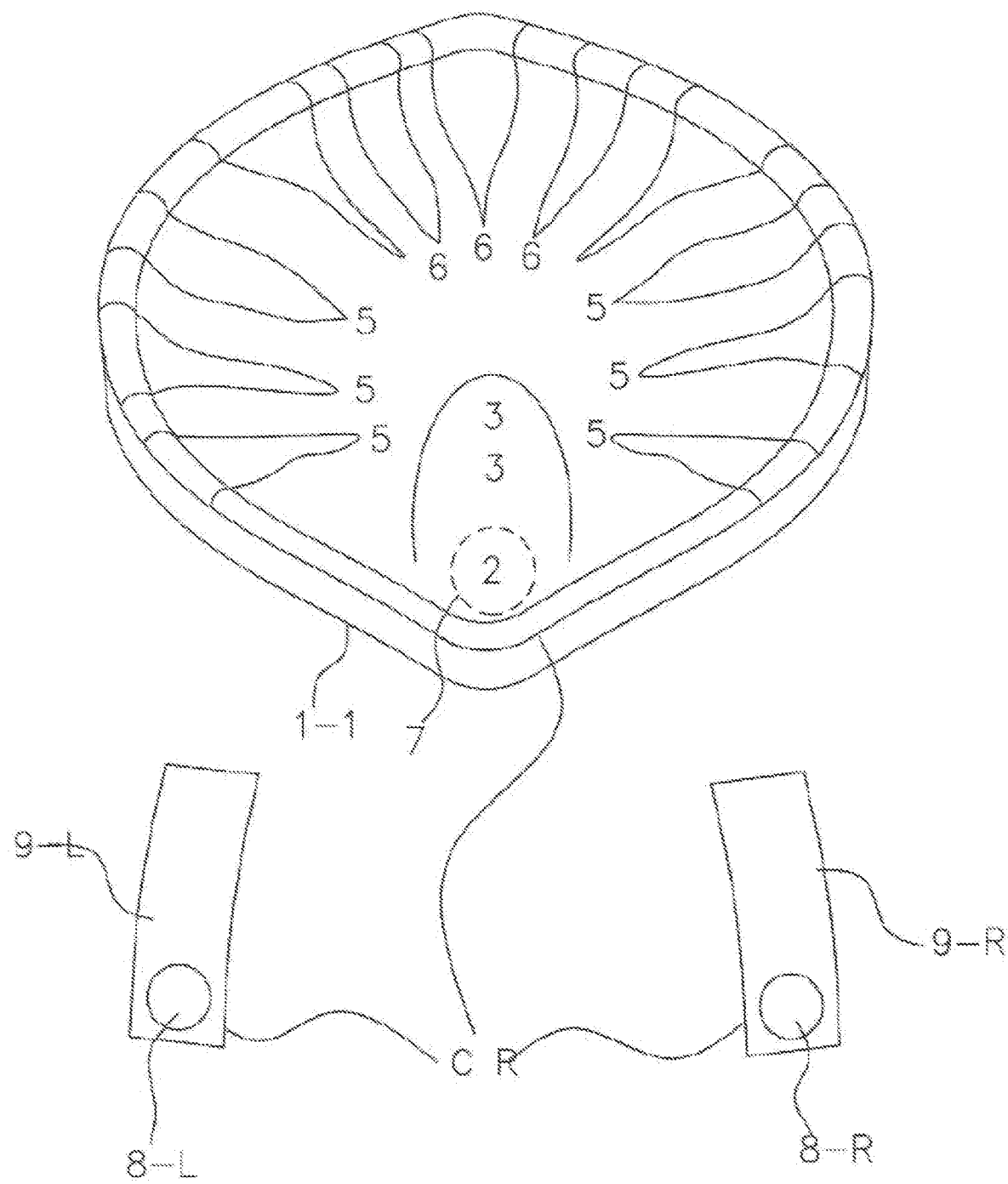
FIG. 4 is a transparent view of a simple guidance package positioned when the mandible is in a centric relation hinge axis at appropriate vertical dimension position in accordance with an example embodiment.

FIG. 4 shows the simple guidance package 4-S correlating with the CR position of the TMJs 9-R and 9-L, which represent the right and left TMJs, respectively. In some embodiments, as shown, the guidance package 4 may replicate ideal anterior guidance. In the context of bruxism, for example, ideal anterior guidance would provide the patient with immediate elimination of all posterior interferences by the patient's anterior teeth or, in this example by the guidance components of the simple AGP, in any excursion of the mandible. A reference point 2 represents where the protrusion 7 of the mandibular guidance component 1-2 sits at rest in the maxillary guidance component 1-1 when right and left condyles 8-R and 8-L of the TMJs 9-R and 9-L of the mandible are in their CR position. As a patient functions or bruxes his mandible, the mandibular guidance component 1-2 may provide ideal anterior guidance for the mandible by means of the mandibular guidance component 1-2 functioning against the maxillary guidance component 1-1 in the position of CR 2, LC 3, LE 5, and P guidance 6. In some embodiments, the guidance package 4 may provide ideal anterior guidance without regard to the position of teeth, the condition of teeth or missing teeth. For example, the guidance package may be indexed and attached to retentive pieces within the retentive piece system rather than being attached directly to the teeth or arch.

Figure 5:
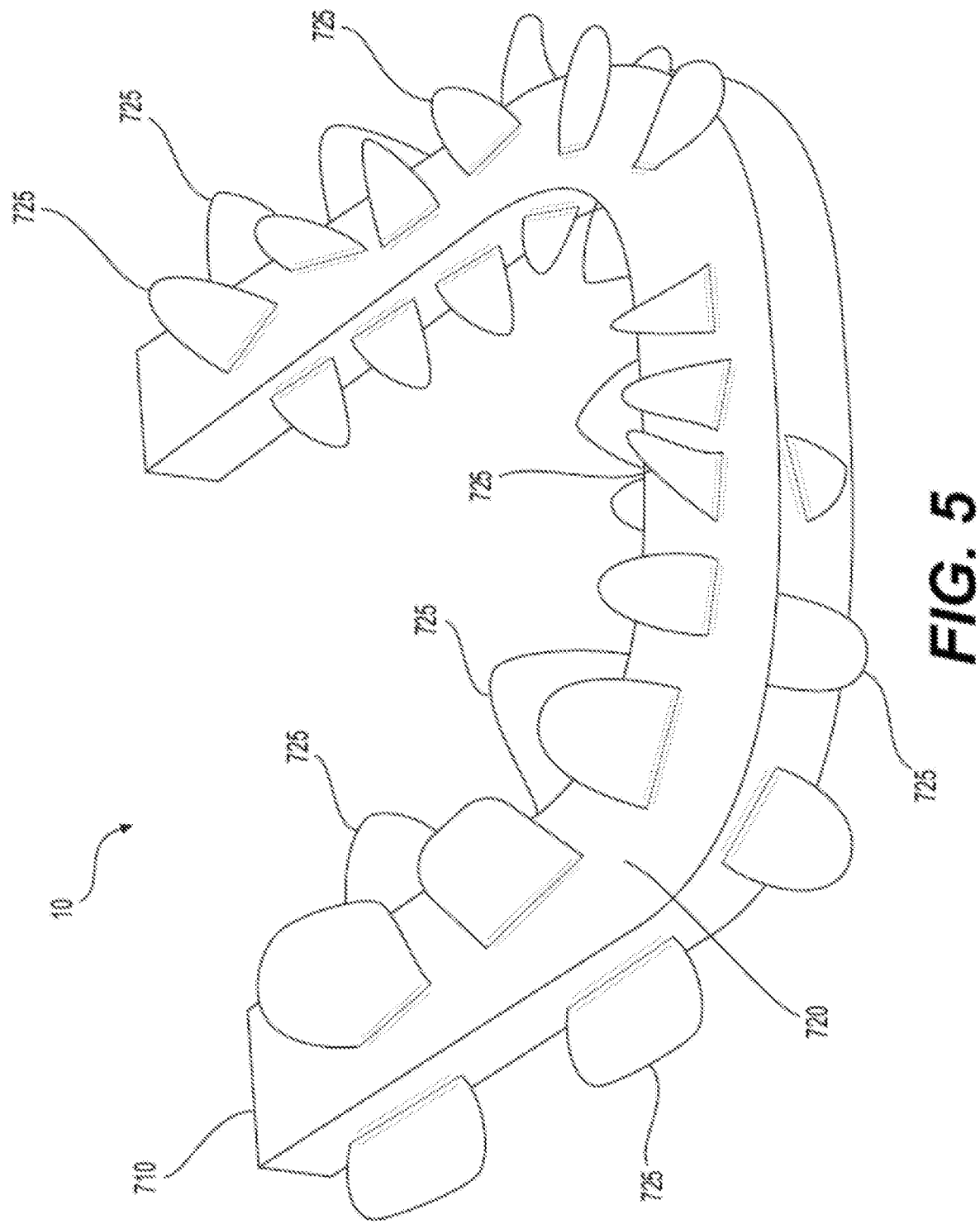
FIG. 5 is a perspective view of a virtual or physical retentive piece configured to receive a guidance package in accordance with an example embodiment.

FIG. 5 illustrates a retentive piece according to an example embodiment. Retentive piece 10 may facilitate the application of the guidance package to a broad spectrum of patients with a wide range of maladies, occlusions and malocclusions. The retentive piece 10 may be disposed on or around the maxilla or mandible, and may have a shelf or protrusion to receive the appropriate component of the guidance package 4.

Many different retentive pieces can be provided in accordance with various embodiments of the present disclosure. FIG. 5 illustrates a retentive piece, in accordance with an example embodiment of the present disclosure. The retentive piece may be thin and conform totally or partially to the anatomy of the patient's arch (maxilla or mandible). The retentive piece 10 includes a tissue side 710 and a guidance side 720. The tissue side 710 of the retentive piece is configured to face or contact tissue of the patient, for example, teeth, bone, gum, and could be other prosthetics. The tissue side 710 may totally or partially conform to the tissue of the respective arch. The retentive piece may be connected to the tissue by a variety of mechanisms to include implants, mini implants, prepped or not prepped teeth, other physical features, adhesive, tight fitting compressive plastic, a vacuum, wire, clasps, bonding materials or other attachment mechanism. In some cases, the retentive piece may be formed with a space to accommodate one or more of the connection mechanisms.

The guidance side 720 of the retentive piece 10 may be connectable to a guidance and/or stop component. For example, the guidance side 720 may have multiple protrusions, shelves, or attachment surfaces in various shapes and sizes that serve as attachment points and/or platforms for guidance packages or portions of guidance packages. In some embodiments, the guidance side 720 of the retentive piece 10 may have formed thereon guidance and stop features generated by guidance packages of the present disclosure. These protrusions and shelves (e.g. 725) may be located on all surfaces of the guidance side 720 of the retentive piece 10 to include facial, lingual, and occlusal/incisal. In some embodiments, the retentive piece 10 may be a virtual retentive piece 10. In this case, once a guidance package is selected and an appropriate attachment point is determined, one or more other protrusions, shelves, or attachment surfaces may be removed before the designed retentive piece 10 is physically created.

With the retentive piece 10, the guidance package 4 equipped appliance may be suitable for patients who have different types of occlusions and malocclusions and have bruxism at the same time, or a TMJ disorder, other stomatognathic damage, or a sleep apnea disorder. The guidance package appliance may be produced with specific jaw repositioning and guidance limitations as prescribed by the dental professional.

Figure 6:
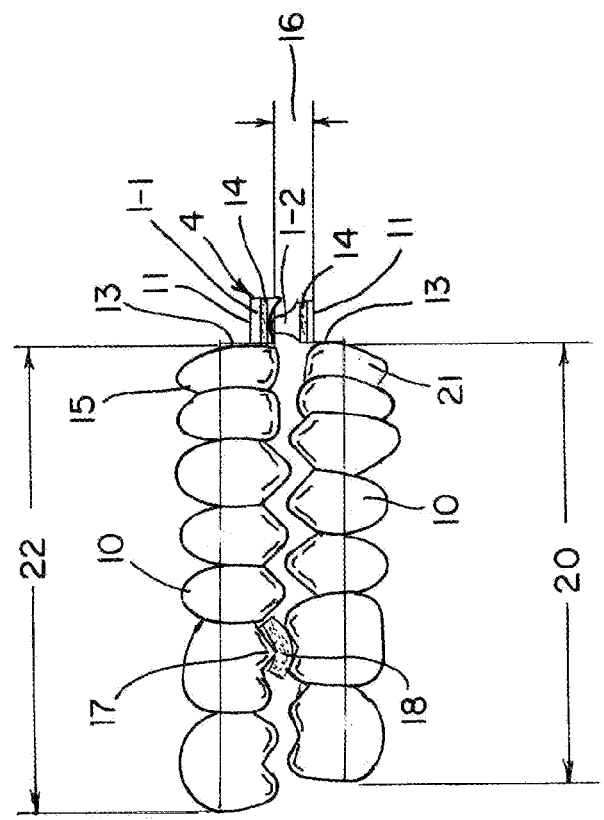
FIG. 6 is a schematic drawing showing an example method for using retentive pieces as platforms and attachment points for a guidance package for both the maxillary and mandibular arches.
Figure 6:
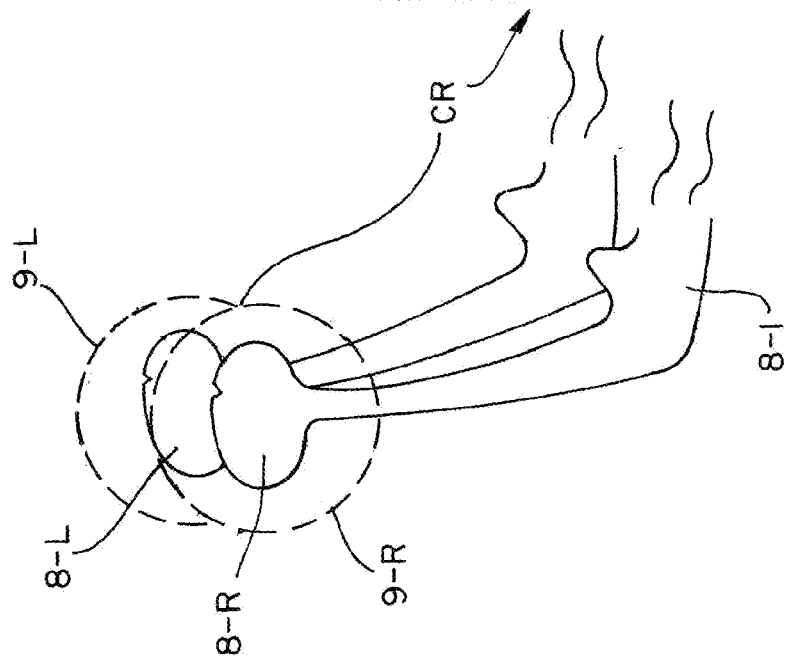

FIG. 6 shows an example application of the retentive piece for both the maxillary and mandibular retentive pieces to enable the guidance package to be placed anterior to the anterior teeth to include an appliance 13 that is a combination of the retentive pieces 10 and a guidance package 4. In some embodiments, the guidance package 4 may be attached to the shelf/protrusion 11 via glue 14. In other embodiments, the guidance package 4 may be attached to the shelf/protrusion 11 via any chemical or mechanical means. In other embodiments, the virtual guidance package 4 may be attached to the virtual shelf/protrusion. As shown, the space between the retentive pieces 10 for the mandible and maxilla is exaggerated to help visualize a first contact point 17 and relative interferences (or collisions) of cusps of the teeth. The first contact point 17 is the first point of contact between maxillary and mandibular teeth as the patient's jaw is closed into the index position by the dental professional. The application of this appliance to this patient using anterior guidance and the threshold clearance avoids this otherwise unwanted point of first contact 17.

In some embodiments, the guidance package 4 may provide anterior guidance that is not dependent upon teeth. For example, the guidance package 4, and therefore the anterior guidance, may be placed anterior to the most anterior teeth (15 and 21). This configuration may increase the mechanical advantage of the guidance package 4 over the muscles of mastication in excursions.

Further, by placing the guidance package 4 further anterior than the actual position of the maxillary anterior teeth and/or the mandibular anterior teeth 15 and/or 21, the guidance package 4 may provide anterior guidance with minimal vertical dimension 16 increase when the patient's mandible is at rest in CR (or another predetermined index position/prescribed maximum closure position). As the guidance package 4 can be positioned anterior to both the maxillary anterior teeth 15 and the mandibular anterior teeth 21, the guidance package 4 can provide 3D anterior guidance displacing the mandible inferiorly in excursions to help eliminate interferences (e.g., collisions). Further, as the guidance package 4 and retentive pieces 10 minimize the vertical dimension 16 when the patient is in the predetermined index position (prescribed maximum closure position), the patient's acceptance and comfort may increase dramatically. Some example methods for finding the first contact 17 and the use of a spacer 18 (e.g., a 1 mm sticky but removable spacer) to identify and create appropriate space in CR (or the predetermined index position) are described in detail in U.S. Patent App. Pub. No. 2014/0060549.

Figure 7:
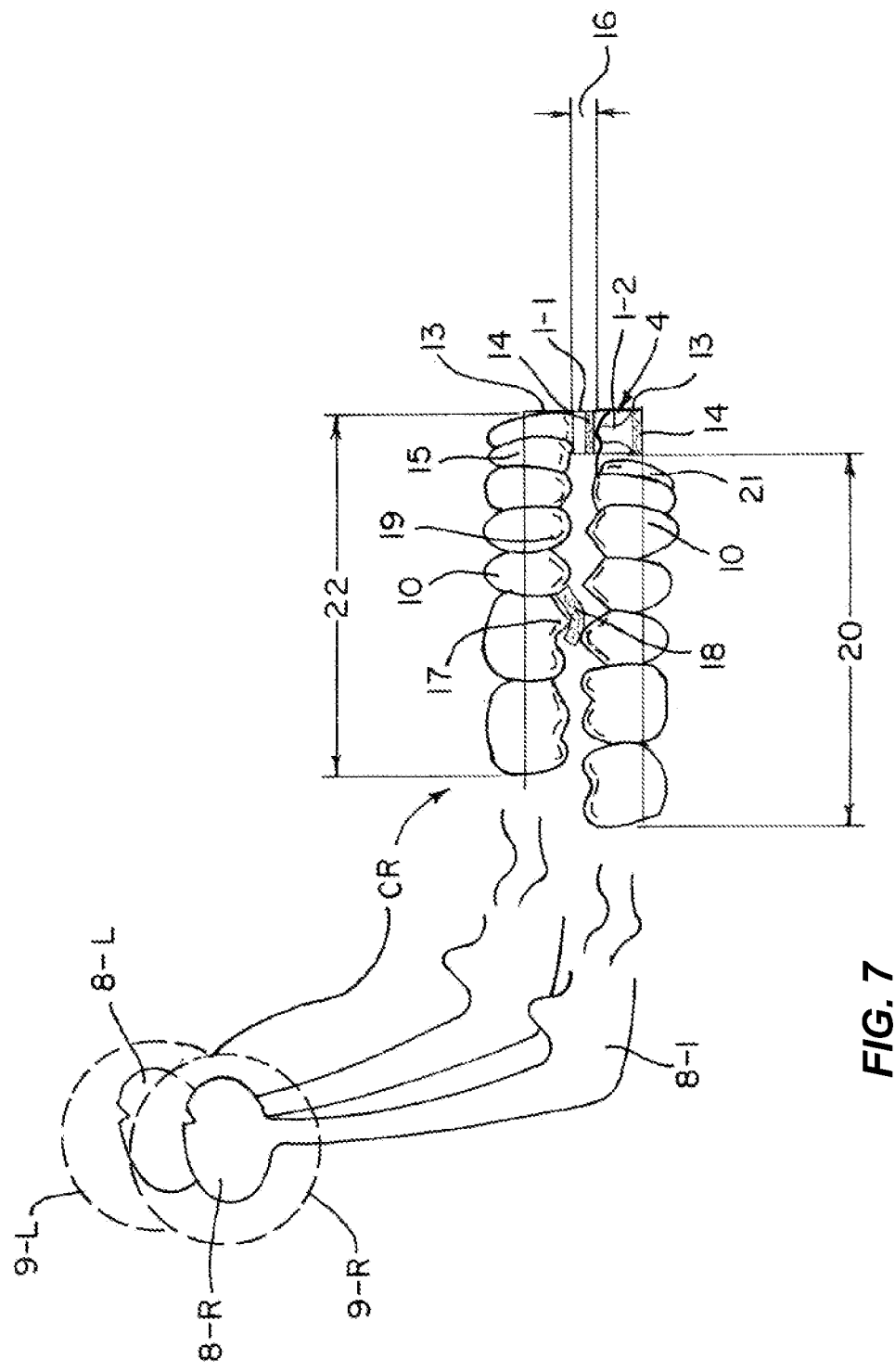
FIG. 7 is a schematic drawing showing an example method for using retentive pieces for a patient with a significant Class II malocclusion.
Figure 8:
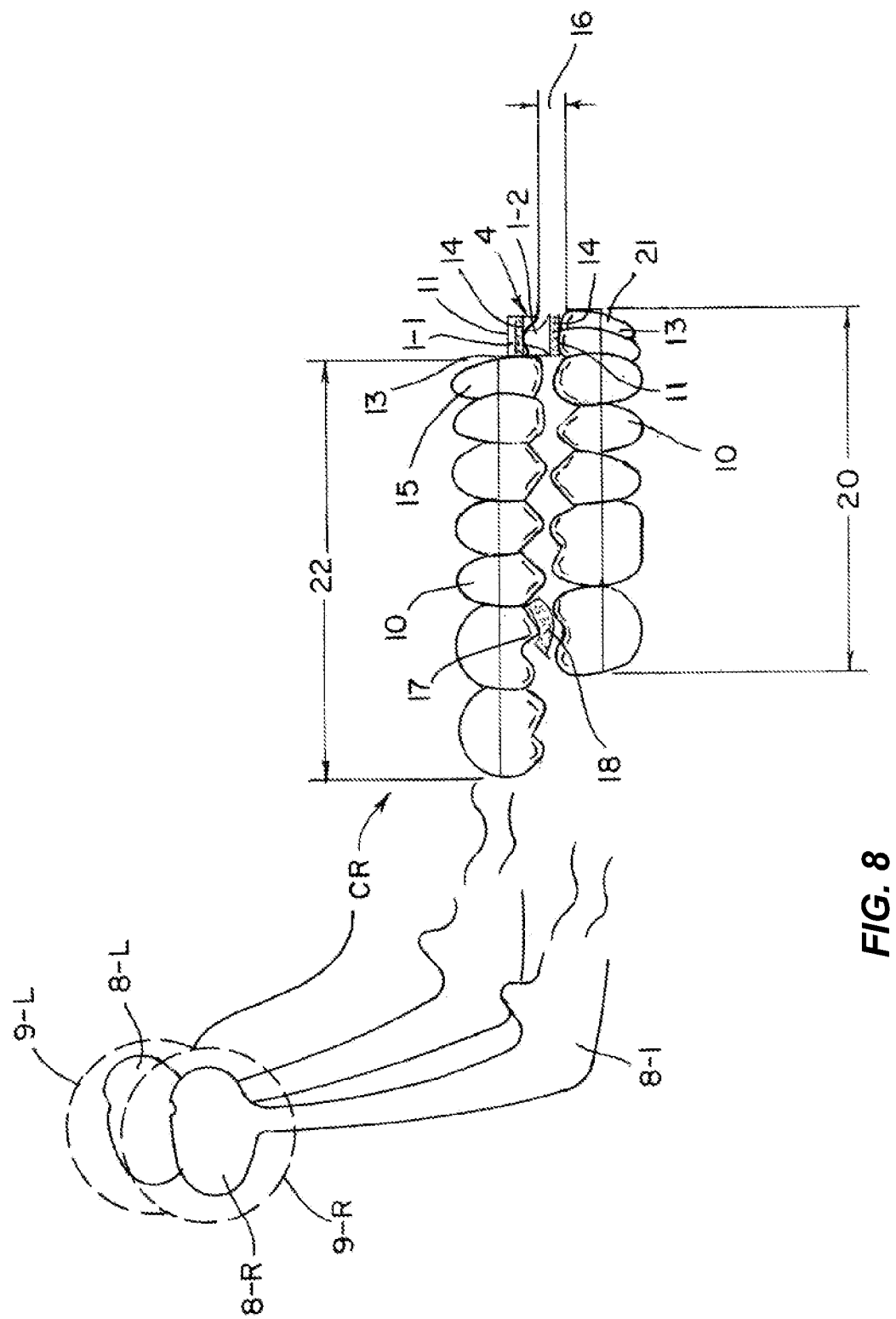
FIG. 8 is a schematic drawing showing an example method for using special retentive pieces for a patient with a significant Class III malocclusion.

FIGS. 7 and 8 illustrate example uses of retentive pieces 10 for a patient who presents with a significant Class II malocclusion and with a significant Class II malocclusion, respectively.

In FIG. 7, the retentive pieces 10 are placed on the patient's retrognathic mandibular arch 20, and on the patient's maxillary arch 22 to treat bruxism of a patient with a significant Class II malocclusion. The retentive piece 10 may allow for placement of the guidance package 4, and therefore anterior guidance, anterior to the anatomical position of the mandibular front teeth 21. As shown, the vertical dimension 16 of the guidance package derived appliance 13 at rest may be minimized by using retentive pieces 10. In this configuration, a patient suffering significant Class II malocclusion and bruxism may have a night guard with much greater mechanical advantage over the muscles of mastication in excursions from CR and may be more comfortable due to minimal vertical dimension 16 increase at rest in CR. Also, a dental professional can provide a proper night guard for a patient who has these problems with much less effort.

In FIG. 8, the retentive pieces 10 are placed on the patient's maxillary arch 22, and placed on the patient's mandibular arch 20 to treat bruxism of a patient with a significant Class III malocclusion. The retentive piece 10 may allow for placement of the guidance package 4 anterior to the anatomical limitation of the maxillary front teeth 15. As shown, the vertical dimension 16 for a patient at rest using the guidance package derived appliance 13 may be minimized due to the flexibility of guidance package placement within and around the retentive piece system. In this configuration, a patient suffering significant Class III malocclusion and bruxism may have a night guard with much greater mechanical advantage over the muscles of mastication in excursions from CR, and may be more comfortable due to minimal vertical dimension 16 increase at rest in CR. Also, a dental professional can provide a proper night guard for a patient who has these problems with much less effort.

In some embodiments, the guidance package 4 may be attached to the opposite retentive pieces 10 (e.g., "upside-down") and with proper rotation of the guidance package 4. In other words, the maxillary guidance component of the guidance package 1-1 may be attached to a mandibular retentive piece and the mandibular guidance component of the guidance package 1-2 may be attached to a maxillary retentive piece, such that the guidance package 4 can be used interchangeably with the maxillary and mandibular retentive pieces.

The guidance package 4 may be configured to provide guidance and limits to the front end of the mandible 3Dly independent of malocclusion or condition of the patients' teeth.

The guidance package 4 may be available in different stock configurations, which could be modified by the dental professional, and in the context of a CAD-CAM guidance package (a virtual or mathematical form of the guidance package 4), the guidance package 4 could be designed by the dental professional from a template based on diagnostic information and a damage profile of a particular patient. This customizable guidance package 4 may offer a wide range of solutions for treating patients with bruxism, or TMD, or sleep apnea, and various occlusions and malocclusions. The guidance package 4 may provide the dental professional with a broad spectrum of 3D patterning to guide the patient's mandible to the selected destination by a wide range of 3D routes.

Real human malocclusions can be complex, and are generally classified as Class I, II, or III. These occlusions and malocclusions can be further complicated by anterior and posterior crossbites, overjet, deep bite, open bite and other modifiers and combinations thereof.

In regard to bruxism appliances, a guidance package equipped appliance may be configured to treat a plethora of different occlusions and malocclusions, provide anterior guidance to neutralize posterior interferences to allow the patient's mandible to function in the best stress bearing position of CR even under the stress of bruxism, eliminate engrams of interferences to decrease inappropriate muscle activity and spasticity, give protection to the teeth and the TMJ, the reduction of myo-facial pain syndrome, and the reduction of migraine headaches.

Figure 9:
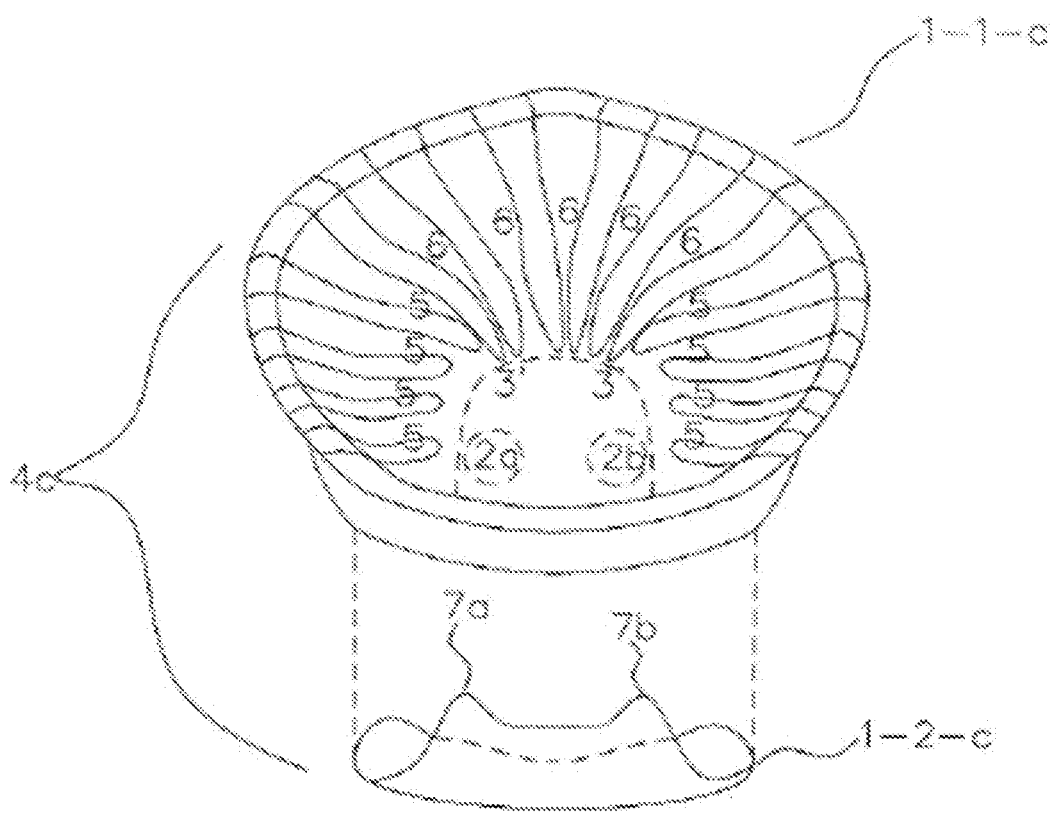
FIG. 9 is a planar perspective view of a "canine guidance" guidance package for a patient with bruxism in accordance with an example embodiment.
Figure 9:
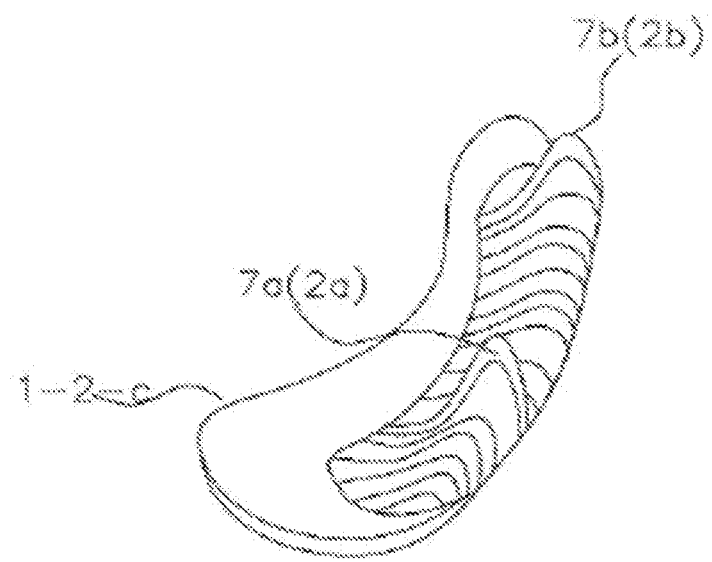

FIG. 9 shows an example design, of a different guidance package 4, a "canine guidance" package 4C (e.g., a bruxism, TMD or otherwise restorative guidance package). In some embodiments, there may be two protrusions 7a and 7b on the mandibular component 1-2-C of the guidance package 4-C spaced laterally apart in a way that would mimic ideal human "canine" anterior guidance. In other words, the mandibular guidance component 1-2-C of the guidance package 4-C which mimics ideal lower canines, may function against the maxillary guidance component 1-1-C of the guidance package 4-C, which mimics ideal maxillary teeth in a human exhibiting ideal canine guidance.

This design may be particularly suited for patients whose interferences (e.g., malocclusions) can be more efficiently neutralized by anterior guidance focused upon lateral poles of the mandibular guidance component 1-2-C of the guidance package 4-C, as compared to a single pointed protrusion 7 of the mandibular guidance component 1-2 of FIG. 3, when a patient wears the appliance 13 and bruxes.

The maxillary component 1-1-C of the guidance package 4-C may be modified to provide 3D guidance and limits to the mandible according to canine guidance when the patient bruxes. The mandibular component 1-2-C may be modified to provide 3D guidance and limits to the mandible according to canine guidance when the patient bruxes. In some embodiments, the maxillary component 1-1-C of the guidance package 4-C may have a concave inner surface with a cross-sectional shape in a horizontal plane forming a superellipse or arch form with convex outer sides. In other embodiments, the maxillary component 1-1-C may take on any shape configured to mate with the mandibular guidance component 1-2-C. The size of the maxillary component 1-1-C may be, for example, less than 50 mm by 50 mm dependent upon the full range of motion and border limits of the mandible both horizontally and vertically for a particular patient. In this example embodiment, there are two areas of CR contact 2a and 2b on the posterior aspect of the flat area of the maxillary component 1-1-C with a much broader area of long centric 3' on the anterior aspect of the flat area of the maxillary component 1-1-C. The steepness 33 and depth 32, as shown in FIG. 1, of the areas of lateral and protrusive guidance on the maxillary component 1-1-C of the guidance package 4-C can be controlled or modified to provide anterior stops and guidance to the mandible for a very wide range of treatment goals that the dental professional may have in mind.

In some embodiments, when the patient moves his mandible in laterotrusion to the left, only the left protrusion 7b may be in contact. As the patient moves his mandible back to CR, the right protrusion 7a may move back into contact simultaneous with the left protrusion 7b. As the patient moves his mandible in laterotrusion to the right from CR, only the right protrusion 7a may be in contact with the maxillary aspect 1-1-C of the guidance package 4-C.

Within the full range of motion of the TMJs 9R and 9L of the mandible 8-1, both protrusions 7a and 7b of the mandibular guidance component 1-2-C of the guidance package 4-C may be in contact in CR with the maxillary guidance component 1-1-C of the guidance package 4-C at points 2a and 2b or long centric area 3', or one or both protrusions 7a or 7b may be in contact with an inclined plane, lateral guidance 5, which locate on the lateral aspects of the inclined plane, or protrusive guidance 6, which locates on the anterior aspect of the inclined plane, of the maxillary component 1-1-C of the guidance package 4-C to provide appropriate anterior "canine" guidance to avoid posterior interferences, eliminate engrams, reduce the force of the muscles of mastication, and to allow freedom to the condyles 8-R and 8-L of the TMJ's 9-R and 9-L to be in their best stress bearing positions regardless the patient's individual occlusion or malocclusion.

The steepness, depth, and relative locations of the protrusions 7a and 7b of the mandibular component 1-2-C of the guidance package 4-C can be controlled to provide anterior stops and guidance to the mandible for a very wide range of treatment goals the dental professional may have in mind.

In some embodiments, the guidance package 4-C may be produced and/or applied with a minimal vertical dimension 16 penalty, for example, less than 5 mm, when the patient is at rest because the elimination of posterior interferences is accomplished with 3D guidance displacing the mandible inferiorly in excursions from CR. An excursion would be a movement of the mandible left, right or protrusively from the hinge axis of CR or long centric.

From the hinge axis of CR, or another point or axis of the dental professional's choosing, the 3D guidance of FIGS. 1, 4, 9, 10, 11A, 12A, 12B, 13A and 13B of the guidance packages may provide anterior guidance and eliminate the interferences of all excursions to the full border limits of the mandible. And furthermore, the guidance of the guidance package may be placed anterior to the anterior teeth so the physical material for that guidance (e.g., the guidance package) is not developed on a retentive piece at a position in between maxillary and mandibular anterior teeth, but rather independent of the position of anterior teeth and could be anterior (or posterior) to anterior teeth.

The guidance package 4-C can be attached to the retentive pieces up-side down and with proper rotation of the guidance package 4-C. In other words, the maxillary guidance component of the guidance package 1-1-C can be attached to a mandibular retentive piece and the mandibular guidance component of the guidance package 1-2-C is attached to a maxillary retentive piece, such that the guidance package 4-C can be used interchangeably with the maxillary and mandibular retentive pieces.

Figure 10:
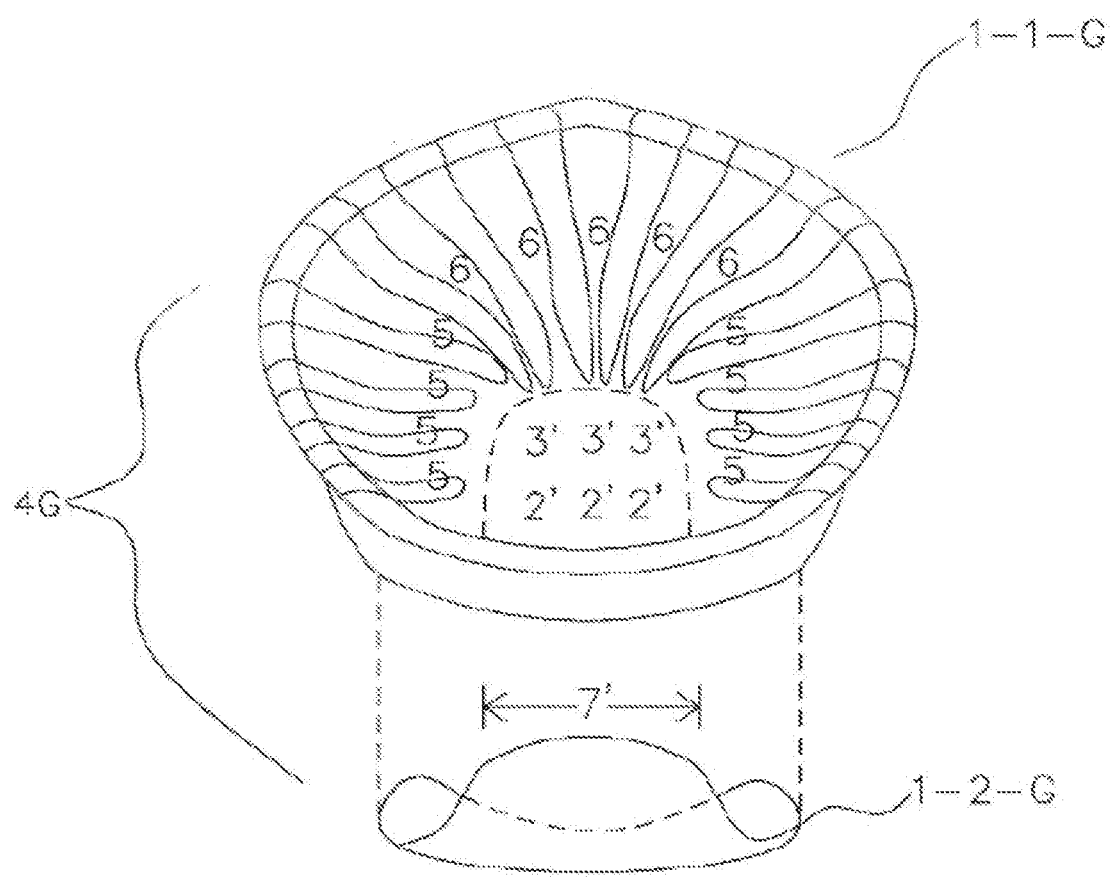
FIG. 10 is a planar perspective view of a "group function" guidance package for a patient with bruxism or other condition in accordance with an example embodiment.
Figure 10:
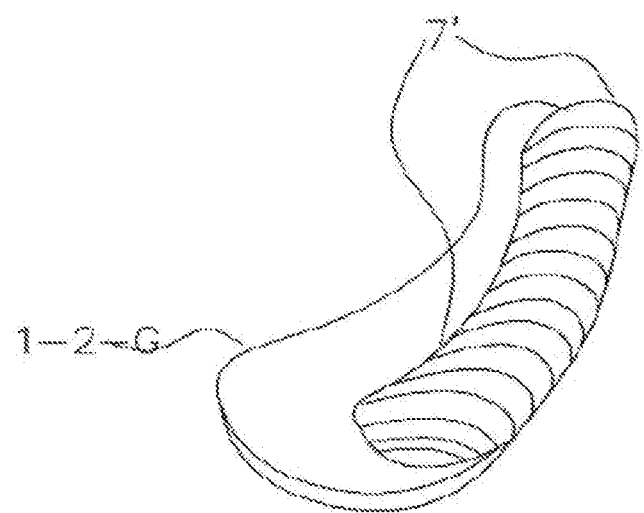

FIG. 10 provides another example design of a different guidance package 4, a "group function" guidance package 4-G (e.g., a bruxism, TMD or otherwise restorative guidance package), that may be created for a different version of a bruxism appliance. There may be a very broad protrusion 7' on the mandibular guidance component 1-2-G of the guidance component 4-G that would mimic group function from canine to canine, or premolar to premolar (or other teeth selected by the dental professional) in a way that would mimic ideal human group function anterior guidance. The broadness of protrusion 7' can be accentuated anterior-posteriorly and/or laterally to give freedom to the mandible or set limits to the mandible according to the treatment goals of the operator. The "group function" guidance package 4-G may be particularly suited for patients whose particular interferences (e.g., malocclusions) can be more efficiently neutralized by anterior guidance that is broad from the left anterior lateral pole to the right anterior lateral pole of the mandibular guidance component of the guidance package 4-G, as compared to a single pointed protrusion 7 of the mandibular guidance component 1-2 of FIG. 3, when a patient wears the appliance 13 and bruxes.

The maxillary component 1-1-G of the guidance package 4-G may be modified according to group function guidance when the patient bruxes. The mandibular component 1-2-G of the guidance package 4-G may be modified according to group function guidance when the patient bruxes. In some embodiments, the maxillary guidance component 1-1-G of the guidance package 4-G may have a concave inner surface with a cross-sectional shape in a horizontal plane forming a superellipse or arch form with convex outer sides. In other embodiments, the maxillary guidance component 1-1-G may take on any shape configured to mate with the mandibular guidance component 1-2-G. The size of the maxillary component 1-1-G may be, for example, less than 50 mm by 50 mm dependent upon the full range of motion and border limits of the mandible both horizontally and vertically for a particular patient.

There may be a broad area of CR stop 2' that is broader in contrast to a CR stop 2 of a maxillary guidance component that is coupled to a single pole protrusion 7 and locates on the posterior aspect of the flat area of the maxillary guidance component, and a broad area of long centric 3', which is broader in contrast to an area of long centric 3 in a maxillary guidance component that is coupled to a single pole protrusion 7' and locates on the anterior aspect of the flat area of the maxillary guidance component. The steepness 33 and depth 32, as shown in FIG. 1, of the areas of lateral and protrusive guidance on the maxillary component 1-1-G of the guidance package 4-G can be controlled or modified to provide anterior stops and guidance to the mandible for a very wide range of treatment goals that the dental professional may have in mind. Further, the steepness and depth of the protrusion 7' of the mandibular guidance component 1-2-G of the guidance package 4-G can be controlled to provide anterior stops and guidance to the mandible for a very wide range of treatment goals the dental professional may have in mind.

Within the full range of motion of the TMJ's 9-R and 9-L of the mandible 8-1, the broad protrusion 7' of the mandibular guidance component 1-2-G of the guidance package 4-G may be in contact in CR 2' with the maxillary guidance component 1-1-G of the guidance package 4-G or the long centric area 3', or a lateral aspect of the broad protrusion 7' may be in contact with an inclined plane, lateral guidance 5, which are located on both lateral aspects of the inclined plane, or protrusive guidance 6, which are located on the anterior aspect of the inclined plane of the maxillary guidance component 1-1-G of the guidance package 4-G to provide appropriate anterior "group function" guidance to avoid posterior interferences, eliminate engrams, reduce the force of the muscles of mastication, and to allow freedom to the condyles 8-R and 8-L of the TMJs 9-R and 9-L to be in their best stress bearing positions.

In some embodiments, the guidance package 4-G may allow for a minimal vertical dimension 16 penalty, for example, less than 5 mm, when the patient is at rest because the elimination of posterior interferences is accomplished with 3D guidance displacing the mandible inferiorly in excursions from CR and long centric. Further, the guidance of the guidance package 4-G may be placed anterior to the teeth so the physical material for that guidance is not in addition, but independent of and anterior to anterior teeth. This guidance can be provided no matter the condition or even presence of teeth and because the guidance may be placed anterior to the traditional limitations of guidance, there is increased advantage over the muscles of mastication in excursions as compared to any previous system.

The guidance package 4-G can be attached to the retentive pieces up-side down and with proper rotation of the guidance package 4-G. In other words, the maxillary aspect of the guidance package 1-1-G can be attached to a mandibular retentive piece and the mandibular aspect of the guidance package 1-2-G can be attached to a maxillary retentive piece, such that the guidance package 4-G can be used interchangeably with the maxillary and mandibular retentive pieces.

The three example bruxism (some types of TMD and restorative) guidance packages shown in FIGS. 1, 9 and 10, may provide a superior bruxism appliance to the vast majority of bruxism patients regardless their malocclusion. However, human occlusions and malocclusions are so diverse to each individual that it may not be practical to assign a particular guidance package 4 a particular occlusion or malocclusion or a particular malady like TMD. Selection of a particular guidance package 4 and possibly the modification of that guidance package 4 may require an informed decision by the dental professional using clinical judgment for a particular situation or a combination of malocclusions and maladies.

In addition to the most common use of the guidance packages 4 shown in FIGS. 1, 9, and 10, which is the treatment and amelioration of bruxism (some types of TMD, and restorative applications), guidance packages 4 of other designs or other guidance and stop profiles may be used to control and limit the mandible 3Dly independent of malocclusion or condition of the patient's teeth.

Used this way, the guidance package 4 may offer a wide range of solutions for other maladies of the mouth, jaws, TMJ, and sleep apnea. When using the guidance package 4, not only does the dental professional have 3D control of the mandible, but dependent upon the malady and treatment prescribed, the guidance package 4 can be indexed in a position of the mandible in relation to the maxilla of the dental professional's choosing other than CR to greatly expand the scope of treatments available. In some embodiments, the guidance package 4 may be indexed and attached to retentive pieces within the retentive piece system, not directly to teeth or the arch. With the use of a guidance package 4, the dental professional has a broad spectrum of 3D patterning available to guide the patient's mandible to a selected destination by a wide range of 3D routes. Thus, a dental professional may take advantage of a wide range of very different clinical applications of the guidance package 4. In some embodiments, the design of a guidance package 4 may reflect the dental professional's choice and prescription to apply very different guidance and limits to the mandible and/or to each TMJ 9-R and 9-L or other variables in the stomatognathic system independently.

In regard to TMD appliances, the goal in all these plethora of different occlusions and malocclusions in the context of TMD and various other damage profiles of the stomatognathic system with or without bruxism, is to provide specialized anterior guidance and limits to treat specific damage profiles of specific patients and to neutralize posterior interferences to eliminate destructive engrams associated with interferences to decrease muscle activity and spasticity, to give protection to the teeth and the TMJ, the reduction of myo-facial pain syndrome, and the reduction of migraine headache. In regard to sleep apnea, the goal is that as the patient closes or is closed to move the mandible protrusively, and therefore the tongue forward, to increase the volume of the airway space.

Figure 11A:
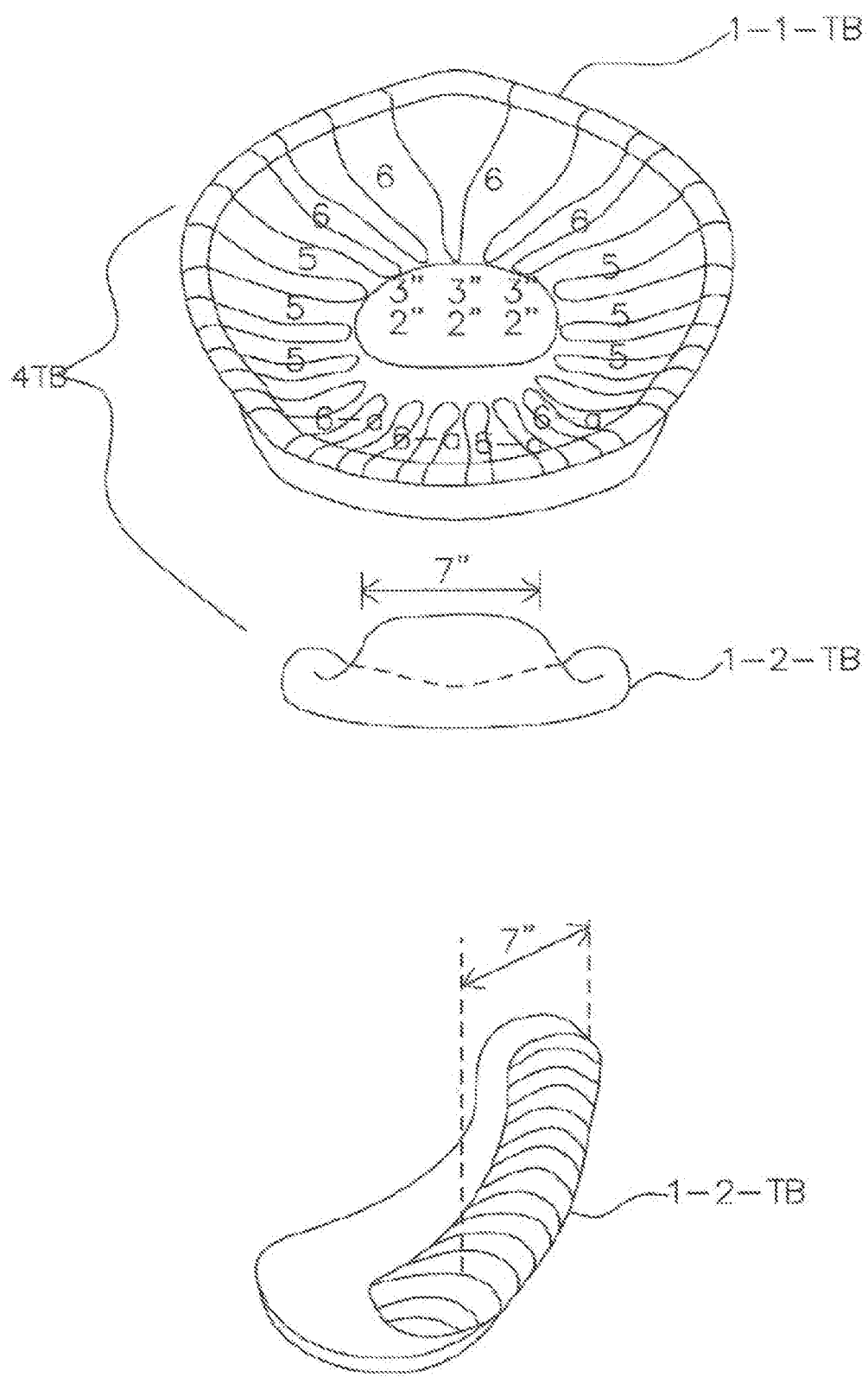
FIG. 11A is a planar perspective view of a "bilateral anterior repositioning" guidance package for a patient with TMD or a sleep apnea patient in accordance with an example embodiment.

FIG. 11A shows an example embodiment of a different guidance package 4, a TMD or sleep apnea guidance package, a "bilateral anterior repositioning" guidance package 4-TB to enable a dental professional to make an anterior repositioning appliance to treat bilateral anterior disc displacement of the TMJs. Again, a very different clinical application of the guidance package 4 and a further example of the flexibility of treatments the guidance package 4 can provide to a dental professional with its ability to provide 3D control of the front end of the mandible. To treat bilateral disc displacement of the TMJs, both the mandibular guidance component of the guidance package 1-2-TB and a maxillary guidance component of the guidance package 1-1-TB can be indexed so that as the patient closes his mandible 8-1, the mandible can be guided forward and vertically to the designated position of rest 2" customized to treat the patient's damage in which both the condyles 8-R and 8-L of the TMJs 9-R and 9-L recapture both the discs bilaterally.

The maxillary guidance component of the guidance package 1-1-TB may have a customized protrusive guidance 6a located on the posterior aspect of the maxillary guidance component 1-1-TB (where otherwise the posterior aspect of the maxillary guidance component 1-1 shown as position 2 and 2' in FIGS. 2 and 10, respectively of a bruxism guidance package would be to guide the mandible back to CR), to guide the mandible protrusively and vertically to this therapeutic position of rest 2". The position of rest or predetermined index position (prescribed maximum closure position) 2" may be designated or indexed based on the damage of each patient.

From this designated position of rest 2" that has recaptured both discs of the TMJs, the 3D guidance for the mandible to long centric area 3", on the anterior aspect of the flat area, and then further to lateral guidance 5, and protrusive guidance 6, may provide symmetrical protection and therapy for the particular damage or malady each patient exhibits, elimination of posterior interferences, elimination of engrams, and the reduction of the forces of the muscles of mastication in excursions. The lateral guidance 5 may be positioned on both lateral aspects of the inclined plane of the maxillary guidance component. The protrusive guidance may be positioned on the anterior aspect of the inclined plane of the maxillary guidance component. The maxillary component 1-1-TB of the guidance package 4-TB may be modified according to the therapeutic situation or other considerations. The mandibular component 1-2-TB of the guidance package 4-TB may be modified according to the therapeutic situation or other consideration.

In some embodiments, the guidance package 4-TB may provide a minimal vertical dimension 16 penalty when the patient is at rest because the anterior repositioning of the condyles 8-R and 8-L and the elimination of posterior interferences may be accomplished with 3D guidance displacing the mandible 8-1 vertically in the therapeutic movement to reposition the condyles 8-R and 8-L and the excursions from this designated position 2". Further, the guidance of the guidance package 4-TB may be placed anterior to the teeth so the physical material for that guidance is not in addition, but independent of and anterior to anterior teeth.

This guidance can be provided no matter the condition or even presence of teeth and because the guidance may be placed anterior to the traditional limitations of guidance where there is increased advantage over the muscles of mastication in excursions as compared to any previous system.

The guidance package 4-TB can be attached to the retentive pieces up-side down and with proper rotation of the guidance package 4-TB. In other words, the maxillary guidance component of the guidance package 1-1-TB can be attached to a mandibular retentive piece and the mandibular guidance component 1-2-TB can be attached to a maxillary retentive piece, such that the guidance package 4-TB can be used interchangeably with the maxillary and mandibular retentive pieces.

As with any guidance package 4, a series of guidance package derived appliances could be designed by the dental professional to gently "walk back" the condyles to CR as the posterior tissues are healed. For example, as the condyles heal and become positioned back further, the same guidance packages (or different guidance packages) can be indexed in a different place to progressively move the condyles. As with any guidance package construction 4 the steepness, depth, size and shape of both guidance components of the guidance package may be modified to meet the dental professional's goals and/or the damage and malocclusion profile of a particular patient.

To treat sleep apnea, both the mandibular guidance component of a guidance package 1-2-TB and a maxillary guidance component of the guidance package 1-1-TB can be indexed and/or modified so that as the patient closes his mandible 8-1, it can be guided forward and vertically to the designated position of rest (prescribed maximum closure position) 2" customized to move the mandible protrusively to about 50-70% of that patient's total protrusive potential. By moving the mandible to the clinically effective protrusive position, the tongue is also moved forward to open the patient's airway to treat the patient's sleep apnea. The maxillary guidance component of the guidance package 1-1-TB may have a customized protrusive guidance component 6a located on the posterior aspect of the maxillary component (where otherwise the posterior aspect of the maxillary guidance component 1-1, shown as position 2 and 2' in FIGS. 2 and 10, respectively, of a bruxism guidance package would be to guide the mandible into centric relation) to guide the mandible protrusively and vertically to this therapeutic position of rest 2' The position of rest 2" may be designated or indexed based on the distance that the mandible should be moved protrusively to effectively treat sleep apnea of each patient.

From this designated position of rest 2" that has adequately opened the airway, the 3D guidance for the mandible to long centric area 3", on the anterior aspect of the flat area, and then further to the lateral guidance 5, and protrusive guidance 6, may provide symmetrical guidance, eliminate posterior interferences, eliminate engrams, and reduce forces of the muscles of mastication in excursions. The lateral guidance 5 may be positioned on both lateral aspects of the inclined plane of the maxillary guidance component 1-1-TB. The protrusive guidance 6 may be positioned on the anterior aspect of the inclined plane of the maxillary guidance component 1-1-TB. The maxillary component 1-1-TB of the guidance package 4-TB may be modified according to the therapeutic situation or other consideration. The mandibular component 1-2-TB of the guidance package 4-TB may be modified according to the therapeutic situation or other consideration.

In some embodiments, the guidance package 4-TB may provide a minimal vertical dimension 16 penalty when the patient is at rest because the anterior repositioning of the mandible and the elimination of posterior interferences may be accomplished with 3D guidance displacing the mandible 8-1 vertically in the therapeutic movement to anteriorly reposition the mandible 8-1 for airway opening and the excursions from this designated position 2". Further, the guidance of the guidance package 4-TB may be placed anterior to the teeth so the physical material for that guidance is not in addition to, but independent of and anterior to, the anterior teeth.

This guidance can be provided no matter the condition or even presence of teeth. Further, as the guidance may be placed anterior to the guidance of existing systems, it can provide increased advantage over the muscles of mastication in excursions.

In some embodiments, the guidance package 4-TB can be attached to the retentive pieces up-side down with proper rotation of the guidance package 4-TB. That is, the maxillary guidance component of the guidance package 1-1-TB can be attached to the mandibular retentive piece and the mandibular guidance component of the guidance package 1-2-TB can be attached to the maxillary retentive piece such that the guidance package 4-TB can be used interchangeably with the maxillary and mandibular retentive pieces.

Figure 12A:
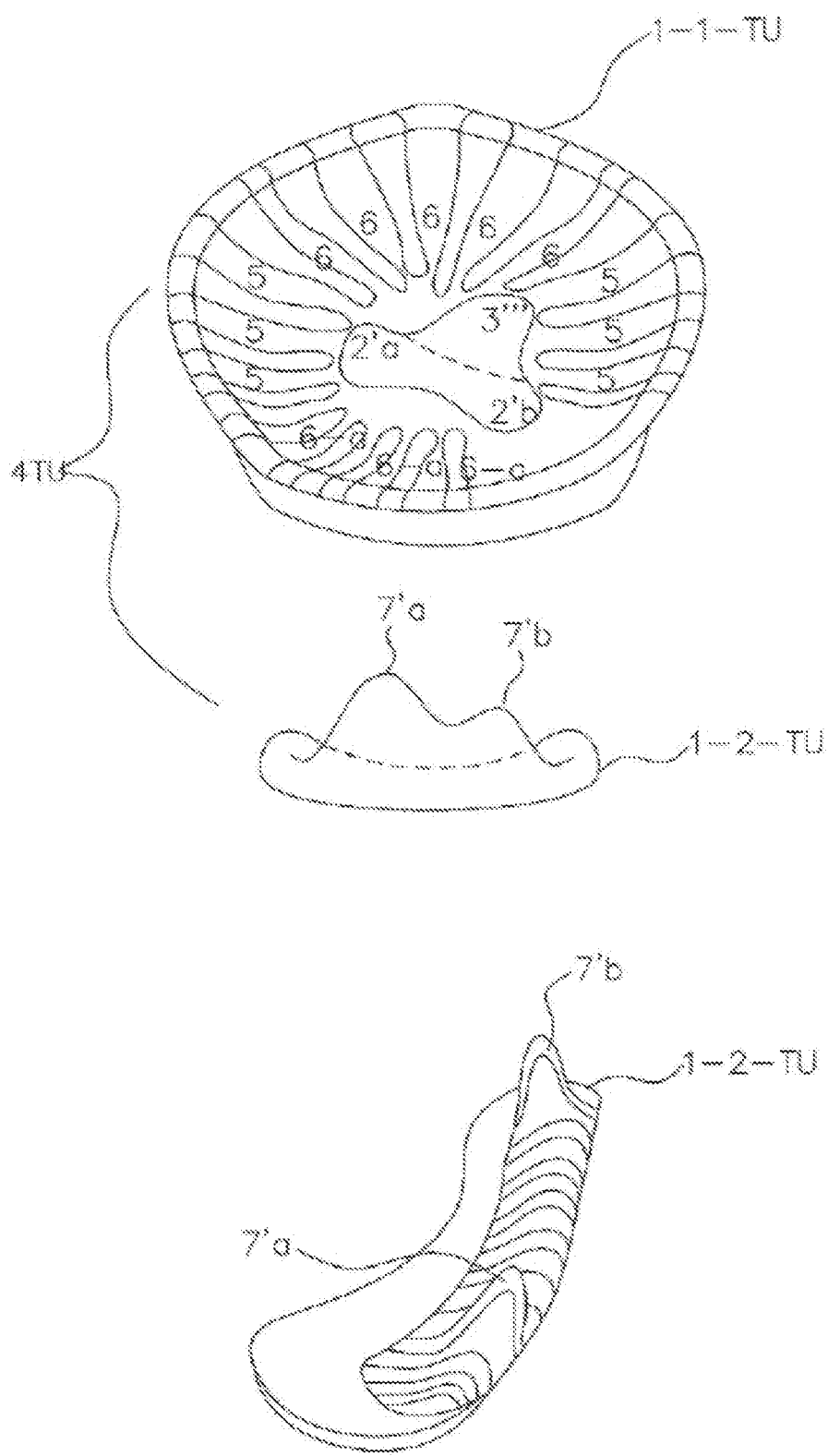
FIG. 12A is a planar perspective view of an "asymmetric protrusive" guidance package for a patient who has a damaged disc within the left TMJ in accordance with an example embodiment.

FIG. 12A shows another example embodiment of a guidance package 4, a TMD treatment guidance package, an "asymmetric protrusive" guidance package 4-TU to enable a dental professional to create a TMD treatment appliance that can be selective and differential to each TMJ 9-R and 9-L or other unilateral maladies of the mandible 8-1, or supporting structures. Again, this is another example of a very different clinical application, taking advantage of the robust flexibility of the guidance package 4.

In this example embodiment, the patient has an anteriorly displaced meniscus in the right TMJ 9-R, and the left TMJ 9-L is normal. The dental professional may prescribe a guidance package 4TU that anteriorly repositions the right condyle 8-R to recapture the displaced meniscus, but allows the left condyle 8-L to be in CR.

On the mandibular aspect of the guidance package 1-2-TU there may be two protrusions 7'a and 7'b in which the protrusion on the right 7'a is taller and steeper than the protrusion on the left 7'b. The maxillary aspect 1-1-TU of the guidance package 4-TU may be modified accordingly. The maxillary component 1-1-TU of the guidance package 4-TU may have a concave inner surface with a cross-sectional shape in a horizontal plane forming a superellipse or arch form with convex outer sides. In other embodiments, the maxillary component 1-1-TU may take on any shape configured to mate with the mandibular guidance component 1-2-TU. The size of the maxillary component 1-1-TU may be, for example, less than 50 mm by 50 mm dependent upon the full range of motion and border limits of the mandible both horizontally and vertically for a particular patient. The right area of anterior repositioning 2'a, which recaptures the anteriorly displaced disc of the right TMJ, may be located anteriorly and have a deeper indentation that is located anteriorly on the right aspect of the flat area of the maxillary guidance component, and may have customized anterior protrusive guidance 6a, posterior to the prescribed area of rest 2'a in contrast to the position of rest 2'b, which locates on the left posterior aspect of the flat area of the maxillary component, to enable the operator to anteriorly reposition the right condyle 8-R while allowing the left condyle 8-L to assume CR at rest. The maxillary component 1-1-TU of the guidance package 4-TU may be modified according to the therapeutic situation or other consideration. The mandibular component 1-2-TU of the guidance package 4-TU may be modified according to the therapeutic situation or other consideration.

In this example embodiment, as the patient closes his mandible 8-1, the right condyle 8-R may be guided anteriorly and vertically by the broader and taller right protrusion 7'a of the mandibular guidance component 1-2-TU of the guidance package 4-TU into the deeper and broader area 2'a of the maxillary guidance component 1-1-TU of the guidance package 4-TU to recapture the displaced disc of the right TMJ 9-R.

The left condyle 8-L of the left TMJ 9-L may be guided into its CR or a different designated position by the left protrusion 7'b of the mandibular guidance component 1-2-TU of the guidance package 4-TU into the CR position 2'b of the maxillary guidance component 1-1-TU of the guidance package 4-TU.

From this therapeutically designated position of rest (prescribed maximum closure position) 2'a and 2'b, based on the patient's damage profile, which has recaptured the right disc of the right TMJ 9-R, the 3D guidance to long centric rest 3''' and then further to lateral guidance 5, and protrusive guidance 6, may provide asymmetrical protection and therapy for the particular damage or malady this patient exhibits, elimination of posterior interferences, elimination of engrams, and the reduction of the forces of the muscles of mastication.

The guidance package 4-TU may provide a minimal vertical dimension 16 penalty when the patient is at rest because the anterior repositioning of the right condyle 8-R and the elimination of posterior interferences is accomplished with 3D guidance displacing the mandible 8-1 vertically in the therapeutic movement to reposition the right condyle 8-R and the excursions from this designated therapeutic position. Further, the guidance of the guidance package 4-TU may be placed anterior to the teeth so the physical material for that guidance is not in addition, but independent of and anterior to anterior teeth. This guidance may be provided no matter the condition or even presence of teeth and because the guidance may be placed anterior to the traditional limitations of guidance there can be increased advantage over the muscles of mastication in excursions as compared to any previous system.

The guidance package 4-TU can be attached to the retentive pieces up-side down and with proper rotation of the guidance package 4-TU. In other words, the maxillary guidance component of the guidance package 1-1-TU may be attached to a mandibular retentive piece and the mandibular guidance component of the guidance package 1-2-TU may be attached to a maxillary retentive piece, such that the guidance package 4-TU can be used interchangeably with the maxillary and mandibular retentive pieces.

Figure 12B:
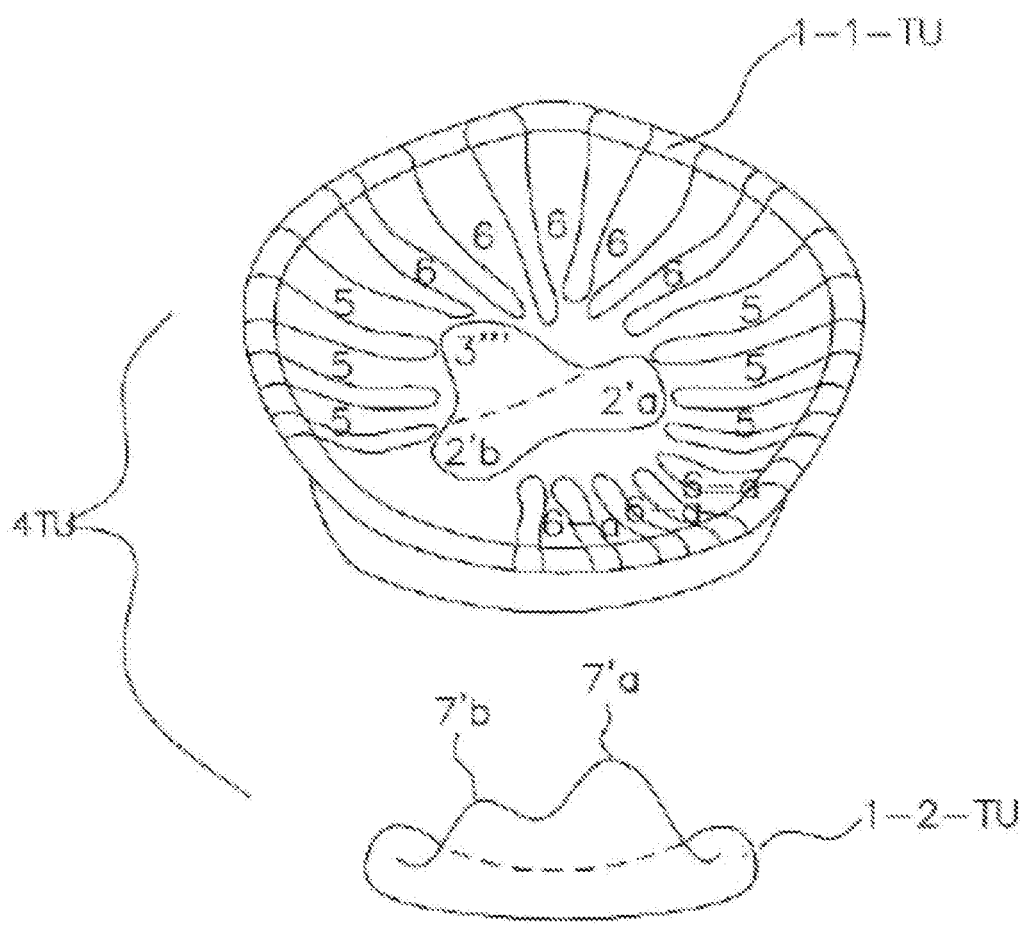
FIG. 12B is a planar perspective view of a "asymmetric protrusive" guidance package for a patient who has a damaged disc within the right TMJ in accordance with an example embodiment.
Figure 12B:
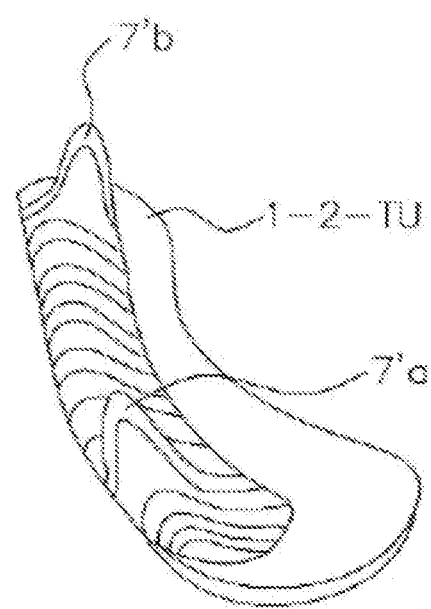

FIG. 12B shows the opposite configuration of FIG. 12A, in which the patient has an anteriorly displaced meniscus in the left TMJ 9-L, and the right TMJ 9-R is normal. The dental professional may prescribe a guidance package 4-TU that anteriorly repositions the left condyle 8-L to recapture the displaced meniscus, but allows the right condyle 8-R to be in CR.

On the mandibular guidance component of the guidance package 1-2-TU there may be two protrusions 7'a and 7'b in which the protrusion on the left 7'a is taller and steeper than the protrusion on the right 7'b. The maxillary guidance component 1-1-TU of the guidance package 4-TU may be modified accordingly. The maxillary component 1-1-TU of the guidance package 4-TU may have a concave inner surface with a cross-sectional shape in a horizontal plane forming a superellipse or arch form with convex outer sides. In other embodiments, the maxillary component 1-1-TU may take on any shape configured to mate with the mandibular guidance component 1-2-TU. The size of the maxillary component 1-1-TU may be, for example, less than 50 mm by 50 mm dependent upon the full range of motion and border limits of the mandible both horizontally and vertically for a particular patient. The left area of anterior repositioning 2'a, which recaptures the anteriorly displaced disc of the left TMJ, may be located anteriorly and have a deeper indentation than is located anteriorly on the right aspect of the flat area of the maxillary component, and have customized anterior protrusive guidance 6a, posterior to the prescribed area of rest 2'a in contrast to the position of rest 2'b, which locates on the right posterior aspect of the flat area of the maxillary component, to enable the operator to anteriorly reposition the left condyle 8-L while allowing the right condyle 8-R to assume CR or a different designated position at rest.

In this example embodiment, as the patient closes his mandible 8-1, the left condyle 8L may be guided anteriorly and vertically by the broader and taller left protrusion 7'a of the mandibular guidance component 1-2-TU of the guidance package 4-TU into the deeper and broader area 2'a of the maxillary aspect 1-1-TU of the AGP 4-TU to recapture the displaced disc of the left TMJ 9-L.

The right condyle 8-R of the right TMJ 9-R may be guided into its CR position or a different designated position by the right protrusion 7'b of the mandibular guidance component 1-2-TU of the guidance package 4-TU into the CR position 2'b of the maxillary guidance component 1-1-TU of the guidance package 4-TU.

From this therapeutically designated position of rest 2'a and 2'b, based on the patient's damage profile, which has recaptured the left disc of the left TMJ 9-L, the 3D guidance to long centric rest 3''' and then further to lateral guidance 5, and protrusive guidance 6, may provide asymmetrical protection and therapy for the particular damage or malady this patient exhibits, elimination of posterior interferences, elimination of engrams, and the reduction of the forces of the muscles of mastication.

The guidance package 4-TU may provide a minimal vertical dimension 16 penalty when the patient is at rest because the anterior repositioning of the left condyle 8-L and the elimination of posterior interferences is accomplished with 3D guidance displacing the mandible 8-1 vertically in the therapeutic movement to reposition the left condyle 8-L and the excursions from this designated therapeutic position. Further, the guidance of the guidance package 4-TU may be placed anterior to the teeth so the physical material for that guidance is not in addition, but independent of and anterior to anterior teeth. This guidance can be provided no matter the condition or even presence of teeth and because the guidance may be placed anterior to the traditional limitations of guidance there can be increased advantage over the muscles of mastication in excursions as compared to any previous system.

The guidance package 4-TU can be attached to the retentive pieces up-side down and with proper rotation of the guidance package 4-TU. In other words, the maxillary guidance component of the guidance package 1-1-TU may be attached to a mandibular retentive piece and the mandibular guidance component of the guidance package 1-2-TU may be attached to a maxillary retentive piece, such that the guidance package 4-TU can be used interchangeably with the maxillary and mandibular retentive pieces.

Figure 13A:
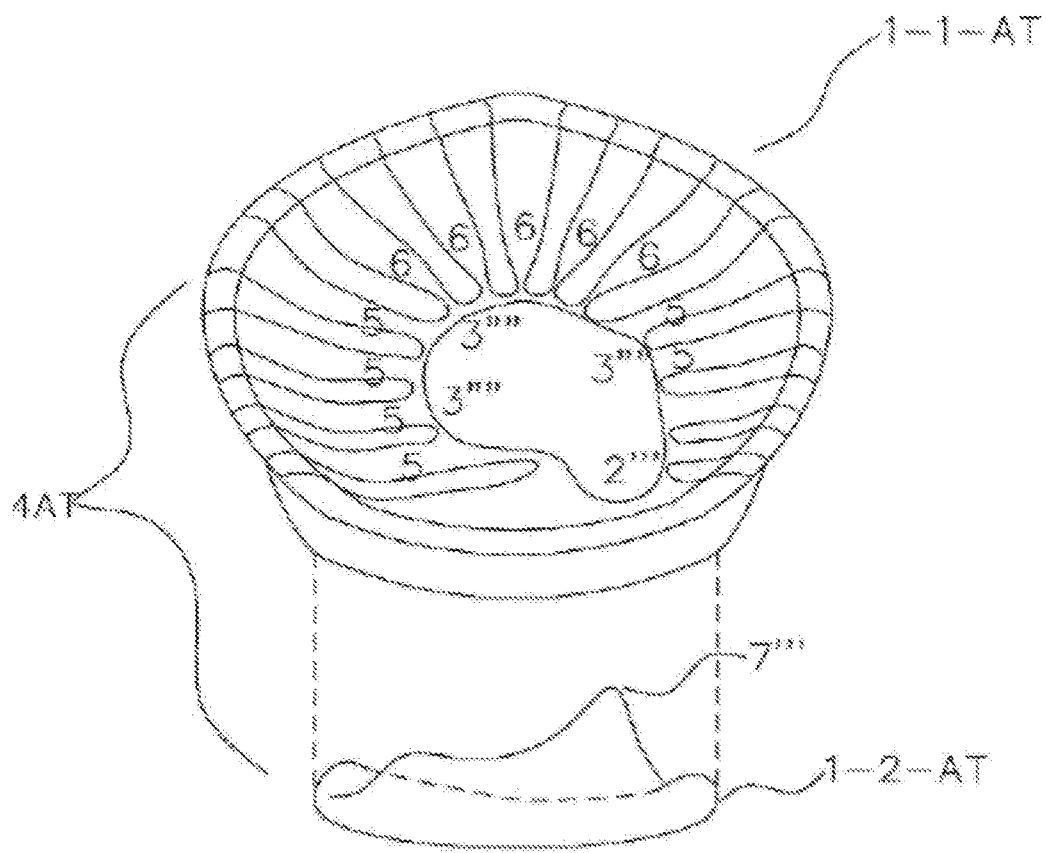
FIG. 13A is a planar perspective view of an "asymmetric" guidance package for a patient who has a damaged structure on the right side of the mandible in accordance with an example embodiment.
Figure 13A:
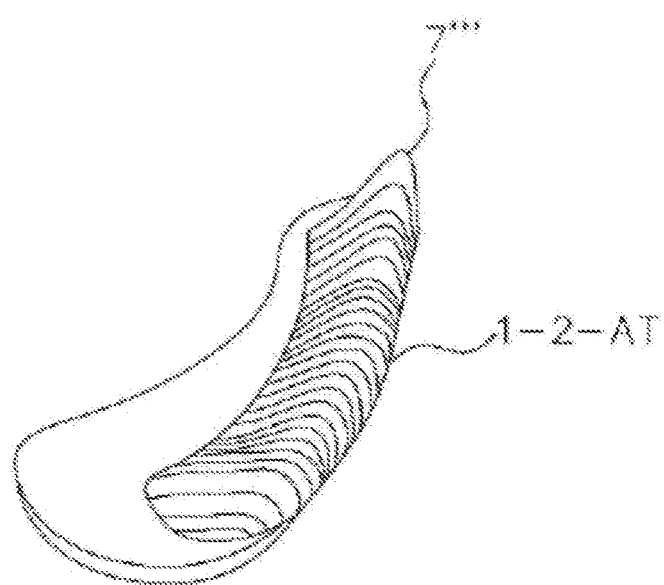
Figure 13B:
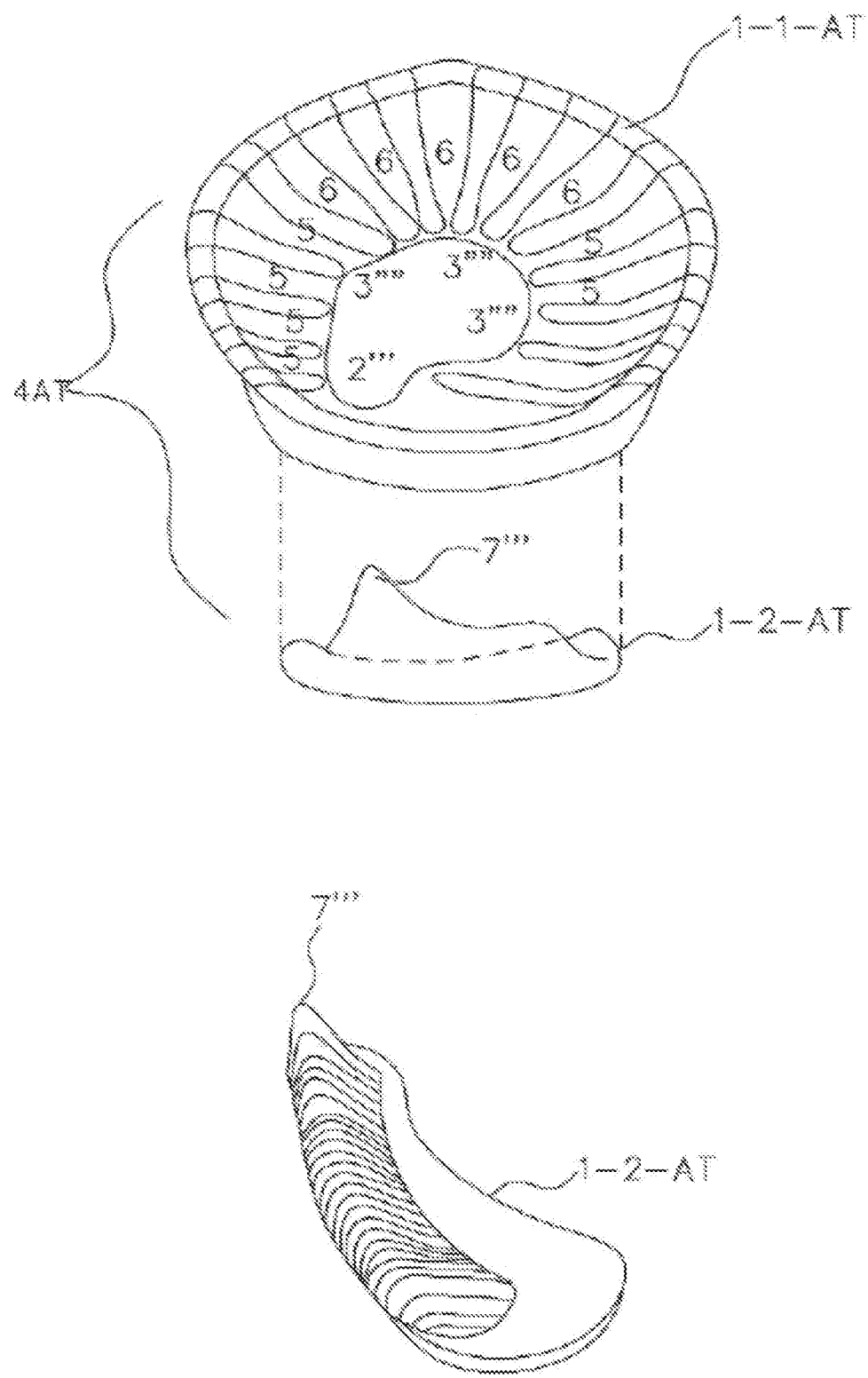
FIG. 13B is a planar perspective view of an "asymmetric" guidance package for a patient who has a damaged structure on the left side of the mandible in accordance with an example embodiment.

FIG. 13A and its mirror image FIG. 13B are two more example embodiments of a guidance package 4, a TMD treatment guidance package, an "asymmetric" guidance package 4-AT to enable a dental professional to treat a mandible that has had damage to one TMJ, or both TMJs, or the muscles, ligaments, or tendons of mastication unilaterally or bilaterally, or other clinical problems or combinations of clinical problems in which the operator needs the ability to control the movements and limits of the mandible in non-traditional 3D pathways symmetrically or asymmetrically. This is a very different clinical application of the guidance package 4. The design of this example guidance package 4-AT may reflect the dental professional's prescription to apply very different guidance and limits to each TMJ 9-R and 9-L or other variables in the stomatognathic system independently.

In this example, the protrusion 7''' may be located laterally to the midline. The asymmetrical depth and steepness of both the mandibular guidance component 1-2-AT and the maxillary guidance component 1-1-AT of the guidance package 4-AT can be controlled to provide anterior stops, limits and guidance for the treatment goals of the operator in this case asymmetrically providing very different parameters to each TMJ 9-R and 9-L. In this circumstance the patient's mandible 8-1 upon closing may be guided into a position of rest 2''', which is other than CR that is prescribed by the dental professional for each patient's particular malady or damage. From this designated position of rest (prescribed maximum closure position) 2''' the 3D guidance to long centric 3''' which has a customized shape, which is designed based on the damage of a specific patient on the anterior aspect of the flat area of the maxillary component, to provide guidance for this particular damage profile and then further to lateral guidance 5, and protrusive guidance 6, provided asymmetrically in this case, but could also be symmetrical protection and therapy for the particular damage or malady of a specific patient. The lateral guidance 5 may be positioned on both lateral aspects of the inclined plane of the maxillary guidance component. The protrusive guidance 6 may be positioned on the anterior aspect of the inclined plane of the maxillary guidance component. Both the maxillary and mandibular components 1-1-AT and 1-2-AT of the guidance package 4-AT may be modified according to the therapeutic situation or other consideration.

The guidance package 4-AT can be attached to the retentive pieces up-side down and with proper rotation of the guidance package 4-AT. In other words, the maxillary guidance component of the guidance component 1-1-AT may be attached to a mandibular retentive piece and the mandibular guidance component of the guidance package 1-2-AT may be attached to a maxillary retentive piece, such that the guidance package 4-AT can be used interchangeably with the maxillary and mandibular retentive pieces.

CAD-CAM Guidance Package Appliance

A CAD-CAM guidance package appliance could be custom produced by a dental professional in an unprecedented way providing solutions to a variety of conditions and or combinations of conditions and at a significant lesser expense to both the dental professional and the patient. The dental professional may have a broad spectrum of 3D patterning available to guide the patient's mandible to the chosen destination by a route among a broad spectrum of 3D routes.

Embodiments of the methods described herein can be applied to a wide range of stock guidance packages, and/or a stock guidance package that is then modified by the dental professional, and/or a custom designed guidance package for a specific patient. The guidance package chosen, chosen and modified, or designed could be one of many possibilities of size, shape or style to address a very wide range of problems or malocclusions. The maxillary guidance component and/or the mandibular guidance component of the guidance package can be chosen, chosen and modified, or designed to one among many choices of shape or size either individually or as a group to achieve whatever effect the operator desires. For instance, a TMD therapist may have available to her/him an unprecedented range of options regarding both limits and guidance to the mandible. In contrast to other systems, some embodiments of the disclosed guidance package 4 can provide 3D anterior guidance and limits to the mandible independent of the condition, position, presence or absence of teeth. Also uniquely attributable to the guidance package, the position of the guidance package (and therefore guidance and limits of the mandible within the guidance package retentive piece system) can be controlled to maximize or minimize different properties of the guidance package derived appliance to include increased or decreased mechanical advantage over the muscles of mastication in excursions. In some embodiments, the guidance package may be indexed and attached to retentive pieces within the retentive piece system, not directly to teeth or the arches. Considering the unprecedented choices, modification and design potential of the guidance package, and the flexibility regarding the position of the guidance package within the retentive piece system, the CAD-CAM guidance package appliance to include the CAD-CAM guidance package bruxism appliance, the CAD-CAM TMD appliance, and the CAD-CAM sleep apnea appliance are advantageous over existing night guards, TMD appliance systems, and sleep apnea appliance systems.

The CAD-CAM guidance package appliance may be a two-piece, customized, comfortable to wear, seamless, lightweight, minimal vertical dimension at rest in CR (or a different index position of the dental professional's choosing) appliance that provides 3D anterior guidance and limits.

In some embodiments, the guidance package may be placed or indexed (and therefore 3D guidance placed within a broad range transversely, sagittally, and frontally on the retentive piece system) anterior, posteriorly or laterally to the teeth and therefore not in between the teeth so the material which provides the guidance may not add any vertical height to the appliance to allow an appliance of minimal vertical dimension at rest. Further, because the guidance may be located even further anterior to the muscles of mastication than teeth, a guidance package equipped appliance may have inherent superior mechanical advantage over the muscles of mastication in excursions as compared to any guidance involving teeth or built on teeth. In some embodiments, the guidance package may be indexed and attached to retentive pieces within the retentive piece system, not directly to teeth or the arch. In contrast to existing night guards, TMD treatment systems, and sleep apnea treatment systems, the CAD-CAM guidance package appliance may have a broad range of 3D flexibility in the choice, modification and design of the anterior guidance and limits. Further, the CAD-CAM guidance package appliance to include bruxism, TMD and sleep apnea applications can be produced without regard to the condition, presence or absence of teeth, to include anterior teeth, because the guidance is provided entirely by the guidance package.

In the event the patient's CAD-CAM guidance package appliance is lost or destroyed, a digital record may exist to recreate a duplicate appliance quickly, without the need of a new record making appointment. A new CAD-CAM guidance package appliance replacement can be provided conveniently, and with cost savings for the patient.

The CAD-CAM guidance package appliance can be produced less expensively than traditional methods of the dentist and his lab manually producing and adjusting a splint. The CAD-CAM guidance package appliance is a superior appliance for addressing TMD issues, bruxism, and sleep apnea. The CAD-CAM guidance package appliance in contrast to all existing systems will provide a superior system to the patient, with greater convenience for the patient, and at a better price.

Embodiments of the disclosed methods for producing a customized guidance package equipped appliance may be more convenient, less expensive, and less work intensive for both the dental professional and the patient.

In one embodiment, a method of automatically producing or reproducing a customized guidance package equipped appliance involves combining digital methods and/or traditional methods converted to digital to collect and create information needed to automatically fabricate a specifically customized guidance package equipped appliance for a specific patient. When the patient needs a new guidance package equipped appliance due to loss or damage, because the digital record can be retained, a new guidance package equipped appliance can be provided without records being collected by the dental professional again.

After the dental and arch information, which is collected from a specific patient, and the guidance package appliance design is stored in a computer, a new guidance package equipped appliance could be produced by a Computer Numerical Control (CNC) lab, an in office 3D printer or other CAM enabled device, without any further work by the dentist or patient. Alternatively, if one or two variables regarding the patients' teeth or arch or movement parameters have changed, these could be changed in the computer records, the design changed accordingly and then sent to a CNC lab, 3D printer or other CAM enabled device, and a new guidance package equipped appliance could be produced without the necessity of a complete records collection session by the dentist and patient.

Procedure of Making a CAD-CAM Guidance Package Appliance

In one example embodiment, the procedure for the collection and creation of a patient's dental information record may include: gathering 3D information of both maxillary and mandibular arches; identifying an index position; setting the patient's virtual 3D maxillary and mandibular teeth and arch at the index position (e.g., CR) at an appropriate vertical dimension (e.g., providing enough space between teeth to provide clearance for guidance components (e.g., virtual retentive pieces and/or movement and stop profiles), or the point of rest, and if necessary, inputting the TMJ/condylar records into the virtual articulator; identifying the boundaries of an envelope region (3D region); defining movement parameters and, if necessary, performing collision (e.g., interference) detection to identify movement restrictions; identify a point in space (virtual point) to place the guidance package relative to the retentive pieces; optionally performing virtual functional simulation; optionally, virtually applying virtual shelves/protrusions to modify available surfaces for a final solution; designing one or more optional final solutions. The designed final solutions may be provided to a manufacturer (e.g., a CAD-CAM manufacturer) for production.

Gathering 3D information of the maxillary and mandibular teeth and arches, may involve using traditional methods (e.g., making impressions of the patients' teeth and arches and then pour in stone to make models and convert to digital by scanning the models) or directly recording the 3D information of the maxillary and mandibular teeth and arches with an in-office scanner or other data acquisition device.

Figure 14:
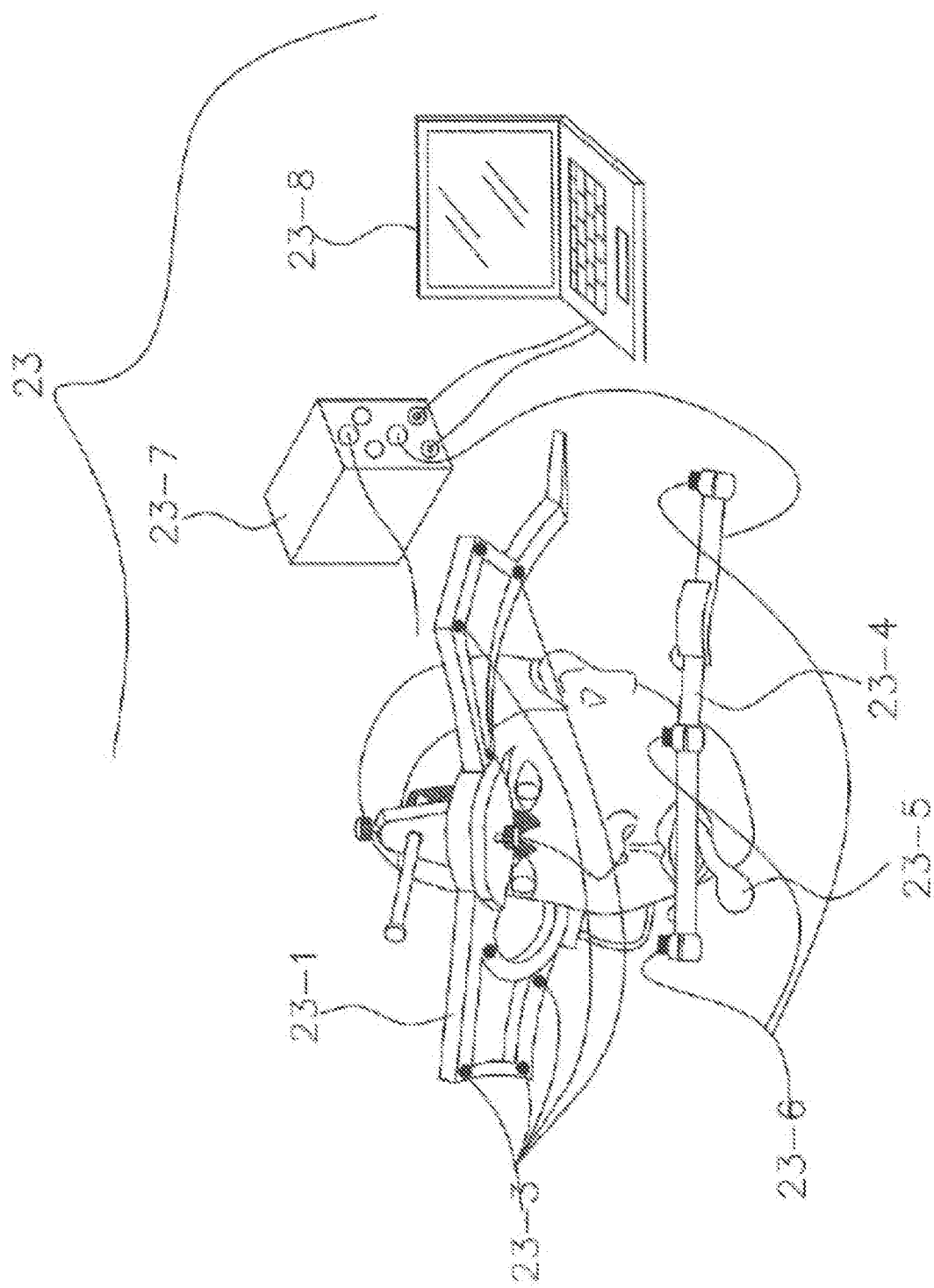
FIG. 14 is a perspective view of a Jaw Motion Analyzer for collecting TMJ and range of motion data from a patient and visualization of jaw movement of a patient in real time in accordance with an example embodiment.

Identifying the prescribed index position (maximum closure position) of the mandible in relation to the maxilla. For example, in a case of a dental professional intending to use a simple bruxism guidance package 4-S (e.g., as shown in FIGS. 2 to 4), or a "canine guidance" bruxism guidance package 4-C (e.g., as shown in FIG. 9) or a "group function" bruxism guidance package 4-G (e.g., as shown in FIG. 10), the dental professional may determine a CR position of the mandible at the appropriate vertical dimension as the index position, which may involve using traditional methods (e.g., by manipulating the mandible into CR hinge axis and closing the mandible to the appropriate vertical dimension). Other methods to identify the index position of the mandible to be therapeutic for bruxism include radiography, 3D radiography, sonography, MRI, JMA, and other methods of data collection. Next, the dental professional will make an index of that relationship of the teeth and arches (e.g., mounting the models of teeth and arches together in that relationship) and converting the relationship to digital by scanning the mounted models or directly recording the relationship of the maxillary and mandibular teeth and arches of the mandible in the index position. The dental professional may also use a combination of 3D radiography combined with intraoral scanning. The 3D radiography may be correlated or indexed with the intraoral scanning data and coincident to CR position of the mandible 8-1 at the appropriate vertical dimension as interpreted by the dental professional through 3D radiography, and that prescribed position of the teeth and arches may be recorded when the mandible is in CR directly using the correlated intraoral scanning data. In some cases, the index position may be determined or selected virtually. For a guidance package bruxism appliance, the dental professional may use average TMJ values or gather TMJ records using traditional methods and/or by using axiography and/or a Jaw Motion Analyzer, as shown in FIG. 14. These records may include, but are not limited to, facebow transfer, inter-condylar distance, condylary inclination, Bennet angle and border limits (range of motion). FIG. 14 shows an example Jaw Motion Analyzer system 23, which enables the collection of these data and visualization of jaw movement of a patient in real time. It may include an upper receiver 23-1 that is mounted on the upper face defining parameters to include the locations of the TMJs of a patient, and may be equipped with paramagnetic sensors 23-3. This unit may also include a lower receiver 23-4 that is mounted on the lower jaw of a patient, connected to the mandibular teeth of the patient via a metal splint 23-5 and another set of paramagnetic sensors 23-6 thereon, a converter 23-7 that converts the signal from the sensors 23-3, 23-6 to a computer 23-8. In the circumstance of TMD guidance package (e.g., as shown in FIGS. 11A, 12A, 12B, 13A and 13B) appliance, additional records may be collected regarding the damage profile of that patient to include radiography, 3D radiography, MRI, sonography, JMA or collection of TMJ records in a traditional way with a manual articulator combined with clinical observation of the pain and damage profile, and/or other methods.

As another example, in the case of a TMD guidance package appliance, the dental professional may establish the appropriate position of rest (prescribed maximum closure position) by one or more methods. For example, the dental professional can manually manipulate the patient's mandible as a part of his direct clinical evaluation establishing the appropriate position of rest (prescribed maximum closure position) when the mandible is closed, through communicating directly with the patient and clinical judgment. The dental professional may then record the relative relationship of the mandible to the maxilla at that position of rest (prescribed maximum closure position) by scanning the models of the teeth and arches that have been made from the patient in that position or directly record that relationship between maxillary and mandibular teeth and arches in that position with an in-office scanner. The dental professional may also use a combination of 3D radiography combined with intraoral scanning. The 3D radiography may be correlated or indexed with the intraoral scanning data. The dental professional may interpret through 3D radiography the damage profile of that patient to include the therapeutic position of rest (prescribed maximum closure position). The dental professional may record that relative relationship of the mandible to the maxilla at that position of first contact of the teeth at rest using the correlated intraoral scanning data. Some types of TMJ and stomatognathic damage may be recorded with alternative imaging such as MRI (Magnetic Resonance Image), sonography, and/or a Jaw Motion Analyzer (JMA). The alternative imaging and data collection may be combined with traditional methods of making indexed models of patients' teeth in the designated position of rest (prescribed maximum closure position) and then scanning or directly record that position with an in-office scanner.

As another example, in the case of a bilateral anterior disc displacement in which the dental professional intends to use a "bilateral anterior repositioning" TMD guidance package 4-TB, the dental professional may identify, for example, through manual manipulation of the mandible, direct communication with the patient, and clinical judgment, where the mandible (using the teeth and arches for indexing) should be indexed at rest (prescribed maximum closure position) to the maxilla (using teeth and arches for indexing), protrusively, laterally, and vertically to recapture the discs of both TMJs 9 R and L. The dental professional may advance the mandible protrusively enough from the CR position so that the condyles 8 R and L of the mandible 8-1 will recapture both the right and left discs within their respective TMJs 9 R and L. Other methods to identify the position of the mandible to be therapeutic include radiography, 3D radiography, sonography, MRI, JMA, and other methods of data collection.

In some cases, damage (e.g., anterior displacement) of the discs may be of equal distance anteriorly from their respective CR positions so that the recapture of the discs may require the same protrusive distance anterior from CR position of each respective condyle 8 R and L within each respective TMJ 9 R and L. Further, the damage (e.g., anterior displacement) of the discs may not be of equal distance anteriorly from their respective CR positions so that the recapture of the discs may require different protrusive distances when comparing the right condyle protrusively from CR position of the right TMJ to the left condyle protrusively from CR of the left TMJ.

If the protrusive value (e.g., distance) of the two condyles to recapture their respective discs is equal, there may not be any lateral movement of the mandible and the mid-sagittal plane of the mandible will remain coincident with the mid-sagittal plane of the maxilla.

If the right and left protrusive values (e.g., distances) of the two condyles to recapture their respective discs are different, then the lateral value of the rest position (prescribed maximum closure position) of the mandible may be either to the right or left of the mid-sagittal plane of the maxilla.

Figure 11B:
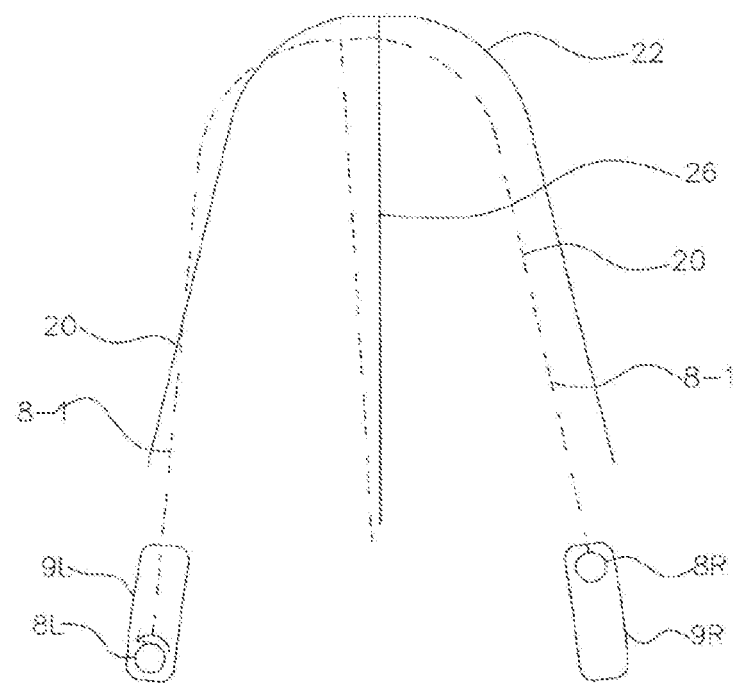
FIG. 11B is a schematic drawing of indexing the mandible left laterally to the maxilla in accordance with an example embodiment.
Figure 11C:
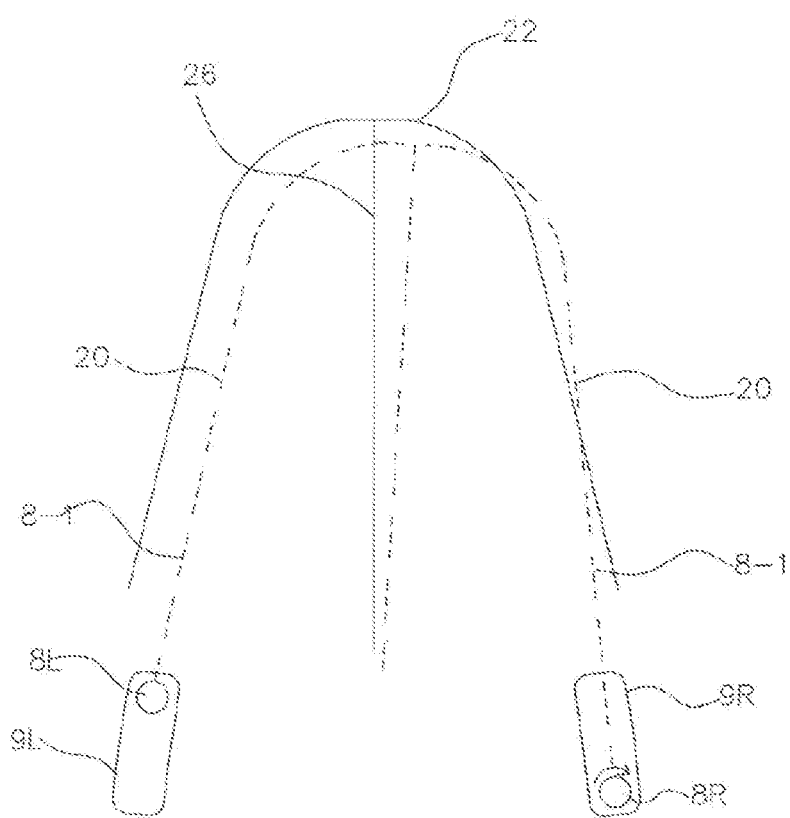
FIG. 11C is a schematic drawing of indexing the mandible right laterally to the maxilla in accordance with an example embodiment.

If the left condyle 8L must travel relatively further than the right condyle 8R protrusively to recapture its relative disc, then the lateral swing positioning of the mid-sagittal plane of the mandible may be located to the right of the mid-sagittal plane of the maxilla 26 proportionally to the relative differential distances traveled by the condyles to recapture their discs respectively bilaterally. FIG. 11C shows the example indexing of the mandible right laterally to the maxilla.

If the right condyle 8R must travel relatively further than the left condyle 8L protrusively to recapture its relative disc then the lateral swing positioning of the mid-sagittal plane of the mandible may be located to the left of the mid-sagittal plane of the maxilla 26 proportionally to the relative differential distances traveled by the respective condyles to recapture their discs bilaterally. FIG. 11B shows an example indexing of the mandible left laterally to the maxilla.

The vertical value may be the first contact (e.g., contact position of the worst interference) of teeth and arches for this protrusive and lateral position of the mandible already established to recapture the discs bilaterally to include a threshold distance if appropriate The dental professional can then record the relative relationship of the mandible to the maxilla at that position of rest (prescribed maximum closure position) using traditional methods discussed above or virtually. Some types of TMJ damage may be recorded with alternative imaging such as MRI, sonography, and/or a Jaw Motion Analyzer FIG. 14. Alternatively, the position of rest (prescribed maximum closure position) may be recorded using alternative imaging combined with traditional methods of making indexed models of patient's teeth in the designated position of rest and then scanning or directly record that position with an in-office scanner or other data acquisition device.

In the case of sleep apnea in which the dental professional intends to use a "bilateral anterior repositioning" guidance package 4-TB, the dental professional may identify through manual manipulation of the mandible, direct communication with the patient, and/or clinical judgment, where the mandible should be indexed at rest (prescribed maximum closure position; therapeutic for sleep apnea) to the maxilla (e.g., using teeth and arches for indexing), protrusively, laterally, and vertically to anteriorly (protrusively) relocate the mandible to get effective airway opening. The dental professional may use a George gauge, a Thornton Adjustable Positioner or Pro Gauge or other gauge, or other tools including radiography, 3D radiography, sonography, MRI, JMA, and other methods of data collection to identify the best therapeutic position of the mandible for sleep apnea. For a guidance package sleep apnea appliance, when the dental professional intends to use a "bilateral anterior repositioning" TMD guidance package, as shown in FIG. 11A, the dental professional may use average TMJ data or gather TMJ records for a particular patient using traditional methods and/or by using axiography and/or a Jaw Motion Analyzer, as shown in FIG. 14. These records may include, but are not limited to, facebow transfer, inter-condylar distance, condylary inclination, Bennet angle and border limits (range of motion).

The dental professional may advance the mandible symmetrically protrusively about 50 to 70% of the maximum protrusive potential of that patient from the CR position so that the mandible, and therefore the tongue, is relocated adequately forward to effectively open the airway.

The vertical value may be the first contact (e.g., contact position of the worst interference) of teeth and arches for this protrusive and lateral position of the mandible already established to open the airway effectively and could also include a threshold distance.

The dental professional can then record the relative relationship of the mandible to the maxilla at that position of rest (prescribed maximum closure position) using traditional methods of creating models of the patient's teeth in that position and convert to digital by scanning the mounted models or directly record the relationship of the maxillary and mandibular teeth and arches in that position of rest (prescribed maximum closure position) using an in office scanner or other data acquisition device In the case of a unilateral anterior disc displacement in which the operator intends to use a "asymmetric protrusive" TMD guidance package 4-TU (e.g., as shown in FIG. 12A and FIG. 12B), the dental professional may identify through manual manipulation of the mandible, direct communication with the patient, and clinical judgment, where the mandible should be at rest protrusively, laterally and vertically (3Dly) to recapture the disc of the damaged TMJ while leaving the other condyle (of the other TMJ) in a relatively normal albeit rotated position. Other methods to identify the position of the mandible to be therapeutic include radiography, 3D radiography, sonography, MRI, JMA, and other methods of data collection.

If the damaged disc (e.g., anteriorly displaced disc) is within the left TMJ, the dental professional may advance the mandible protrusively enough to advance the left condyle from the CR position to recapture that disc, while simultaneously swinging the mandible laterally to the right to allow the right condyle of the right TMJ to stay in its CR or rest position which will also rotate that condyle. Both the final right lateral swing position of the mandible, which will position the mid-sagittal plane of the mandible to the right of the mid-sagittal plane of the maxilla 26, and the rotation of the right condyle may be proportional to the distance traveled by the left condyle to recapture its disc, as shown in FIG. 11C.

If the damaged disc (e.g., anteriorly displaced disc) is within the right TMJ 9R, the dental professional may advance the mandible protrusively enough to advance the right condyle from its' CR position to recapture that disc, while simultaneously swinging the mandible laterally to the left to allow the left condyle 8L of the left TMJ 9L to stay in its CR or rest position which will also rotate that condyle. Both the final left lateral swing position of the mandible 8-1, which will position the mid-sagittal plane of the mandible to the left of the mid-sagittal plane of the maxilla 26, and the rotation of the left condyle 8L may be proportional to the distance traveled by the right condyle 8R to recapture its disc, as shown in FIG. 11B.

The vertical value may be the first contact (e.g., contact position of the worst interference) of teeth and arches for this protrusive and lateral position of the mandible that may include a threshold distance already established that will recapture the disc within the damaged TMJ and leave the other condyle within the undamaged TMJ in a relatively normal albeit rotated position.

The dental professional can then record that relative relationship of the mandible to the maxilla at that position of rest (prescribed maximum closure position) using traditional methods of creating models of the patient's teeth in that position and convert to digital by scanning the mounted models or directly record the relationship of the maxillary and mandibular teeth and arches in that position of rest using an in-office scanner.

The dental professional may also use a combination of 3D radiography combined with intraoral scanning. The 3D radiography may be correlated or indexed with the intraoral scanning data. The dental professional may interpret through 3D radiography and/or a Jaw Motion Analyzer FIG. 14 the damage profile of that patient to include where the mandible should be at rest protrusively, laterally and vertically (3Dly) in reference to the maxilla to recapture the disc of the damaged TMJ, while leaving the other condyle (of the other TMJ) in a relatively normal albeit rotated position. The dental professional may record that relative relationship of the mandible to the maxilla at that position of rest using the correlated intraoral scanning data. Some types of TMJ damage may be recorded with alternative imaging such as MRI and sonography. Alternatively, the position of rest (prescribed maximum closure position) may be recorded using alternative imaging combined with traditional methods of making indexed models of the patient's teeth in the designated position of rest (prescribed maximum closure position) and then scanning or directly record that position with an in-office scanner or another data acquisition device.

In the case of various other damage to the stomatognathic system in which the dental professional wants to protect or treat damage to any one or combination of other structures to include damage to a TMJ, or the muscles, ligaments, or tendons of mastication unilaterally, or other clinical problems in which the dental professional needs the ability to control the movements and limits of the front end of the mandible asymmetrically or symmetrically in nontraditional pathways and intends to use an "asymmetric" TMD guidance package, the dental professional may identify the best position of rest (prescribed maximum closure position) for the appropriate therapeutic treatment of the mandible, TMJ, or other stomatognathic malady of the mandible for that patient through manual manipulation of the mandible, direct communication with the patient, and clinical judgment, where the mandible should be at rest protrusively, laterally, and vertically (3Dly) to treat or protect a TMJ, or the muscles, ligaments, or tendons of mastication, or various other clinical problems or combinations of clinical problems. Other methods to identify the position of the mandible to be therapeutic include radiography, 3D radiography, sonography, MRI, JMA, and other methods of data collection.

In this example, as shown in FIG. 13A, the damaged structure is a damaged ligament on the right side of the mandible. The dental professional may advance the mandible protrusively enough to advance the right condyle 8R from the CR position to protect the damaged ligament, while simultaneously swinging the mandible laterally to the left to allow the left condyle 8L of the left TMJ 9L to stay in its CR position, which will also rotate that condyle. Both the final left lateral swing position of the mandible 8-1, which will position the mid-sagittal plane of the mandible to the left of the mid-sagittal plane of the maxilla 26 (as shown in FIG. 11B), and the rotation of the left condyle 8L may be proportional to the distance traveled by the right condyle 8R to protect the damaged ligament.

Another example situation for using an "asymmetric" TMD guidance package appliance may be to treat a damaged structure on either the left or right side of the stomatognathic system. In this example, there may be a damaged ligament lateral to the mid-sagittal plane of the mandible. The dental professional may position the mandible protrusively in a position to protect the damaged ligament. This may be an index position in which the mid-sagittal plane of the mandible is lateral to the mid-sagittal plane of the maxilla. The final lateral swing position of the mandible 8-1, which will position the mid-sagittal plane of the mandible to the right or left of the mid-sagittal plane of the maxilla 26 (as shown in FIG. 11B and FIG. 11C may be proportional to the relative distances traveled by each condyle to protect the damaged ligament. The vertical value may be the first contact that may include a threshold distance (e.g., contact position of the worst interference) of teeth and arches for this protrusive and lateral position of the mandible already established that will protect the damaged ligament. Other methods to identify the position of the mandible to be therapeutic to treat a damaged structure include radiography, 3D radiography, sonography, MRI, JMA, and other methods of data collection.

The dental professional can then record that relative relationship of the mandible to the maxilla at that position of rest (prescribed maximum closure position) using traditional methods of creating models of the patients' teeth in that position and convert to digital by scanning the mounted models or directly record the relationship of the maxillary and mandibular teeth and arches in that position of rest (prescribed maximum closure position) using an in-office scanner or another data acquisition device. Alternatively, 3D radiography with correlated intraoral scanning may be used to record position of rest (prescribed maximum closure position). The 3D radiography is correlated or indexed with the intraoral scanning data. The dental professional may interpret using 3D radiography the damage profile of that patient to include where the mandible should be at rest protrusively, laterally and vertically (3Dly) to protect the damaged mandibular structure. The dental professional may record that relative relationship of the maxilla to the mandible at that position of rest (prescribed maximum closure position) using the correlated intraoral scanning data. Some types of TMJ and stomatognathic damage may be recorded with alternative imaging such as MRI, sonography, and/or a Jaw Motion Analyzer. Alternatively, the position of rest (prescribed maximum closure position) may be recorded using alternative imaging combined with traditional methods of making indexed models of patient's teeth in the designated position of rest (prescribed maximum closure position) and then scanning or directly record that position with an in-office scanner.

Setting the patient's virtual 3D maxillary and mandibular teeth and arch in the index position (CR) at an appropriate vertical dimension data, or the point of rest (an example predetermined index position; a prescribed maximum closure position) may include the operator choosing data into the virtual articulator-CAD program, which may be already stored in a computer. The digital models of the patient's maxillary and mandibular teeth and arches may be virtually positioned on the Virtual Articulator 24 to set up a screen visualizing a Virtual Articulator 24 with patient's virtual models 25.

The TMJ/condylar records may be set in the virtual articulator-CAD program, with the records collected from the patient or use average measures. In the case of a TMD patient, additional TMJ data may be placed in the Virtual Articulator 24 regarding the damage or malady profile of that patient. This damage profile data may have been collected in the clinical exam, radiographic information, MRI, JMA or sonography. This additional information can be added to modify the movement parameters of the TMJs.

Identifying the boundaries of an envelope region (3D region) (e.g., virtually applying the maxillary retentive piece 27 and the mandibular retentive piece 28 to both arches of maxillary 22 and mandibular 20 at a determined thickness (e.g. 1 mm)). A 3D space may be defined as a global 3D region to include the space for the retentive pieces, the guidance package, and all other functions of the guidance package system (guides) or may be defined as a limited 3D region for manipulation of the guidance package only (e.g., in between the retentive pieces). The virtual retentive pieces 10 separately to maxillary arch 22 and mandibular arch 20 based on the Class of the malocclusion of the patient as shown in the FIGS. 6, 7 and 8. For a patient that does not have a severe malocclusion, Class I, retentive pieces 10 may be applied to both maxillary arch 22 and mandibular arch 20 as shown in FIG. 6.

Figure 15:
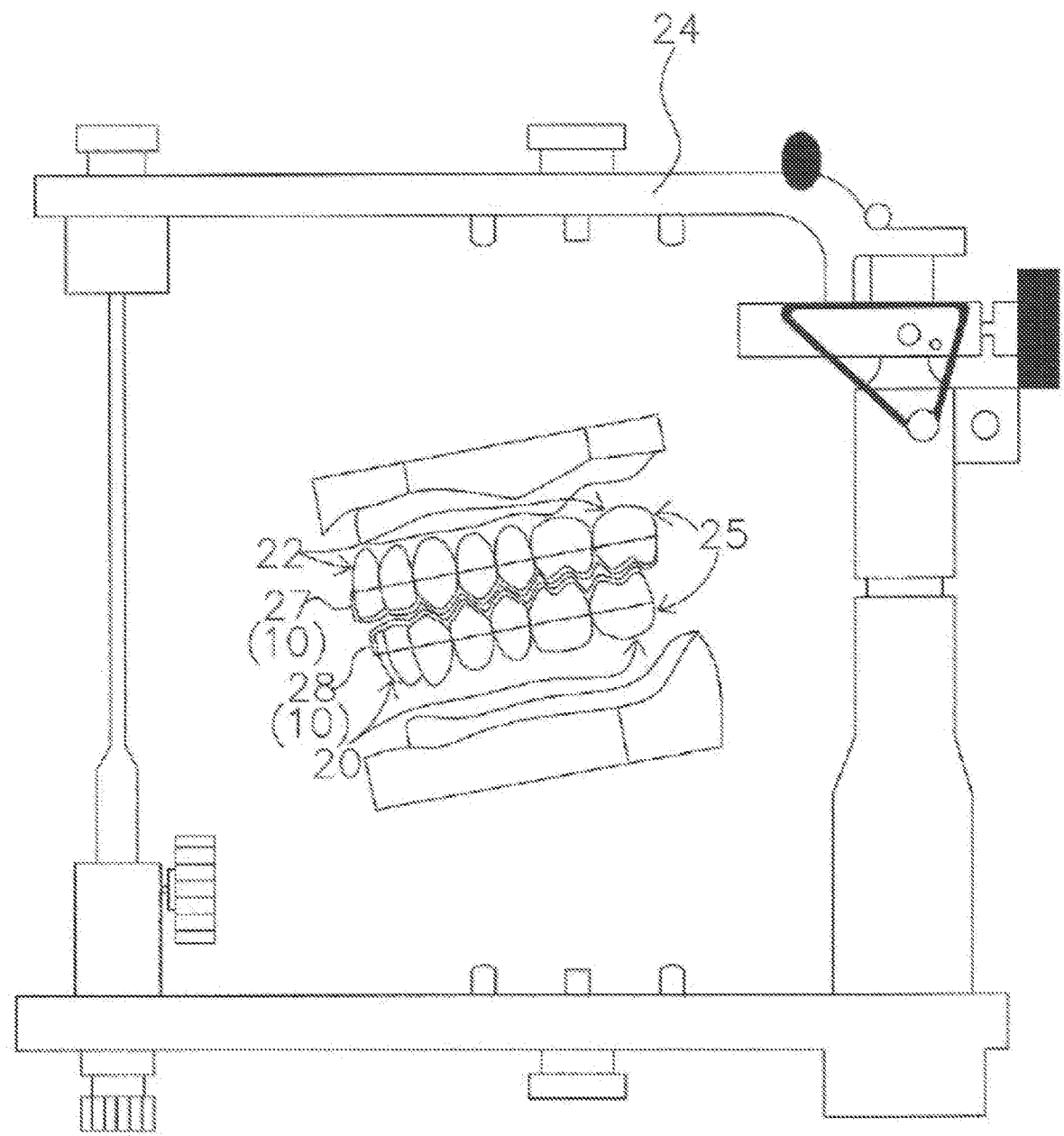
FIG. 15 depicts a virtual articulator when virtual models of a patient's teeth are set up based on the input data from a patient, who has a Class I occlusion, and have the virtual retentive pieces in place in accordance with an example embodiment.

FIG. 15 shows an example computer screen of a Virtual Articulator/CAD system 24 when virtual models 25 of the patient's teeth and arches are set up based on the input data from a patient, who has a Class I occlusion, which was collected from step I-a and b, and the virtual retentive pieces have been applied to the virtual models. In a case where virtual retentive pieces 27 and 28 are applied in the Virtual Articulator 24, the method may further include animating and measuring the jaw movements to include laterotrusion to all border limits of the mandible (full range of motion).

The method may further include defining movement parameters and performing collision (e.g., interference) detection in order to identify the movement restrictions. These movement restrictions, contact points and depths may be identified. For a TMD guidance package appliance. The additional TMJ data may alter the overall movement parameters, movement restrictions, contact points and depths.

Identifying a point in space (virtual point) to place the guidance package relative to the retentive pieces may be automated or operator determined. As the placement and orientation of the guidance package becomes more automated, the more likely subsequent adjustments to the guidance package will be necessary. Alternatively, the virtual point may be placed optimally 3Dly so that a guidance package may be used without modification or to minimize modification. (FIGS. 24-27). The virtual points (FIGS. 24-27) may represent one point for positioning of the guidance package or may represent a vector or three or more points for both positioning and orientating the guidance package.

Figure 16:
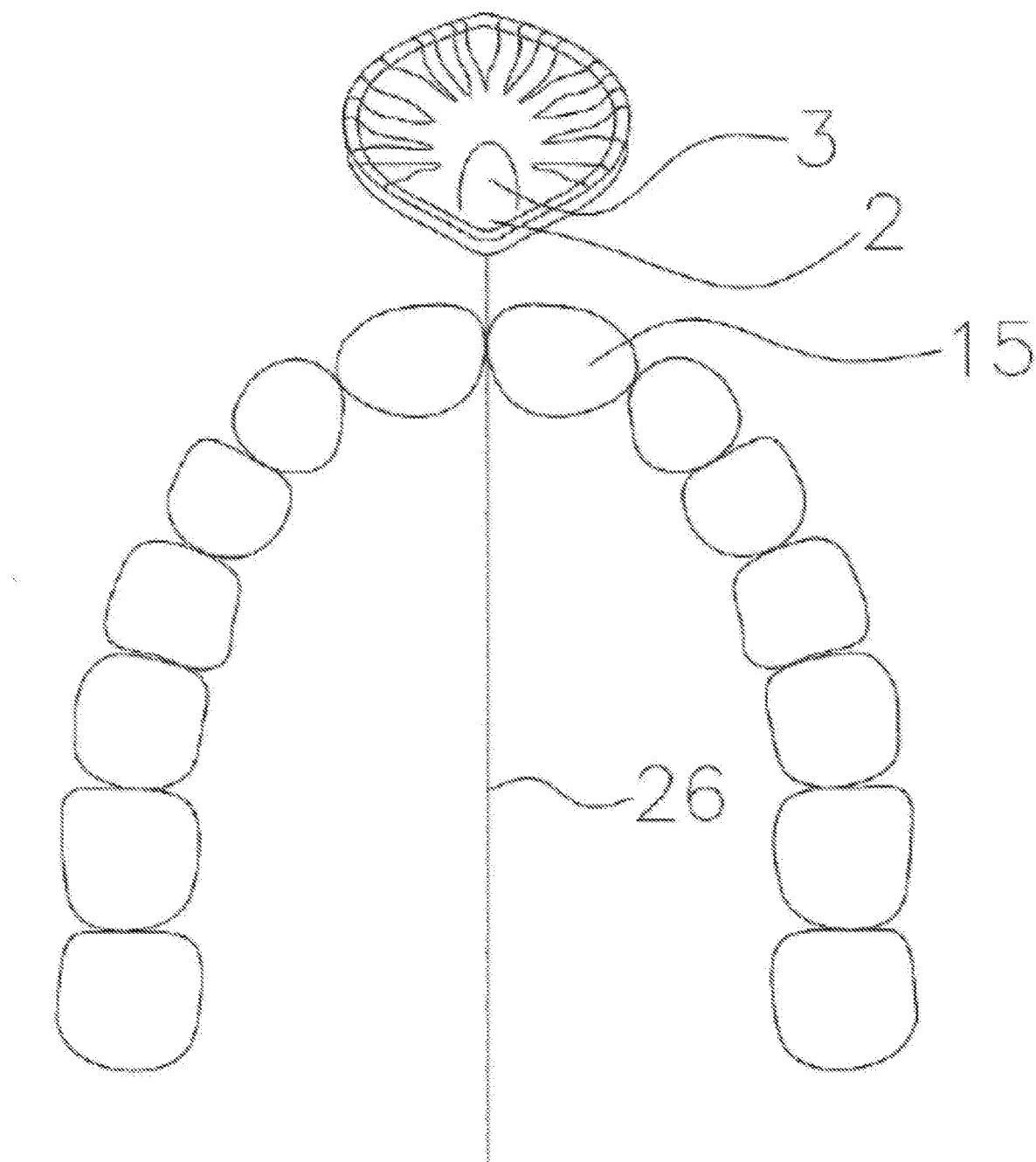
FIG. 16 is a conceptual drawing of the relative position of a guidance package (on a maxillary occlusal plane mid-sagittally) to the maxillary teeth set up in the virtual environment of a virtual articulator in accordance with an example embodiment.

In one embodiment, the virtual point(s) may be positioned at a specific distance (in some examples about 6 mm) anterior to the most anterior aspect of the maxillary retentive piece along the occlusal plane (a plane passing through the occlusal surfaces of the maxillary teeth) mid-sagittally 26). In some embodiments, the point in space may be between about 1 mm to about 10 mm anterior to the most anterior aspect of the maxillary retentive piece, depending on the size of the patient's stomatognathic system and the range of motion of the patient's mandible. In some embodiments, the virtual point may be placed optimally 3Dly so that a guidance package may be used without modification or to minimize modification. FIG. 16 shows the relative position of an example virtual guidance package 4 on a maxillary occlusal plane mid-sagittally 26.

Figure 17:
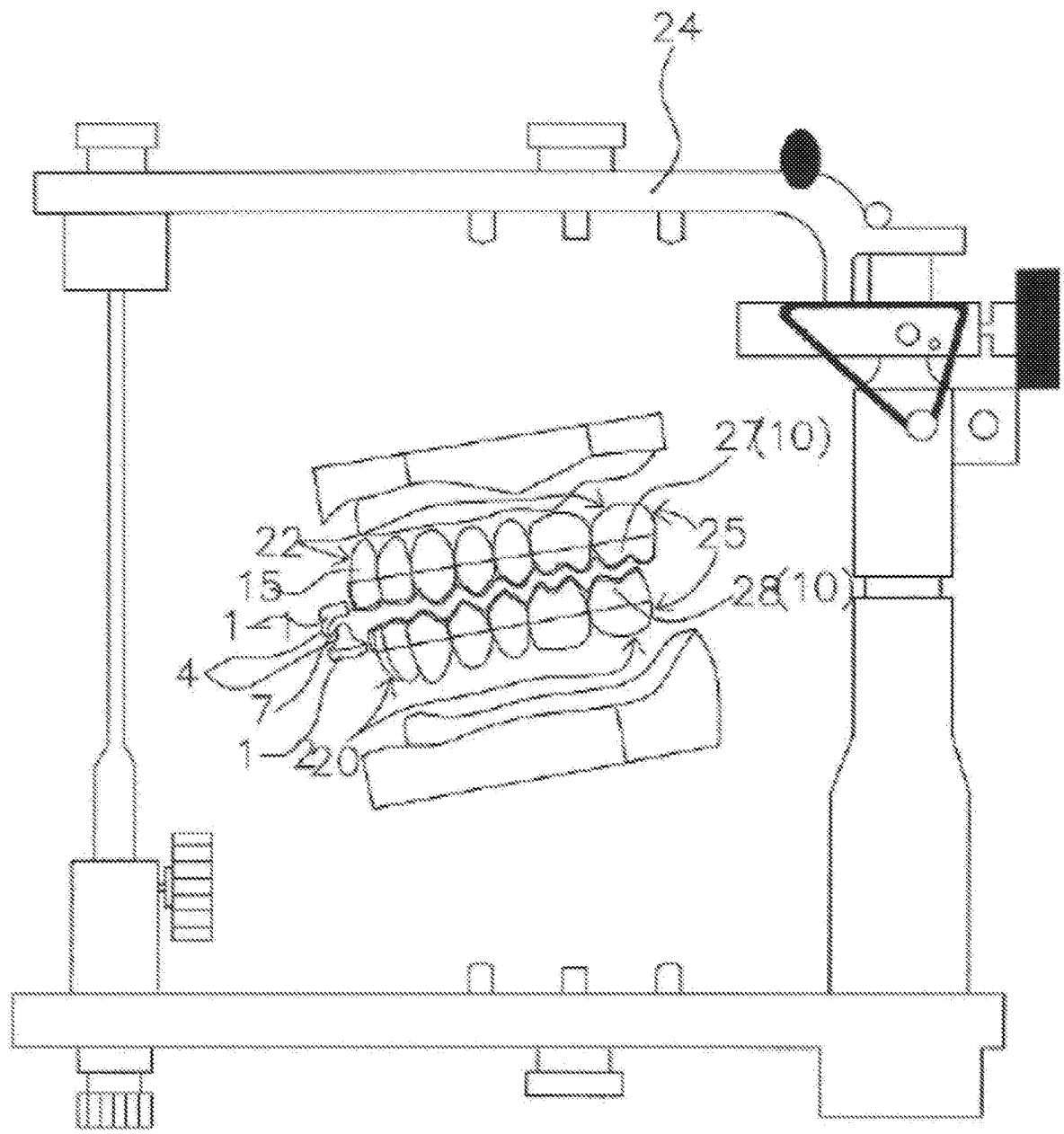
FIG. 17 is a virtual side view of the virtual guidance package placed relative to the virtual retentive pieces according to the relative position in FIG. 16 in the virtual environment of a virtual articulator in accordance with an example embodiment.

FIG. 17 shows an example guidance package 4 relative to the retentive pieces 27, 28 according to the relative position in FIG. 16. The dental professional may virtually place point 2 (see FIGS. 2A, 4, 16, and 17) of a guidance package 4. Virtually place point 2 at this point in space positioned at a specific distance (in some examples about 6 mm) anterior to the most anterior aspect of the maxillary retentive piece. Point 2 may represent where protrusion 7 of the mandibular guidance component 1-2 sits at rest in the maxillary guidance component 1-1 when the condyles 8 R and L of the TMJs 9R and 9L of the mandible 8-1 are in their CR positions (e.g., the jaw is in its virtual CR), developed vertically to provide a threshold clearance (in some cases 1 mm or greater) of space between the retentive pieces (where they would otherwise contact).

In another embodiment, for instance as an example in the construction of a sleep apnea guidance package appliance, using a "bilateral anterior repositioning" TMD guidance package 4-TB (e.g., as shown in FIG. 11A), the dental professional may virtually place point 2" at a point in space positioned at a specific distance (in some examples about 6 mm) to the most anterior aspect of the maxillary retentive piece. The location of Point 2", 7" (e.g., position of rest; prescribed maximum closure position) may be coincident to a position of the mandible protrusively, laterally and vertically to provide effective airway opening, and to provide a threshold clearance (in some examples about 1 mm or greater) of space between the retentive pieces (where they would otherwise contact).

For an alternative bruxism appliance, such as the "canine guidance" guidance package 4-C (e.g., as shown in FIG. 9) bruxism appliance, virtually place points 2a and 2b equidistant bilaterally, dependent upon size of the guidance package 4-C, from a point positioned at a specific distance (in some examples about 6 mm) anterior to the most anterior aspect of the maxillary retentive piece. In some embodiments, the points 2a and 2b may be between about 1 mm to about 10 mm anterior to the most anterior aspect of the maxillary retentive piece, depending on the size of the patient's stomatognathic system and the range of motion of the patient's mandible. Points 2a and 2b may represent where the protrusions 7a and 7b of the mandibular guidance component 1-2-C sits at rest in the maxillary guidance component 1-1-C when the condyles 8R and 8L of the TMJs 9R and 9L of the mandible 8-1 are in their CR positions (e.g., the jaw is in its virtual CR), developed vertically to provide a threshold clearance (in some examples 1 mm or greater) of space between the retentive pieces (where they would otherwise contact).

For another alternative bruxism appliance, such as a "group function" guidance package 4G (e.g., as shown in FIG. 10) bruxism appliance, virtually place point 2' at a point positioned at a specific distance (in some examples about 6 mm) anterior to the most anterior aspect of the maxillary retentive piece. In some embodiments, the point 2' may be between about 1 mm to about 10 mm anterior to the most anterior aspect of the maxillary retentive piece, depending on the size of the patient's stomatognathic system and the range of motion of the patient's mandible. Point 2' may represent where the mandibular guidance component 1-2-G 7' sits at rest in the maxillary guidance component 1-1-G when the condyles

8R and 8L of the TMJs 9R and 9L of the mandible 8-1 are in their CR positions (e.g., the jaw is in its virtual CR), developed vertically to provide a threshold clearance (in some examples 1 mm or greater) of space between the retentive pieces (where they would otherwise contact).

In other embodiments, for instance as an example in the construction of a guidance package appliance, such as a "bilateral anterior repositioning" TMD guidance package 4-TB (e.g., as shown in FIG. 11A) appliance, virtually place point 2" at a point positioned at a specific distance (in some examples about 6 mm) in space anterior to the most anterior aspect of the maxillary retentive piece. In some embodiments, the point 2" may be between about 1 mm to about 10 mm anterior to the most anterior aspect of the maxillary retentive piece, depending on the size of the patient's stomatognathic system and the range of motion of the patient's mandible. The location of Point 2", 7" (e.g., position of rest; prescribed maximum closure position) may be coincident to a position of the condyles 8R and 8L within the TMJs 9R and 9L other than CR, developed protrusively, laterally and vertically to recapture the discs of both TMJs 9R and 9L and to provide about 1 mm or greater of space between the retentive pieces (where they would otherwise contact).

In the case of the construction of a "asymmetric protrusive" TMD guidance package 4-TU (e.g., as shown in FIG. 12A) appliance, virtually place points 2'a and 2'b at a distance and asymmetrically bilaterally, dependent upon size of the guidance package 4-TU, from a point positioned at a specific distance (in some examples about 6 mm) anterior to the most anterior aspect of the maxillary retentive piece. In some embodiments, the points 2'a and 2'b may be between about 1 mm to about 10 mm anterior to the most anterior aspect of the maxillary retentive piece, depending on the size of the patient's stomatognathic system and the range of motion of the patient's mandible. The location of points 2'a and 2'b (e.g., position of rest) may be coincident to some position of the condyles 8R and 8L within the TMJs 9R and 9L other than CR, developed protrusively, laterally, vertically and asymmetrically so that the damaged TMJ has recaptured its' disc and the other TMJ is in a relatively normal albeit rotated state.

In the case of the construction of a "asymmetric" guidance package 4-AT (e.g., as shown in FIGS. 13A and 13B) appliance, virtually place point 2''' laterally right or left, at a distance dependent upon size, shape and orientation of the guidance package 4-AT, from a point positioned at a specific distance (in some examples about 6 mm) anterior to the most anterior aspect of the maxillary retentive piece. In some embodiments, the point 2''' may be between about 1 mm to about 10 mm anterior to the most anterior aspect of the maxillary retentive piece, depending on the size of the patient's stomatognathic system and the range of motion of the patient's mandible. The location of Point 2''' (e.g., position of rest; prescribed maximum closure position) may be determined by the dental professional for therapeutic treatment of the mandible, TMJ, or other stomatognathic malady of the mandible for that specific patient.

This point of reference (virtual point[s]) for the placement of point or points 2, 2', 2'', 2' 2a, 2b, 2'a, and 2'b of the virtual guidance package could be any of the dental professional's choosing (FIGS. 24-27) based on multiple variables, for example malocclusion, vertical dimension of rest consideration, and mechanical advantage over muscles of mastication consideration.

For a severe Class II malocclusion patient, this point or points 2, 2', 2'', 2''', 2a, 2b, 2'a, and 2'b of the virtual guidance package could be placed more posterior (e.g., as shown in FIG. 7).

For a severe Class III patient, point or points 2, 2', 2'', 2''', 2a, 2b, 2'a, and 2'b of the virtual guidance package could be placed further anterior (e.g., as shown in FIG. 8).

The dental professional could at this point virtually construct a guidance package of any design around Point 2, 2', 2'', 2''' or points 2a and 2b, or 2'a and 2'b and their still oriented mandibular components 1-2, 1-2-C, 1-2-G, 1-2-TB, 1-2-TU, 1-2-AT as shown in FIGS. 1, 9, 10, 11A, 12A, 12B, 13A and 13B. All parameters of size, shape, depth, steepness, and style of guidance can be controlled to include placement of lateral guidance 5, protrusive guidance 6, and special protrusive guidance 6a, as shown in FIGS. 2A-C, 9, 10, 11, 12A, 12B, 13A and 13B. The mandibular component may be modified regarding the number of protrusions, and the size and shape of those protrusions. The dental professional may use the border limits (range of motion) of the mandible to define the overall size of the retentive piece(s) and/or guidance package 4. The depth 32 of the guidance package, shown in FIG. 1, can be controlled. The steepness 33, shown in FIG. 1, of the guidance can be dictated by the dental professional. In some cases, for instance as an example a TMD guidance package, the guidance may be asymmetrical, specialized protrusive guidance may be included 6a (e.g., as shown in FIGS. 11A, 12A and 12B), or the range of motion could also be prescribed asymmetrically (e.g., as shown in FIGS. 12A, 12B, 13A and 13B). The dental professional may have a broad spectrum of 3D patterning available to guide the patient's mandible to a selected destination by a route chosen or designed from a broad spectrum of 3D routes available.

Alternatively, the dental professional could choose a guidance package from a library of stock virtual guidance package designs of different sizes and shapes. In other embodiments, the dental professional could choose and then modify a stock virtual guidance package from a virtual library.

The dental professional could choose an appropriate stock virtual guidance package from the virtual library and use without modification. As an example, the most common application for a bruxism guidance package appliance would be to select a stock virtual guidance package that is large enough to provide anterior guidance to avoid all interferences (e.g., collisions, movement restrictions) in a symmetrical way, provide mechanical advantage over the muscles of mastication, and provide a preferable minimum vertical dimension at rest in CR position.

Once the guidance package has been virtually modeled or chosen from a library and/or modified, a virtual functional simulation on the virtual articulator of the anterior guidance provided by the virtual guidance package may be performed to verify the dental professional's goals. Many options are available in treating TMD. For a TMD guidance package appliance goals could include special protrusive, lateral, and vertical guidance to manage the specific damage profile of a specific patient. In the case of a "bilateral anterior repositioning TMD guidance package 4-TB appliance, the objectives may be that as the patient closes his jaw special protrusive guidance is provided to bring the mandible to a position of rest 2', 7' that will recapture both discs and from that position of minimal vertical dimension at rest all excursions from that position will guide the mandible to avoid all interferences and guide the mandible in specific 3D pathways meant to therapeutically address the damage profile of that particular patient.

In the case of sleep apnea therapy using a "bilateral anterior repositioning" TMD guidance package 4TB, as shown in FIG. 11A, appliance, the objectives may be that as the patient closes his jaw special protrusive guidance is provided to bring the mandible to a position of rest 2', 7' that will open the airway effectively to treat sleep apnea, and from that position of minimal vertical dimension at rest all excursions from that position will guide the mandible to avoid all interferences and guide the mandible in specific 3D pathways meant to therapeutically address the sleep apnea of that particular patient.

In the case of a "asymmetric protrusive" TMD guidance package 4-TU (FIGS. 12A and 12B) appliance, the objectives may be that as the patient closes his jaw special protrusive guidance is provided to bring the mandible to a position of rest 2'a and 2'b that will recapture the disc of the damaged TMJ and leave the other condyle in a relatively normal position albeit somewhat rotated and from that position of minimal vertical dimension of rest all excursions from that position will guide the mandible to avoid all interferences and guide the mandible in specific 3D pathways meant to therapeutically address the damage profile of that particular patient. In the case of an "asymmetric" TMD guidance package 4-AT appliance, the objectives may be determined by the operator for therapeutic treatment of the mandible, TMJ, or other stomatognathic malady of the mandible for that specific patient for the position or rest 2''', 7''' and from that position of minimal vertical dimension of rest all excursions from that position will guide the mandible to avoid all interferences and guide the mandible in specific 3D pathways meant to therapeutically address the damage profile of that particular patient.

However most commonly, a dental professional may be creating a guidance package bruxism appliance, having goals of the elimination of all posterior interferences therefore eliminating destructive engrams reducing muscle spasms, protection of the teeth and TMJs, an increased mechanical advantage over the muscles of mastication, a minimal vertical dimension at centric occlusion rest position 2, 2', 2a, 2b, 7, 7', 7a, and 7b and ideal 3D anterior guidance from that position creating a superior anterior guidance bruxism appliance.

The method may optionally include virtually applying one or more shelves/protrusions as a bridge between the retentive pieces 10 and the respective virtual guidance package components taking care to remain inside the envelope of function of the guidance package on both the maxillary and mandibular aspects of the guidance package appliance 13. The vertical dimension 16 for a patient at rest (prescribed maximum closure position) of the guidance package appliance 13 in the examples of FIGS. 6 through 8 can remain minimized irrespective of the Class of the malocclusion by fixing the relative position of the virtual shelf/protrusion on the frontal surface of the retentive piece 10 of the current example embodiment that receives the appropriate component of the guidance package 4.

The guidance package may enable guidance irrespective of the positions of the teeth, combined with the virtual retentive piece and shelves/protrusions, which in turn enables the dental professional to place the guidance package in a location to maximize guidance, maximize mechanical advantage over muscles of mastication, and minimize vertical dimension at rest (see FIG. 5).

As shown in FIGS. 7 and 8, the shelves/protrusions may receive the mandibular guidance component 1-2 of the guidance package 4 for a Class II malocclusion patient and the shelf/protrusion receives the maxillary guidance component of the guidance package 4 for a Class III malocclusion patient. In the construction of a sleep apnea guidance package appliance, the dental professional may assume a Class III malocclusion point of view in selecting the shelf/protrusion because that is the end therapeutic goal. The retentive piece may have multiple protrusions or shelves in various shapes and sizes that serve as attachment points and/or platforms for all guidance and stop features of the guidance packages or generated by guidance packages of the present disclosure. For a non-malocclusion case, Class I, as shown in FIG. 6, the shelves/protrusions of the retentive piece 10 may be applied as a bridge to the respective component of the guidance package for both the maxillary arch 22 and mandibular arch 20.

This data and information, collected from the above steps, may be used to design a final solution (e.g., an appliance). The design for a final solution may be transferred to a manufacturer who has, for example, CAM (Computer Aided Manufacturing) or CNC (Computer Numerical Control) technology and equipment, an in-office 3D printer, or another manufacturing or printing system. In some embodiments, a two-piece CAD-CAM guidance package appliance, a two-piece CAD-CAM TMD guidance package appliance, or a two-piece CAD-CAM sleep apnea guidance package appliance can be automatically produced or re-produced that is customized for a specific patient, consisting of a maxillary aspect and a mandibular aspect, which is comfortable to wear, irrespective of the malocclusion type including open bite, deep bite, cross bite, severe Class II, and Class III (see FIGS. 6 to 8).

The style, shape, steepness, depth, and size of the guidance package which could be a stock guidance package, a modified from a stock guidance package or specifically designed is dependent upon the problem or combination of problems and the occlusion or malocclusion that particular patient exhibits.

Figure 18:
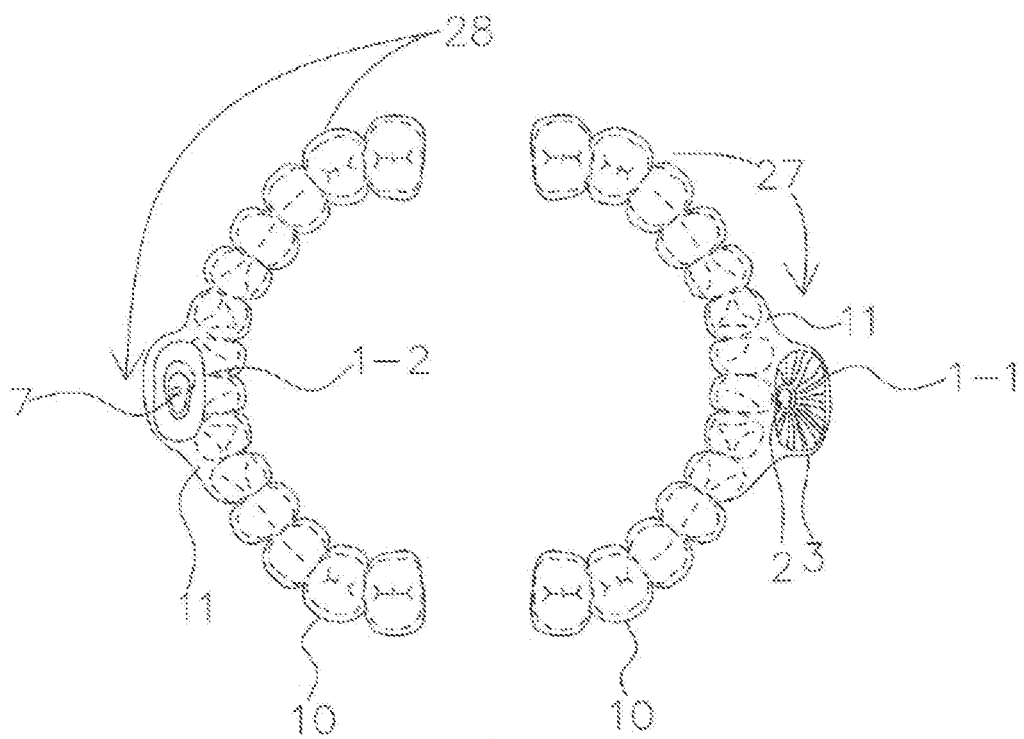
FIG. 18 is a perspective view of a completed CAD-CAM guidance package derived appliance for a patient without a severe malocclusion, Class I, from the inside of the mouth, in accordance with an example embodiment.

FIG. 18 shows an example completed CAD-CAM guidance package appliance or a CAD-CAM TMD guidance package appliance for a patient without a severe malocclusion, Class I, from the inside of the mouth. In this example, both the maxillary retentive piece 27 and mandibular retentive piece 28 of the CAD-CAM guidance package appliance may be included of the retentive pieces 10. The maxillary and mandibular guidance package appliance subsets, including the retentive piece and the guidance component 1-1 or 1-2 of the guidance package, may be connected seamlessly by the shelves/protrusions.

Figure 19:
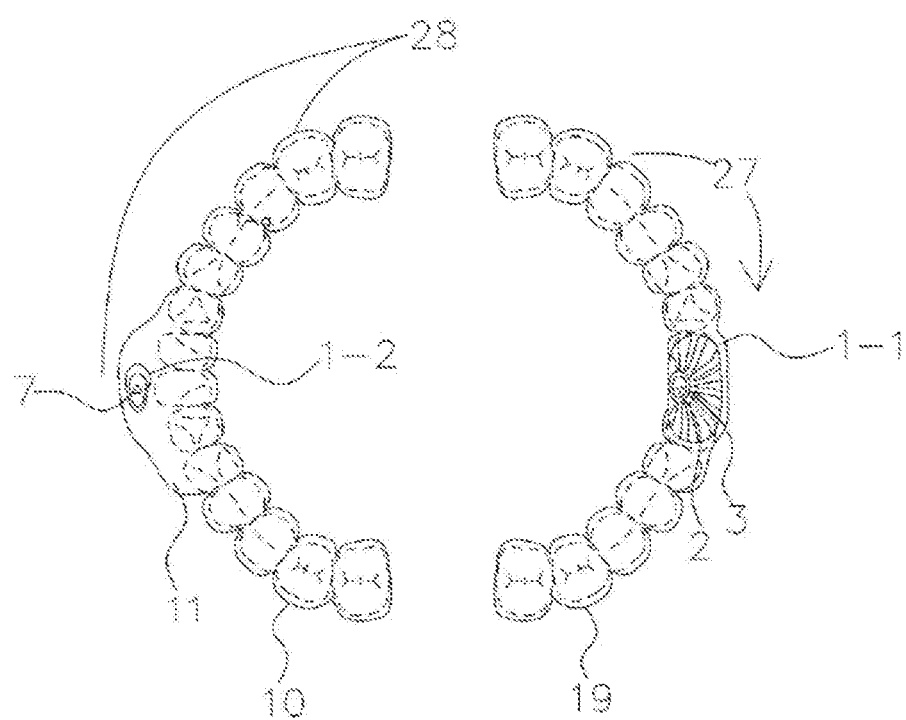
FIG. 19 is a perspective view of a completed CAD-CAM guidance package derived appliance for a patient with a Class II malocclusion from the inside of the mouth, in accordance with an example embodiment.

FIG. 19 shows an example completed CAD-CAM guidance package appliance or CAD-CAM TMD guidance package appliance for a patient with a severe Class II malocclusion from inside the mouth. For a severe Class II malocclusion, the mandibular retentive piece 28 may be a retentive piece 10, which has a shelf/protrusion to receive the mandibular guidance component 1-2, and the maxillary retentive piece can be a retentive piece 10, which provides a shelf/protrusion as a platform.

Figure 20:
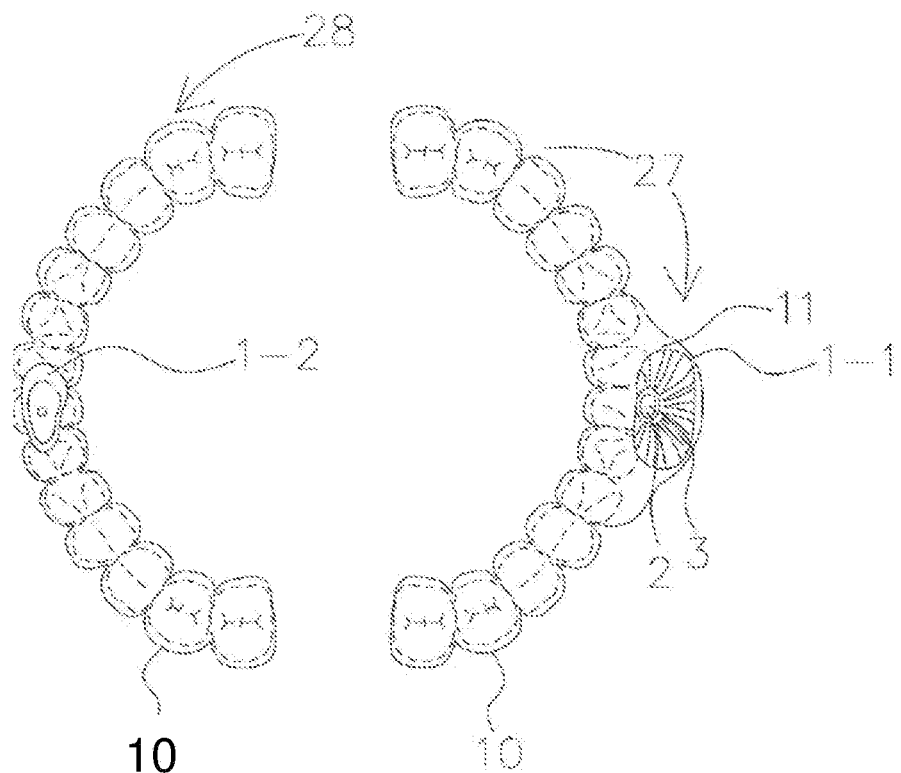
FIG. 20 is a perspective view of a completed CAD-CAM guidance package derived appliance for a sleep apnea patient or a patient with a Class III malocclusion from the inside of the mouth, in accordance with an example embodiment.

FIG. 20 show an example completed CAD-CAM guidance package appliance, CAD-CAM TMD guidance package appliance for a patient with a Class III malocclusion, or a CAD-CAM sleep apnea guidance package appliance from inside the mouth. For a Class III malocclusion or for treatment of sleep apnea, the maxillary retentive piece 27 may be a retentive piece 10, which has a shelf/protrusion to receive the maxillary guidance component 1-1, and the mandibular retentive piece can be a retentive piece 10 that provides a shelf/protrusion as a platform.

Located in the mouth with a minimal vertical dimension 16 penalty at rest in CR, or any position of the dental professional's choosing, a custom guidance package appliance may be composed of thin custom-fitting retentive pieces and the attached guidance package 4, 4-C, 4-G, 4-TB, 4-TU, or 4-AT. The guidance package portion of the appliance 13 may be positioned in a smooth compartment-like package between the patient's lips, anterior to the teeth in most cases dependent upon the malocclusion, and therefore, the position of the guidance package in relation to teeth and lips. As the patient's mouth closes, the maxillary component of the guidance package appliance may contact the mandibular component guiding the mandible into Point 2, 2', 2", 2''' or Points 2a and 2b, or 2'a and 2'b and area 3, 3', 3", 3''' as shown in FIGS. 2A, 4, 9, 10, 11A, 12A, 12B, 13A and 13B. This index position area would most commonly be CR (e.g., Point 2 in FIG. 4, Points 2a and 2b in FIG. 9, Point 2' in FIG. 10) and the long centric area (e.g., Area 3 and 3' in FIGS. 4, 9, and 10) but could in the case of a TMD guidance package management appliance, a stomatognathic treatment TMD guidance package appliance, or a sleep apnea guidance package appliance, be a position other than CR prescribed by the dental professional (e.g., Point 2" in FIG. 11A and Point 2''' in FIGS. 13A and 13B, or Points 2'a and 2'b in FIGS. 12A and 12B). The maxillary guidance component 1-1, 1-1-C, 1-1-G, 1-1-TB, 1-1-TU, 1-1-AT of the guidance package 4 may fit over the mandibular component 1-2, 1-2-C, 1-2-G, 1-2-TB, 1-2-TU, 1-2-AT. The entire inferior perimeter of the maxillary component of the guidance package 4 may be wider than the mandibular component of the guidance package and its housing. That perimeter 1-4 in FIG. 2A may also have a designated thickness (in some examples between about 2 mm to about 6 mm) and be shaped like a bumper to prevent the lips from ever being pinched when the patients' mouth closes. In other embodiments, the perimeter 1-4 may have a thickness between about 1 mm to about 10 mm.

Finally, when the various guidance packages 4, 4S, 4-C, 4-G, 4-TB, 4-TU, and 4-AT (e.g., as shown in FIGS. 1, 9, 10, 11A, 12A, 12B, 13A and 13B) appliances for patients with different malocclusions are manufactured by the CAD-CAM method, all the retentive pieces 27, 28 and their respective guidance package components 1-1, 1-1-c, 1-1-G, 1-1-TB, 1-1-TU, 1-1-AT or 1-2, 1-2-C, 1-2-G, 1-2-TB, 1-2-TU, 1-2-AT may be produced in one piece without any seam lines.

Figure 21:
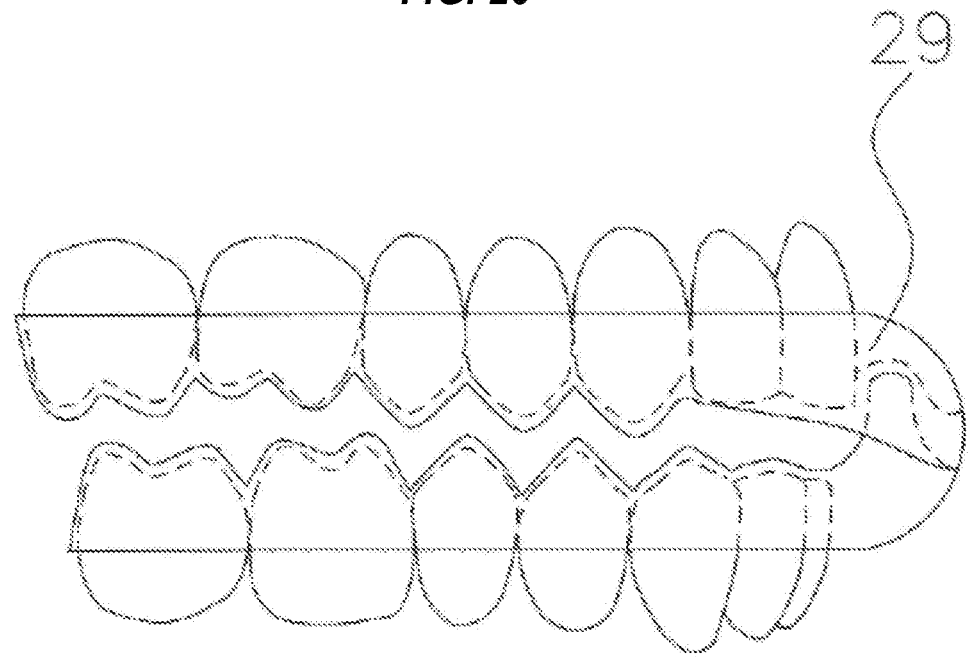
FIG. 21 is a schematic side view of a finished CAD-CAM guidance package derived appliance for a bruxism or TMD patient without a severe malocclusion, Class I, in accordance with an example embodiment.

FIG. 21 shows an example finished CAD-CAM guidance package appliance 29, which may have special properties to manage a TMD patient, or an appliance for a bruxism patient without a severe malocclusion, Class I and with or without sleep apnea. Compared with FIG. 6, it is simpler to produce and much simpler to reproduce.

Figure 22:
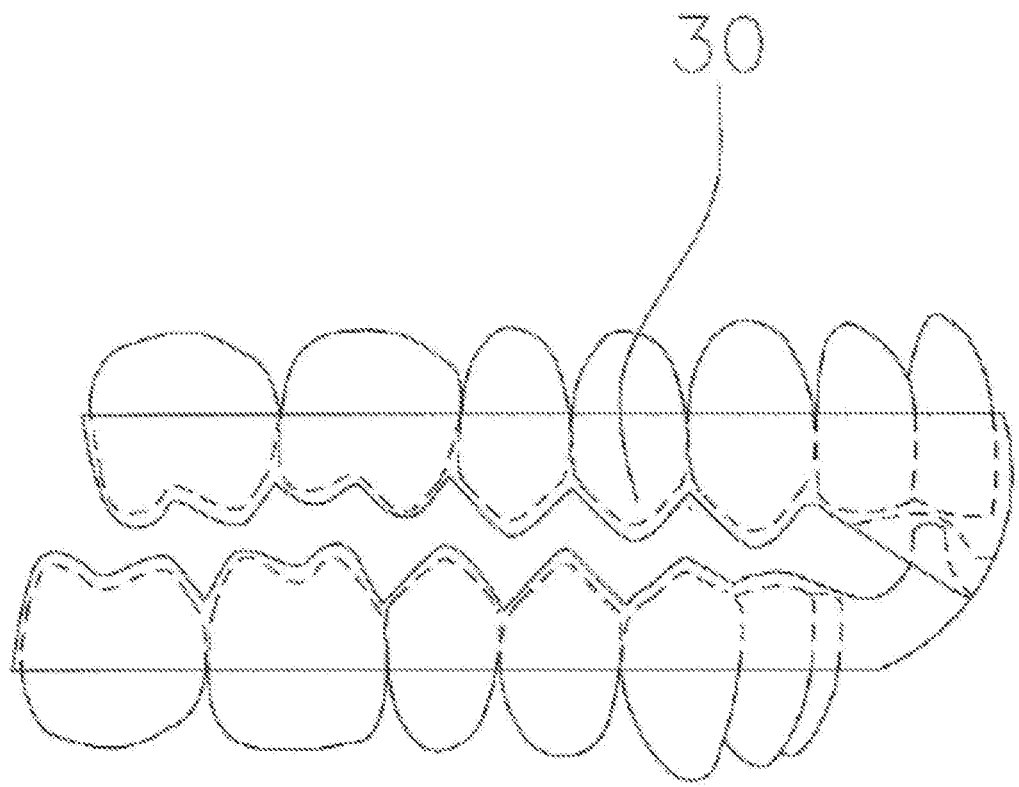
FIG. 22 is a schematic side view of a finished CAD-CAM guidance package derived appliance for a bruxism or TMD patient with a Class II malocclusion, guidance package derived appliance in accordance with an example embodiment.
Figure 23:
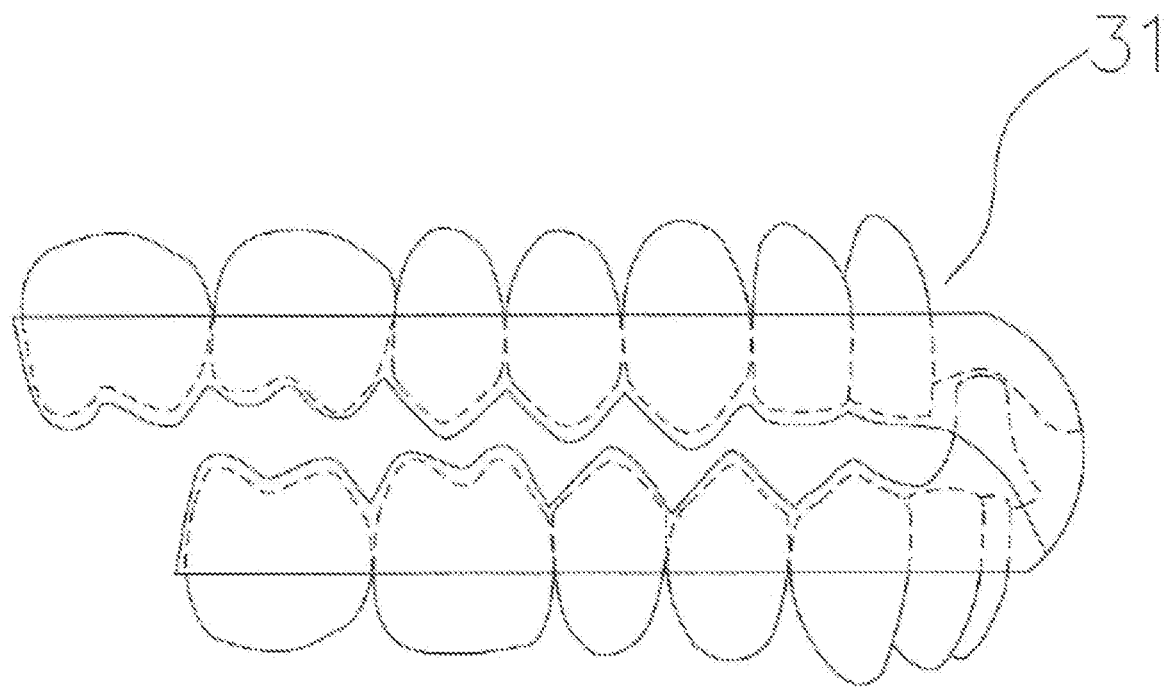
FIG. 23 is a schematic side view of a finished CAD-CAM guidance package derived appliance for a bruxism or TMD patient with a Class III malocclusion, or a sleep apnea guidance package derived appliance in accordance with an example embodiment.

Similarly, FIG. 22 shows an example finished CAD-CAM guidance package appliance 30 that may have special properties to manage a TMD patient, a bruxism patient with Class II malocclusion, or a sleep apnea patient with a Class II malocclusion. FIG. 23 shows an example CAD-CAM guidance package appliance 31, which may have special properties to manage a TMD patient, a bruxism patient with a Class III malocclusion, or a sleep apnea patient.

Figure 24A:
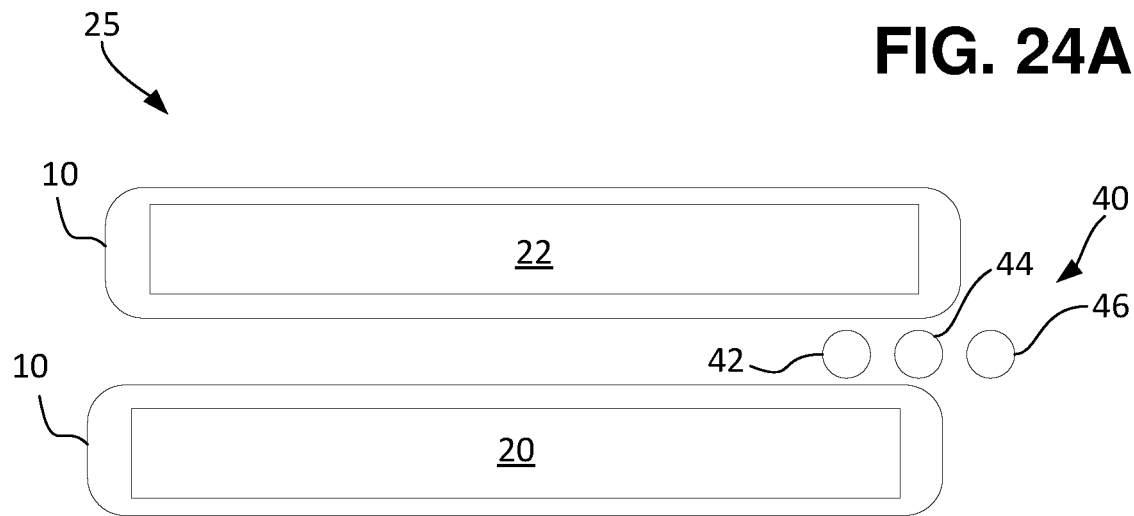
FIG. 24A is a conceptual drawing of the relative position of the maxillary and mandibular retentive pieces and virtual point(s) along the transverse plane for a bruxism or TMD patient without a severe malocclusion, Class I, in accordance with an example embodiment.
Figure 24B:
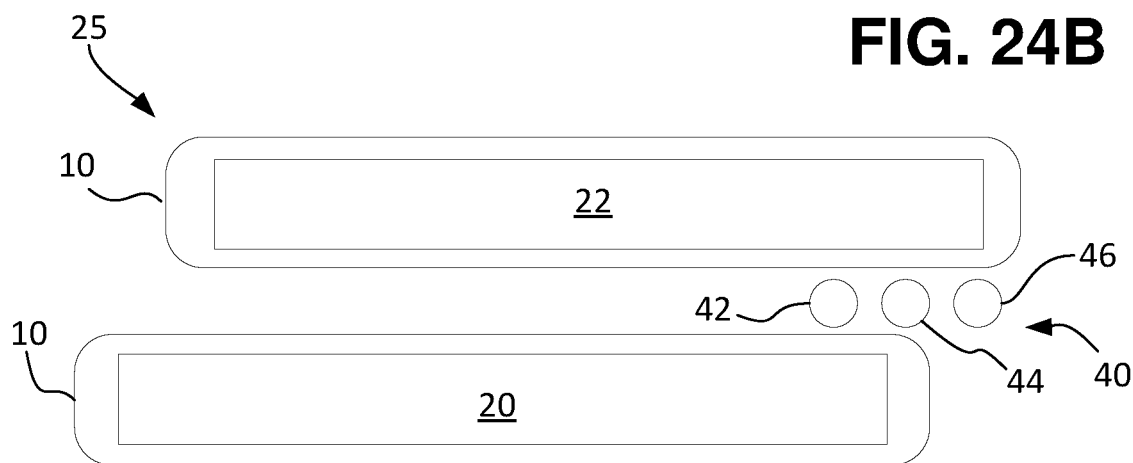
FIG. 24B is a conceptual drawing of the relative position of the maxillary and mandibular retentive pieces and virtual point(s) along the transverse plane for a bruxism or TMD patient with a Class II malocclusion, in accordance with an example embodiment.
Figure 24C:
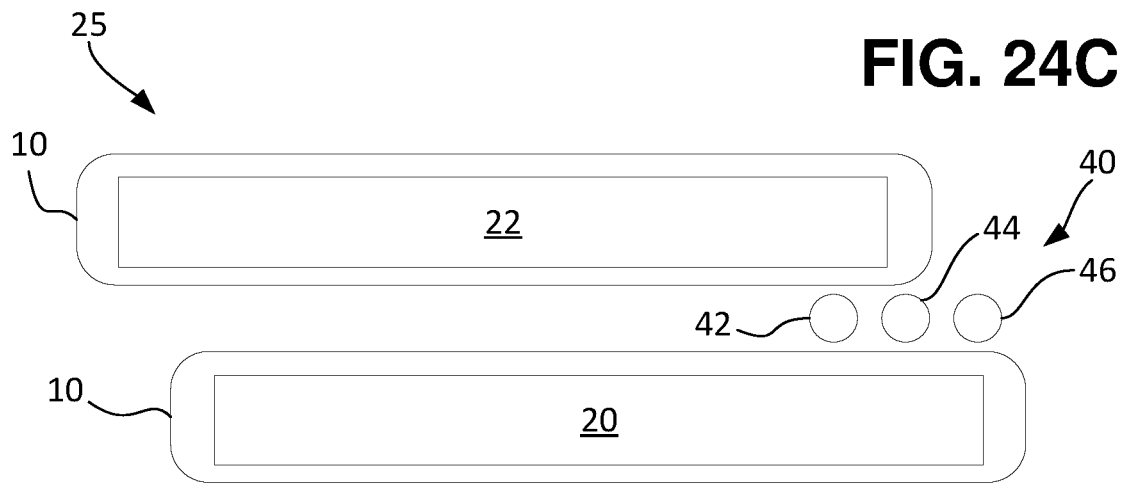
FIG. 24C is a conceptual drawing of the relative position of the maxillary and mandibular retentive pieces and virtual point(s) along the transverse plane for a bruxism TMD patient with a Class III malocclusion, or a sleep apnea patient in accordance with an example embodiment.

FIGS. 24A-24C show an example positioning of the virtual point(s) relative to one or more of the maxillary and mandibular retentive pieces that provide multiple protrusions or shelves in all shapes and sizes that serve as attachment points and/or platforms for guidance packages and/or all the guidance and stop features generated by guidance packages in the transverse, sagittal, and frontal axes. Virtual point placement may be automated or operator determined. As the placement and orientation of the guidance package becomes more automated, the more likely subsequent adjustments to the guidance package will be necessary. Alternatively, the virtual point(s) may be placed optimally 3Dly so that a guidance package may be used without modification (FIGS. 24A-27). The virtual points (FIGS. 24A-27) may represent one point for positioning of the guidance package or may represent a plurality of points for both positioning and orientation of the guidance package.

In FIG. 24A, for a patient without a severe malocclusion, Class 1, retentive pieces 10 may be placed on the maxillary arch 22 and mandibular arch 20, with the maxillary arch 22 extending anteriorly beyond the mandibular arch 20 (albeit slightly). In FIG. 24B, for a patient with a Class II malocclusion, the retentive piece 10 may be placed on the mandibular arch 20, to provide a shelf/protrusion as an attachment point and may be placed on the maxillary arch 22 to provide a shelf/protrusion as a platform. In FIG. 24C, for a patient with a Class III malocclusion or for a sleep apnea appliance, the retentive piece 10 may be placed on the mandibular arch 20 to provide a shelf/protrusion as a platform, while the retentive piece 10 may be placed on the maxillary arch 22 to provide a shelf/protrusion as an attachment point.

Positioned between the arches 20, 22, a plurality of potential virtual points 40 may designate contact points between guidance package maxillary and mandibular guidance components. In some embodiments, one or more of the guidance package guidance components may be set based on a virtual point 40 such that when the guidance package guidance components contact, the virtual maxillary and mandibular arches 22, 20 are placed in the predetermined index position (prescribed maximum closure position). In some embodiments, the potential virtual points 40 may include one or more interior virtual points 42, edge virtual points 44, and anterior virtual points 46. The interior virtual point(s) 42 may not provide an ideal vertical dimension at rest, may provide the least mechanical advantage over muscles of mastication, and may interfere with other functions of the mouth. The edge virtual point(s) 44 may not provide an ideal vertical dimension at rest, may provide limited mechanical advantage over muscles of mastication, and may or may not interfere with other functions of the mouth. The anterior virtual point(s) 46 may provide optimal placement that enables ideal vertical dimension at rest, the greatest mechanical advantage over the muscles of mastication, and minimum interference with other functions of the mouth.

Figure 25:
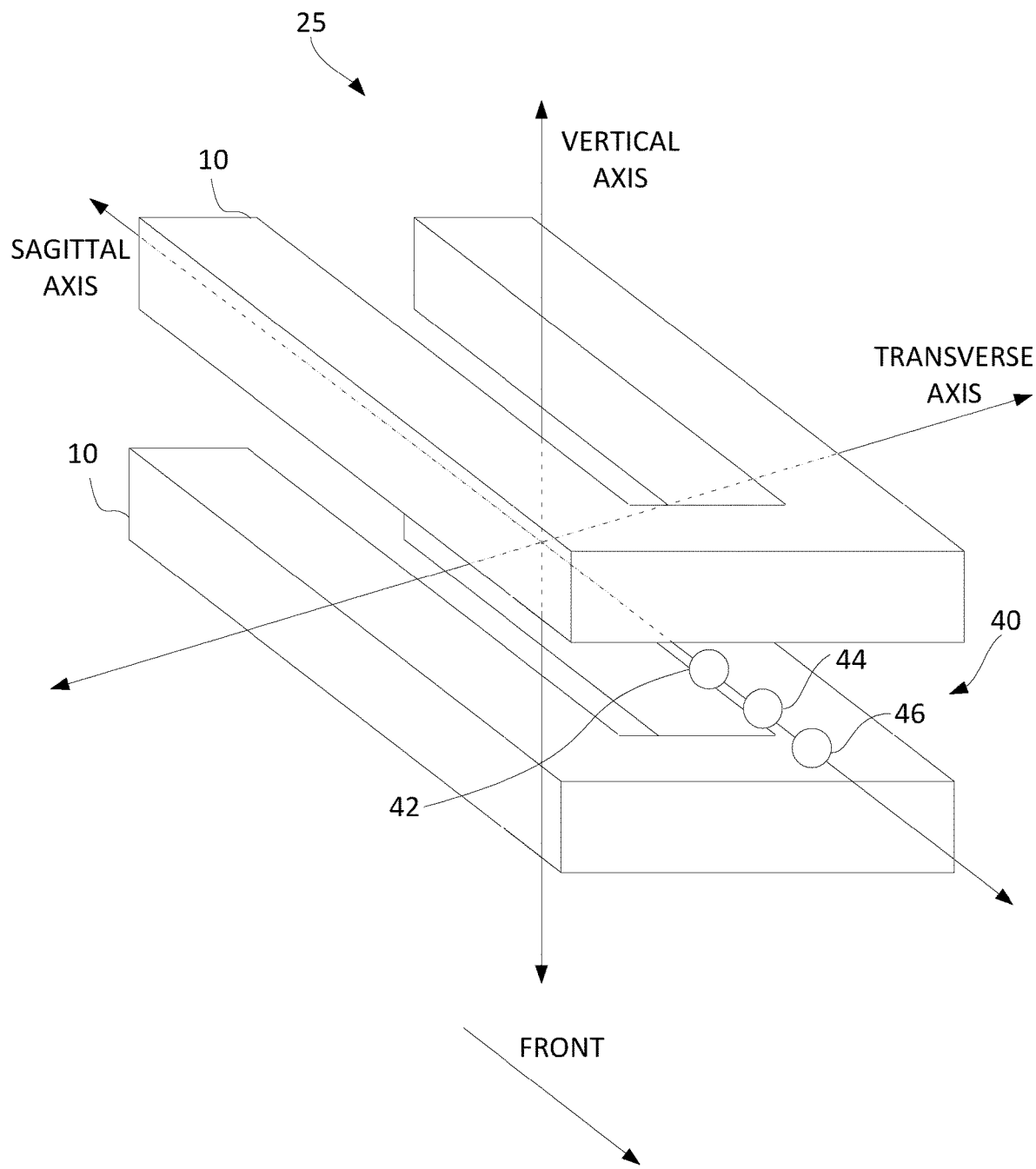
FIG. 25 is a conceptual drawing of potential positions of a single virtual point along the transverse plane between the maxillary and mandibular retentive pieces for a bruxism or TMD patient without a severe malocclusion, Class I, in accordance with an example embodiment.
Figure 26:
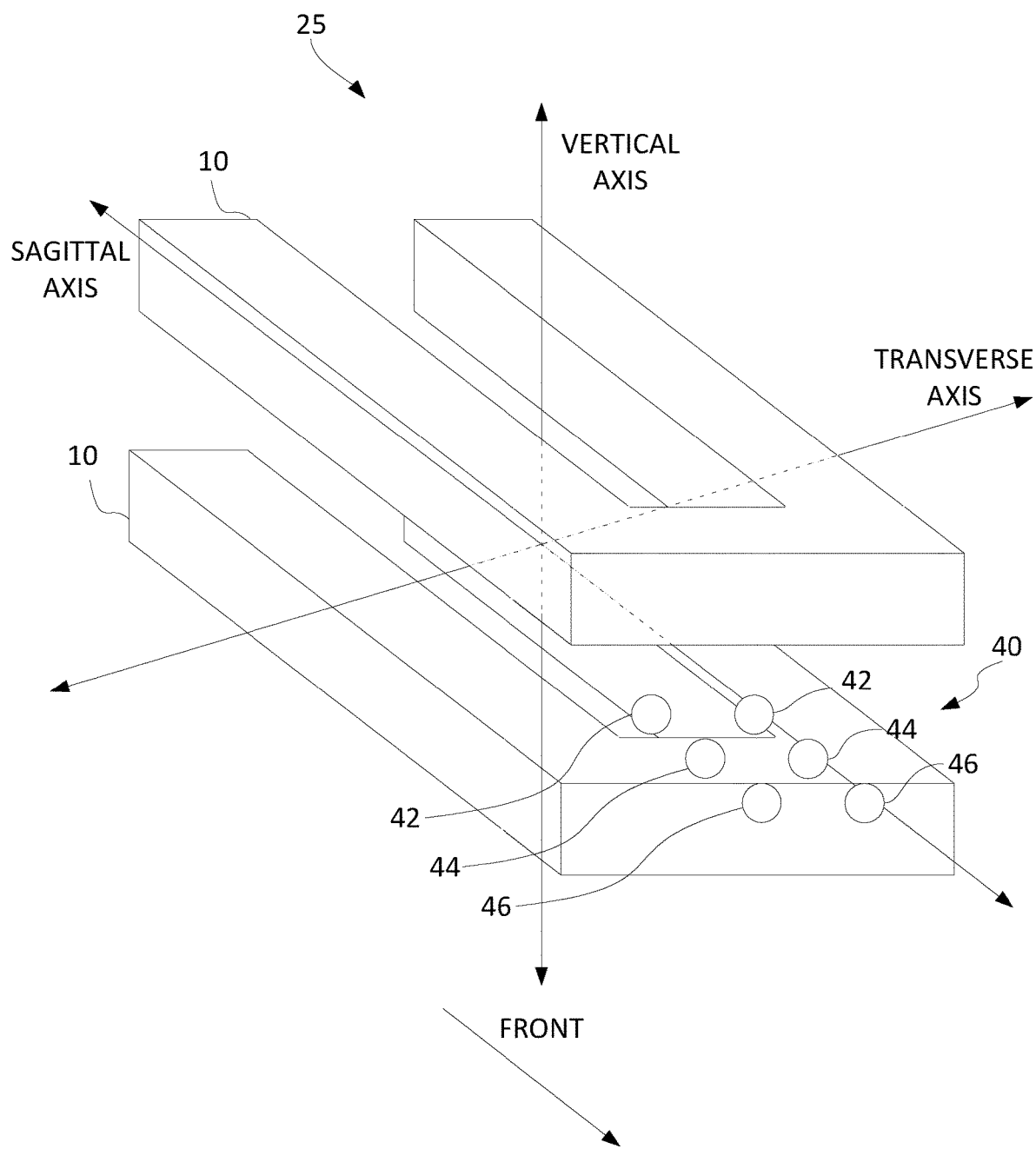
FIG. 26 is a conceptual drawing of potential positions of a pair of virtual points along the transverse plane between the maxillary and mandibular retentive pieces for a bruxism or TMD patient without a severe malocclusion, Class I, in accordance with an example embodiment.

FIGS. 25 and 26 provide a 3D view of the example retentive pieces 10 for a patient without a severe malocclusion, Class 1, as shown in FIG. 24A. In FIG. 25, a single virtual point (e.g., one of the interior virtual point 42, edge virtual point 44, or anterior virtual point 46) may be positioned between the retentive pieces proximate the sagittal axis (e.g., along the mid-sagittal plane). Alternatively, as shown in FIG. 26, a pair of virtual points (e.g., two interior virtual points 42, edge virtual points 44, or anterior virtual points 46) may be positioned between the retentive pieces proximate the sagittal axis (e.g., along the mid-sagittal plane). The pair of virtual points may be asymmetrically positioned in relation to the mid-sagittal plane. The virtual point(s) may be positioned proximate a vertical plane perpendicular to the mid-sagittal plane. In some embodiments, the vertical plane may be positioned at a specific distance (in some examples about 6 mm) anterior to the most anterior aspect of the maxillary retentive piece along an occlusal plane mid-sagittally. The virtual points indicated may represent one virtual point or a grouping of virtual points that may also enable orientation. In some cases, a single virtual point may indicate orientation as well as position (e.g., as a virtual vector).

Figure 27:
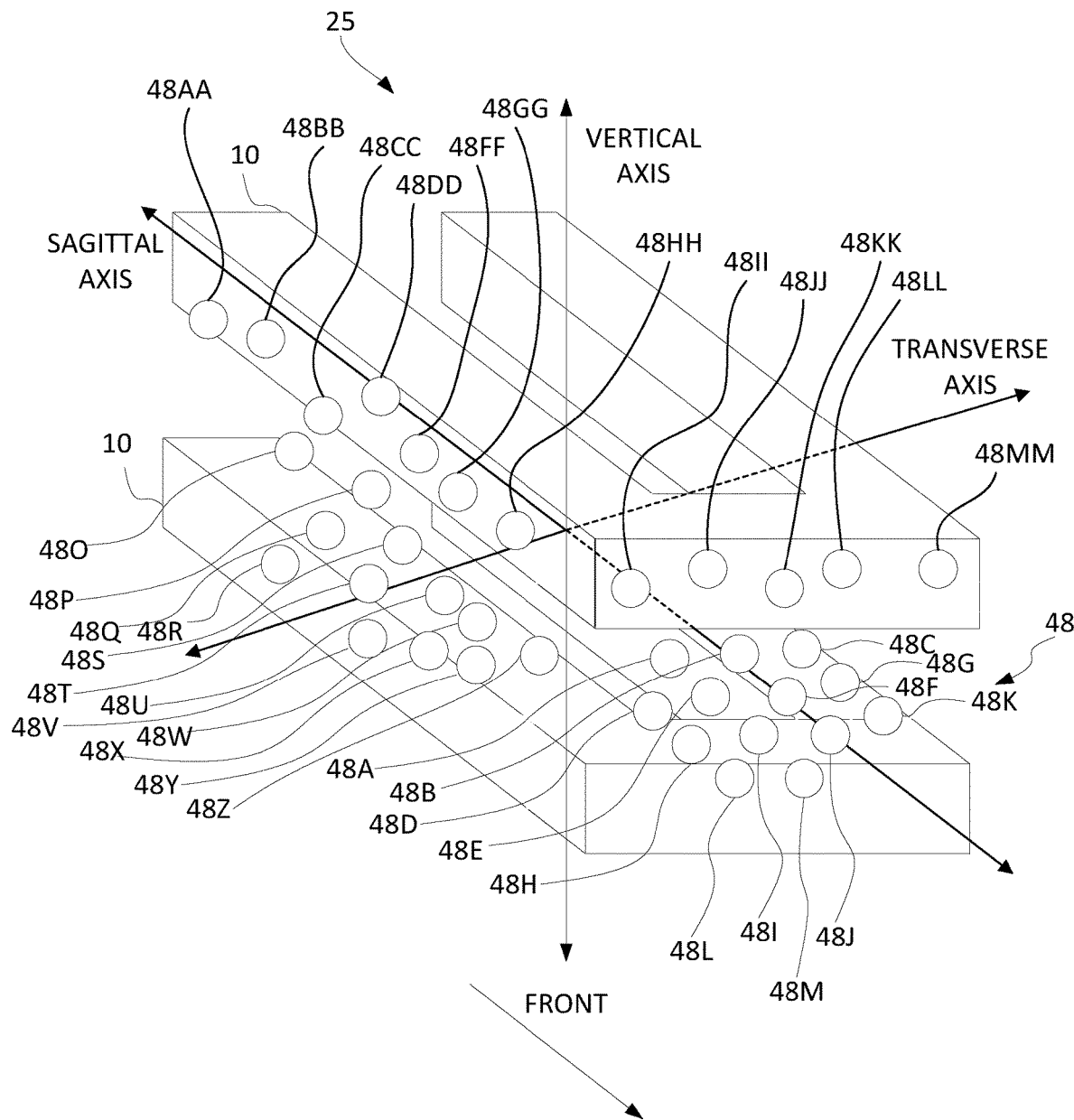
FIG. 27 is a conceptual drawing of potential positions of a single virtual point inside a virtual envelope bordered transversely, sagittally, and vertically by the 3D criterion for selecting that virtual point.

FIG. 27 shows a plurality of potential locations in all three axes (e.g., sagittal, vertical, and transverse) for a virtual point or points, which may better enable an operator to use an unmodified virtual stock guidance package or require less customization of the stock guidance package or designate attachment points for portions of guidance package solutions. In other words, allowing a dental practitioner to select any position in 3D virtual space as the virtual point maximizes the range of orientation, alignment, and position that a stock (not modified), or a scaled using patient data guidance package, or a portion of a guidance package may be used to fit a particular patient. As shown, a virtual point 48 may be placed anywhere in 3D virtual space, for example, such as any of potential virtual point positions 48A-48MM as non-limiting examples. Although virtual points 48A-48MM are depicted, it will be understood that these are merely examples and the virtual point may be defined in various positions within or exterior to the virtual arches. It is contemplated that, while the virtual point 48 may be proximate mid-sagittal and occlusal planes, it may be placed anywhere in 3D space to accommodate any disease, deformity, damage, area requiring treatment, and the like. Further, a series of guidance package appliances may be used to progressively treat and/or correct any damage, and the series of guidance package appliances may be virtually designed and produced without requiring extensive customization of physical appliances by trial and error. In one example embodiment, the first guidance package appliance in a series may have a virtual point proximate position 48A, while a later guidance package appliance in the series may have a virtual point proximate position 48F, which is closer to an example "ideal position" proximate the mid-sagittal and occlusal planes. In other embodiments, a series of different index positions of mandible in relation to maxilla are planned, to gradually bring a mandible from a particular index position in relation to the maxilla to another position. A series of appliances could be planned for this major therapeutic movement over time of the mandible in relation to the maxilla.

Figure 28:
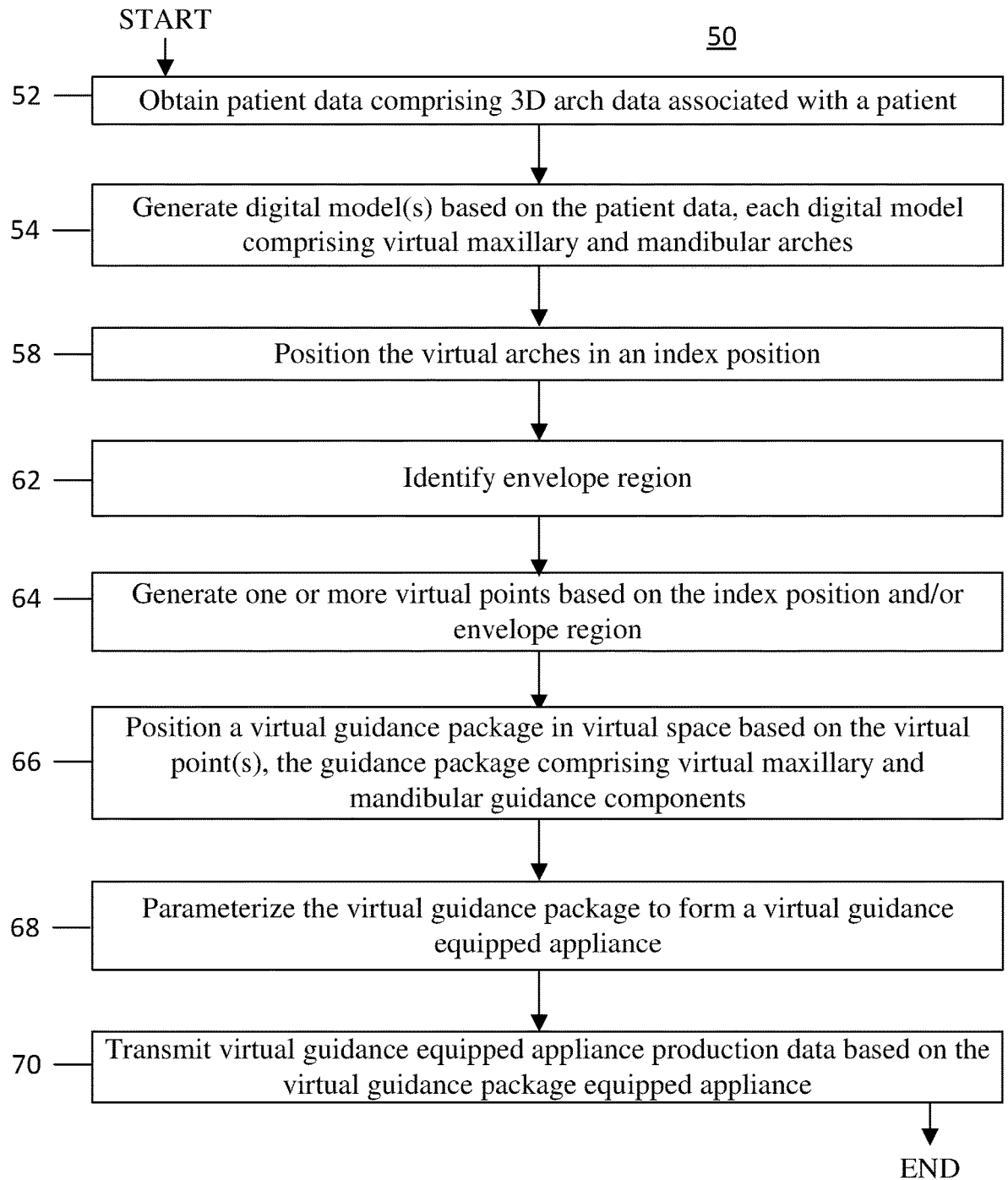
FIG. 28 is a flowchart for a method for preparing a guidance package equipped appliance for a patient with one or more of bruxism, TMD, and sleep apnea, in accordance with an example embodiment.

FIG. 28 is a flowchart of an example method 50 for preparing a guidance package equipped appliance for a patient with one or more of bruxism, TMD, and sleep apnea. As shown, the method 50 may include obtaining patient data 52 including 3D arch data associated with the patient. After obtaining the patient data, one or more digital models may be generated 54 on one or more processors based on the patient data, e.g., in a virtual articulator. The one or more digital models may include virtual maxillary and mandibular arches in the virtual articulator. The virtual arches may be positioned 58 in an index position (prescribed maximum closure position) for the patient. In some cases, the index position includes clearance for guidance features and any retentive piece.

An envelope region (3D region) may be identified 62, which defines a space within which a retentive piece and/or guidance package may be utilized. In some cases, a 3D region may be a space defined as the negative space formed when the mandible and maxilla of the patient are at a point of first contact or when the mandible and maxilla are further separated. In some cases, an envelope region (3D region) may be defined as a space formed between one or more surfaces of positioned retentive pieces. In some cases, a 3D region may be defined as global 3D space or working space for the retentive piece(s), the guidance package, and other functions of the guidance package system. In some cases, a boundary 3D space may be defined by virtual planar curves. In some embodiments, an envelope region may include tissue or teeth of a patient; in this case, implementing the solution may include surgery or implants. In some embodiments, an envelope region may be predefined for a particular patient or a particular guidance package. In some embodiments, a system may automatically generate boundaries of an envelope region (the 3D region) based on one or more of patient data (e.g., tissue surfaces, TMJ data), the curves of occlusion, and the type of solution. For example, in some cases, for a restoration guide solution, the system may identify interferences (e.g., an oversized tooth), and include a portion of the identified interferences within an envelope region. In other situations, for a one-piece appliance solution, the system may identify the tissue surface of one arch and a (virtual) retentive piece (or a virtual planar curve) fitted over the opposing arch as defining boundaries of an envelope region.

One or more virtual points may be generated 64 based on the index position and/or an envelope region. A virtual guidance package may be positioned 66 in virtual space based on the one or more virtual points (e.g., location and alignment). The guidance package may include a movement profile that describes how the mandible should move relative to the maxilla as the mandible closes from the point of first contact to the index position.

After positioning the guidance package 66 in virtual space, the virtual guidance package may be parameterized 68 to form a virtual guidance package equipped appliance. In some cases, one or more retentive pieces may be parameterized 68 as part of the guidance package equipped solution. Guidance package equipped appliance production data based on the virtual guidance package equipped appliance can then be transmitted 70. For example, the guidance package equipped appliance production data may be transmitted to a manufacturer equipped with one or more of CAM, CNC technology, an in-office 3D printer, and other CAM enabled device.

It will be understood that certain elements of the method described above may be executed in different orders or executed simultaneously. For example, an envelope region (appropriate 3D space) may be identified 62 before the index position is determined.

In some embodiments, there is provided a method including obtaining 3D arch data, obtaining or inputting TMJ data including range of motion of the mandible, determining movement parameters and collision (e.g., interference) detection in order to identify the movement restrictions, understand current patient situation (or obtaining this data using a JMA), establishing an envelope region (e.g., with or without virtual retentive pieces), establishing virtual point(s) based on an index position, parameterize a movement profile, and creating one or more of surgical, restorative and implant placement guides and retentive pieces (either virtually or through manufacturing) if/as needed (e.g., based on a desired solution).

In some embodiments, there is provided a method including obtaining 3D arch data, obtaining or inputting TMJ data including range of motion of the mandible, determining movement parameters and collision (e.g., interference) detection in order to identify the movement restrictions, understand current patient situation (or obtaining this data using a JMA), establishing virtual point(s) based on an index position, inserting a virtual representation of a guidance package at the index position, and creating (e.g., using CAM) one or more solutions (e.g., appliances or retentive pieces) including a same shape as the guidance package.

Parameterization

In some cases, a global 3D space is defined to manipulate retentive pieces, guidance packages, and all other functions of the guidance package system. In some cases, a 3D region is created to manipulate only the guidance package system, guidance packages may be pre-sized or a size, or relative size and orientation of aspects of guidance components within the guidance package may be determined, scaled using patient data, or adjusted as needed, and then directly attached to retentive pieces and CAM produced. However, this may not be an appropriate final form for a specific individual or final purpose. Accordingly, a customized for a particular patient or a particular purpose movement profile (e.g., guidance and stop profile) within the virtual articulator may also be considered a geometrical or mathematical object. According to one or more embodiments, the method can further include parameterization of the retentive piece and/or include a parameterization of the customized movement profile (geometrical object) within a boundary of an envelope region (a global 3D region or a more limited 3D region) and selection of different synergistically shaped guidance packages. In other words, a movement profile can be defined for a specific patient, and guidance packages for implementing the movement profile can be derived therefrom. This mathematical manipulation of the retentive piece(s) and/or the customized guidance and stop profile enable a broad range of products and services for implementing the guidance and stop profiles, including two piece appliances, one piece appliances, two piece restorations, one piece restorations, surgical guides, restorative guides, and implant placement guides.

In some cases, an envelope region may be defined by a placement of one or more retentive pieces 10, for example, as illustrated in FIG. 5. In some implementations, the guidance surface 720 of the retentive piece 10 may define at least one portion of an envelope region. In other implementations, the tissue surface 710 of the retentive piece 10 may define at least one portion of an envelope region. In some circumstances, a portion of the 3D space may be defined as a planar curve that may or may not correspond to a surface of a virtual and/or physical retentive piece. The retentive piece 10 may serve as a base for any appliances or restorations developed based on the parameterization. Retentive piece 10 can also be a therapeutic entity that is then interactive with the guidance and stop system. The retentive piece 10 could include clear aligner type orthodontic appliances (e.g., Invisalign®) (or other type of therapeutic appliance) that when combined with the guidance and stop features of the guidance package system will create new therapeutic systems. The guidance incorporated with a therapeutic entity could, in some cases, help mitigate user discomfort, or increase the utility of the appliance. In some cases, a clinician may control both orthodontic tooth movement and mandibular relative to maxillary guidance and stops for new therapies in TMD, orthodontics, orthopedics, and other categories of dentistry and medicine.

A 3D region (envelope region) on a given arch may involve only space on the guidance side of the retentive piece or may involve tissue that may or may not be modified on the guidance side of the retentive piece. In other words, the guidance package system calculates the guidance profile of the mandible to a prescribed maximum closure position. This calculation can involve both the maxillary and mandibular components of guidance and stops and/or the retentive piece(s). In some circumstances, that calculation will involve not the space between the retentive pieces (including or excluding the retentive pieces) but may involve tissue (i.e., tooth structure, gingiva, bone and/or other tissues) to be modified. In some cases, calculation will involve tissue that will not be modified, but must be involved in the calculation. In this circumstance that some of the patient's tissue will be involved in the calculation, a virtual planar curve for that arch (or both arches if both arches have tissue involved in the calculation) can be virtually embedded within the tissue of that arch far enough so that all parameterizations of a movement profile that the clinician may want to use would be available. Portions of the virtual planar curve may or may not correspond to a surface of a virtual and/or physical retentive piece. In some cases, a planar curve may define a boundary of the virtual 3D region, and may be in the shape of a hyperbolic paraboloid. In some cases, a 3D region (envelope region) may be defined prior to virtual retentive piece placement by use of a planar curve that may or may not later correspond to a surface of a retentive piece. For example, consider a case of an oversized tooth, which prevents proper closure. To provide additional corrective measures, an envelope region may extend into the oversized tooth. Certain parameterizations may then depend upon the tooth being shaved down.

Figure 29:
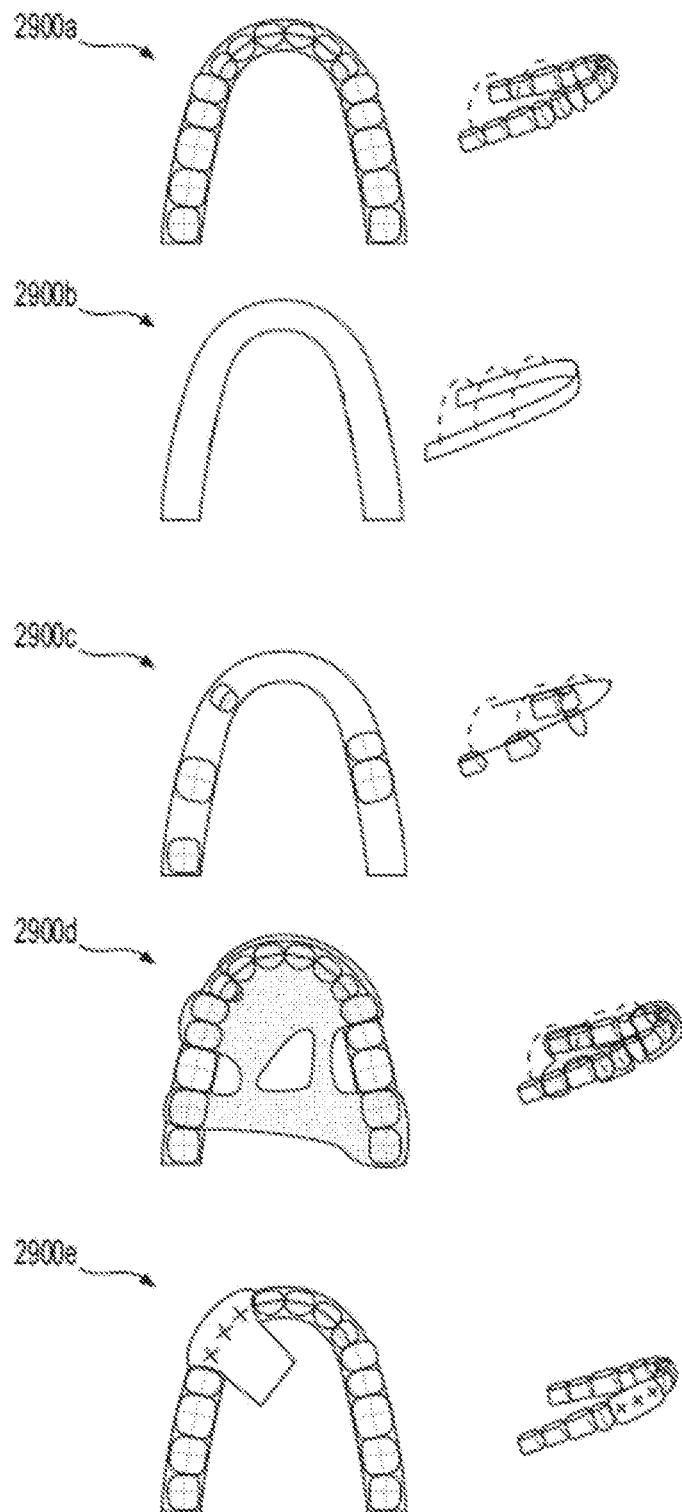
FIG. 29 illustrates example arch types that may be accommodated with a guidance package according to some example embodiments.

An envelope region (3D region) may be defined for various arch and tissue surfaces. FIG. 29 illustrates various types of arches, including a dentate arch 2900-*a* (having all teeth), an edentulous arch 2900-*b* (having no teeth), a partially dentate arch 2900-*c* (missing some teeth), an arch of existing dentition, or prosthetics or combination 2900-*d* (e.g., an arch having some existing dental work), and an atypical arch 2900-*e* (e.g., an arch in transition such as an arch undergoing surgery or rehabilitation or other circumstances). Envelope regions (virtual 3D regions) may be defined as the tissue surfaces of the arches, a region embedded within tissue on the arches, or guidance side surfaces 720 of retentive pieces, or tissue side surfaces 710 of retentive pieces, or other surfaces of retentive pieces 10 placed or virtually placed around the arches. In some embodiments, the appropriate 3D space may be defined by planar curves that may or may not represent a surface of a virtual and/or physical retentive piece. If utilized, retentive pieces 10 may use various attachment mechanisms including compressive material like plastic or other material, adhesive, wire, vacuum, clasps, bonding materials, implants, mini implants, or other appropriate mechanisms based on the arch and desired retention mechanism (e.g., stainless steel or titanium surgical screws to attach the retentive piece directly to bone of an arch in transition).

The various types of arches depicted in FIG. 29 may apply to either the mandible or maxilla. In some cases, the mandible and maxilla may have different arch types.

Figure 30A:
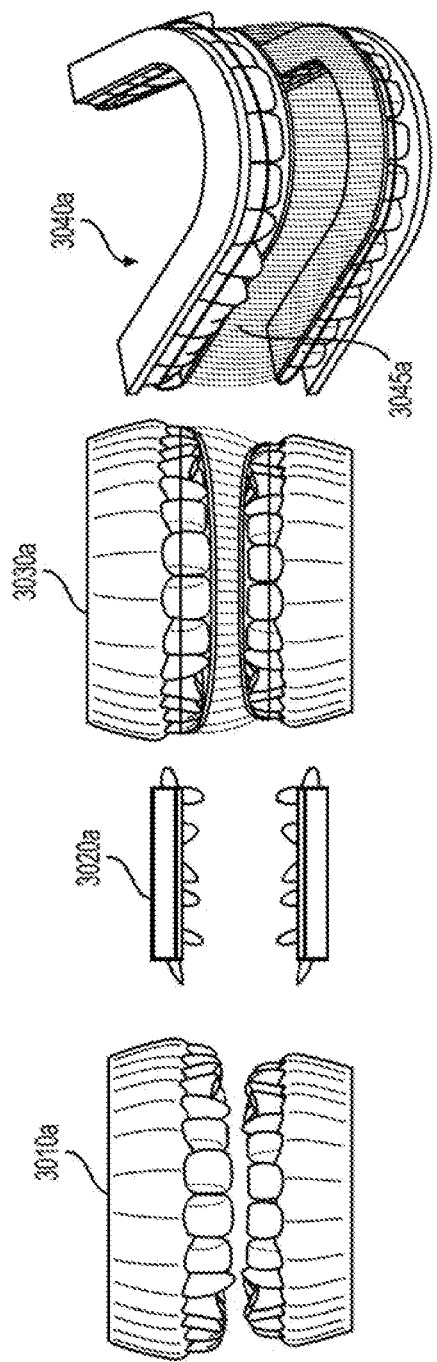
FIGS. 30A and 30B illustrate virtual retentive pieces being applied to virtual arches according to some example embodiments.
Figure 30B:
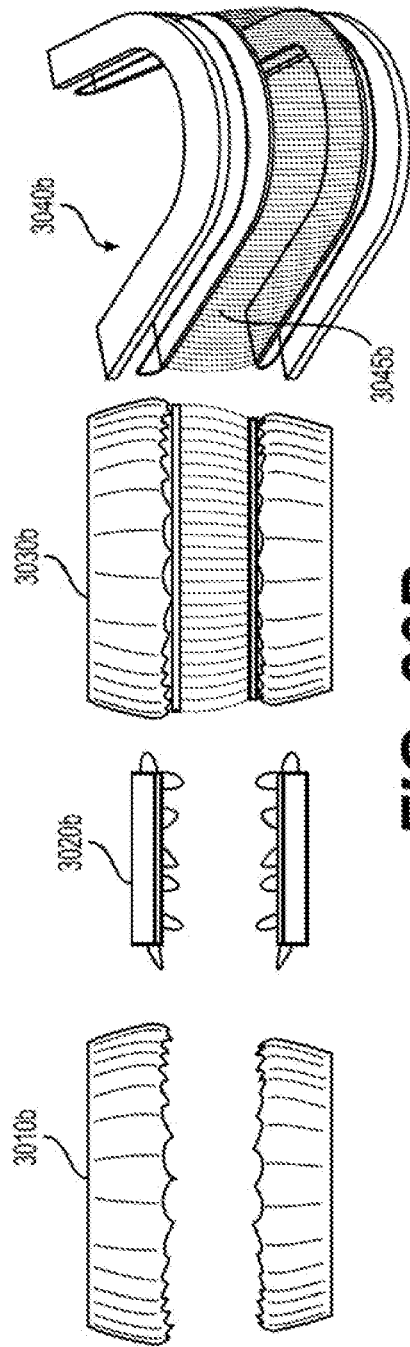

FIGS. 30A and 30B illustrate two non-limiting examples of potential surfaces of virtual retentive pieces partially defining an envelope region (3D region) by being placed on the guidance side surface of arches. FIGS. 30A and 30B illustrate circumstances in which only space (no tissue) exists between the virtual retentive pieces (a 3D region). As shown in FIGS. 24-27, 29, 30A and 30B, the guidance package system can use the virtual positions of a surface of, or the entire body of the retentive pieces for guidance package development, and attachment. The guidance package system can also use the virtual positions of different surfaces of the retentive pieces to define a space available (limited 3D region) for parametrical manipulation (mathematical calculation) of the movement and stop profile (FIGS. 30A-31D). For example, referring to FIG. 30A, a retentive piece may be in physical form or in virtual form represented by a planar curve that may or may not become a surface of a retentive piece.

When all the space is available between the retentive pieces 10 for producing guidance components for guidance equipped appliances or restorations, the tissue side 710 of the retentive pieces 10 will be in contact and attached to the guidance side surface of that arch. Examples of retentive pieces attached to the guidance side surface of the arch are shown in FIGS. 30A-30B.

FIG. 30A illustrates dentate mandibular and maxillary arches 3010*a*. Retentive pieces 3020*a* may be fitted (virtually) onto the arches 3030*a*. The boundary of the envelope region 3045*a* may be defined as the space between the retentive pieces 3040*a*. Guidance mechanisms may be entirely located between the retentive pieces, and may be combined with one or more retentive pieces to form a guidance equipped appliance, such as a bruxism appliance, a TMD appliance, a sleep apnea device, or a restoration. The guidance and stop features of the one or two piece appliance or restoration can be constructed between the retentive pieces FIG. 30A. The calculation for and the construction of a two piece appliance or restoration will include both the retentive pieces and the guidance and stop features for those respective retentive pieces, but in the case of a one piece appliance will involve only one actual physical retentive piece for the construction of that one arch solution (appliance or restoration).

FIG. 30B illustrates edentulous mandibular and maxillary arches 3010*b* onto which retentive pieces 3020*b* are placed

3030b. An envelope region 3045b is defined by the space between the retentive pieces 3040b, such that guidance mechanisms are entirely located between the retentive pieces, and when combined with the retentive piece(s) may form guidance equipped appliances (such as canine guidance or group function appliance or restoration). The guidance and stop features of the two piece appliance or restoration can be constructed between the retentive pieces. The calculation for and the construction of a two piece appliance or restoration will include both retentive pieces and the guidance and stop features for those respective retentive pieces, but in the case of a one piece appliance will involve only one actual physical retentive piece for the construction of that one arch solution (appliance or restoration).

Although retentive pieces are described with reference to FIGS. 30A and 30B, one of ordinary skill should recognize that this is merely an example. In some circumstances, an envelope region (3D region) may be defined by the tissue surfaces (e.g., teeth, gums), or some gap formed around the tissue surfaces.

There may be a circumstance regarding an arch or both arches that instead of all the guidance and stops and retentive pieces being located between the tissue of the two respective arches, some of the tissue may be included in an envelope region (virtual 3D region) and potentially be involved in the solution (appliance or restoration). In this circumstance, some portion of the patient's tissue may be modified, using, for example surgery. In one embodiment, an envelope region includes tissue that can be included in the movement profile development and calculation. A given arch may have a circumstance that the tissue of the arch may not be modified but can be included in the movement profile development and calculation. A given arch may have a circumstance that the tissue of the arch may be modified and must be included in the movement profile development and calculation. In a circumstance that the to-be-modified tissue in an arch should be involved with the movement profile development and calculation, an envelope region must be defined virtually (e.g., by applying planar curves or by placing a virtual retentive piece) in a location far enough into the tissue of that arch to include all parameterizations of the movement and stop profile and any potential retentive pieces the clinician intends to evaluate. In a circumstance that the not to be modified tissue in an arch should be involved with the movement profile development and calculation, an envelope region (3D region) must be defined to include the guidance side surface contact data of that arch. In either circumstance, the not to be modified arch or the to-be-modified arch may also have additional prosthetics or appliance(s) applied to achieve the correct movement profile (only some of the space is available between the planar curves that may or may not also represent potential surfaces of potential retentive pieces to be replaced by CAM produced appliances, or restorations).

In the circumstances where the clinician intends to modify tissue (e.g., alter a tooth) or utilize tissue within a solution, this space must be included within an envelope region (3D region) for the guidance package calculation. Further this space must be included in parametrical calculations to further refine the shape of guidance and stop profiles and any desired retentive pieces.

Therefore, if planar curve(s) are used to define a 3D region (envelope region), for the purpose of calculation on the arch or arches left unmodified, the planar curves can be placed virtually into the tissue of the arch far enough past the guidance side surface of the arch to include all contact information of that arch, thus making the contact information available for calculation and development of the movement and stop profile and any desired retentive piece. Similarly, for the purpose of calculation on the arch or arches to be modified, a virtual planar curve can be placed virtually into the tissue of that arch far enough past the guidance side surface of the arch to anticipate any potential guidance package derived modifications of that arch that the clinician intends to evaluate (e.g., to include areas that may be modified within a 3D region).

Examples are illustrated in FIGS. 31A-31E. In some circumstances, a global 3D region in which the space for all guidance package system parameterization (e.g., retentive piece(s), guidance package, and surgical, restorative, and implant placement guides) may be utilized. For example, planar curves or a tissue side surface 710 of a virtual retentive piece may provide boundaries to a global 3D region. In some cases, a subset of the global 3D space may be considered. For example, limited virtual 3D regions may also be defined and utilized for subset parameterizations of retentive pieces and/or guidance and stop package features, and/or surgical, restorative, implant placement guides and/or other considerations.

Figure 31A:
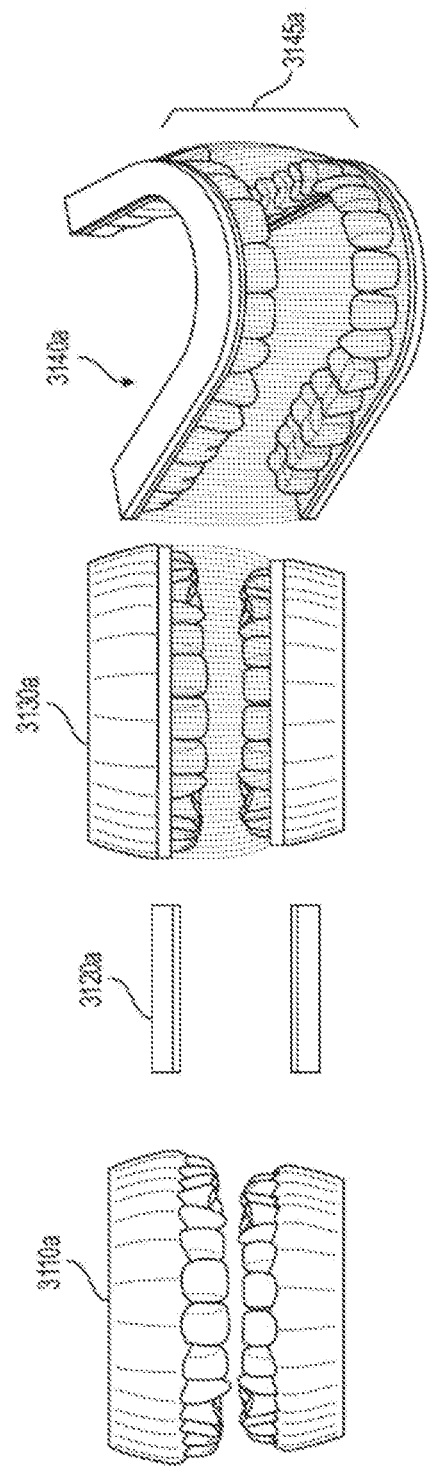
FIGS. 31A-31E illustrate virtual patient arches that feature virtual planar curves for 3D region calculation according to some example embodiments.

FIG. 31A illustrates two dentate arches 3110a in which the clinician intends to modify the tissue of both arches. Each respective virtual curve of the guidance side surface of a potential retentive piece 3120a is virtually located far enough into the tissue 3130a past the guidance side surface of its respective arch defining an envelope region (3D region) 3145a in 3140a in order to anticipate and later generate the parameterizations of the movement profile (and therefore the potential guidance package derived modifications of those arches) the clinician intends to evaluate. In this circumstance the clinician may generate guidance package derived restorative guides (for example, as illustrated in FIG. 35E) to modify those teeth with adjustments, crowns, bridges, removable partial dentures or other prosthetics that have guidance and stops derived from the guidance package system.

Figure 31B:
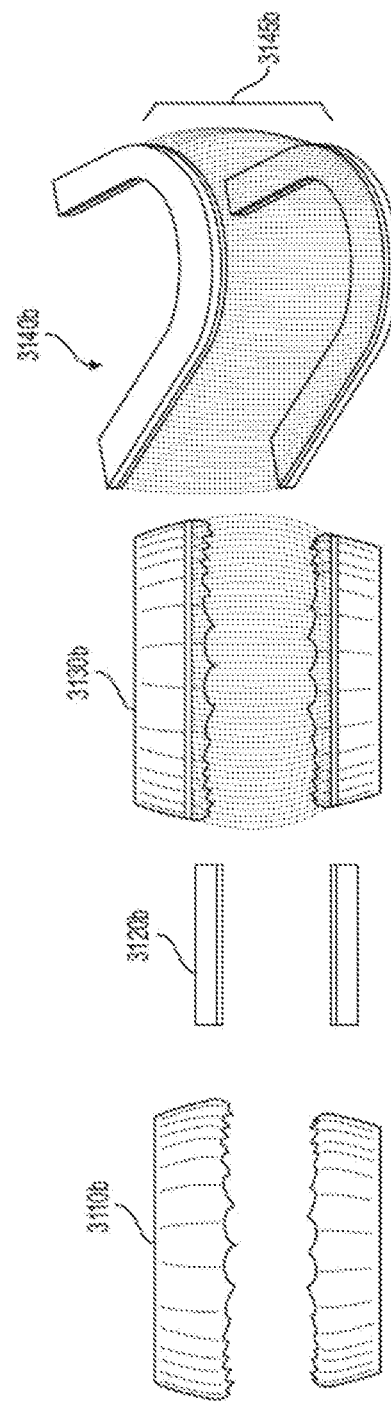

FIG. 31B illustrates with two edentulous arches 3110b in which the clinician intends to modify the tissue of both arches. Each respective virtual curve of a guidance side surface of a potential retentive piece 3120b is virtually located far enough into the tissue 3130b past the guidance side surface of its respective arch defining an envelope region 3145b in 3140b in order to anticipate and later generate the parameterizations of the movement profile (and therefore the potential guidance package derived modifications of those arches) the clinician intends to evaluate. In this circumstance, the clinician may generate guidance package derived surgical guides (for example, as illustrated in FIG. 35F) to modify those tissues using surgery and other techniques to add or remove tissue. Using the information from the guidance package system with the virtual curves of the potential retentive pieces in these locations can produce implant placement surgical guides (for example, as illustrated in FIG. 35G) that enable the clinician to place implants at angulations indicated understanding the forces of occlusion.

Figure 31C:
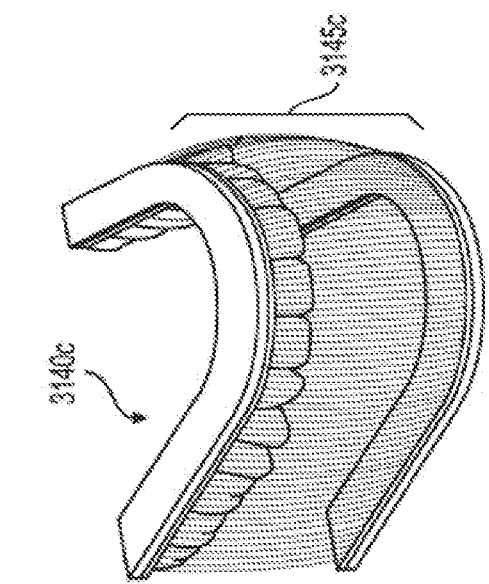
Figure 31C:
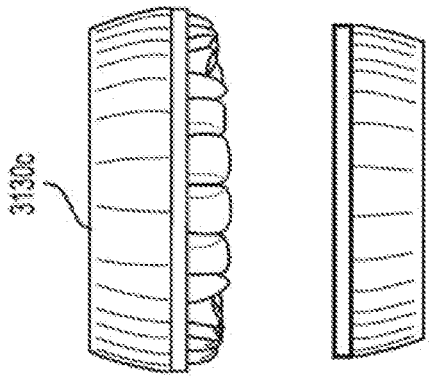
Figure 31C:
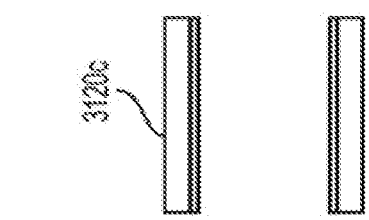
Figure 31C:
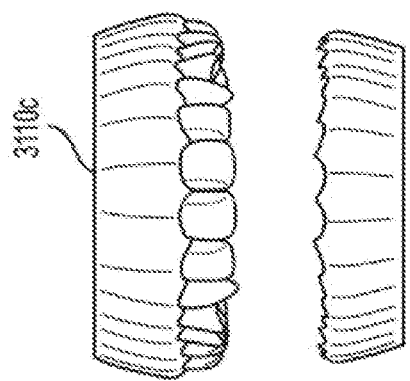

FIG. 31C illustrates a dentate arch opposing an edentulous arch 3110c. In this example, the clinician places the virtual curve of a guidance side of the potential virtual retentive piece 3120c on the dentate arch into the tissue past the guidance surface of 3130c, and places the virtual curve of the guidance side surface of the virtual retentive piece 3120c on the guidance surface of the edentulous arch 3130c. In this case, an envelope region 3145c, as shown in 3140c, is defined by the guidance surface of the retentive piece virtually placed on the edentulous arch and the planar curve embedded into the tissue of the dentate arch in order to anticipate and later generate the parameterizations of the movement profile (and therefore the potential guidance package derived modifications of the dentate arch) the clinician intends to evaluate. A guidance package solution may include a derived restorative guide and a guidance equipped retentive piece. The guidance package equipped printed mandibular retentive piece may involve a different 3D region that includes both the calculation and parameterization of the retentive piece and calculation and parameterization of the guidance package features to be combined with that retentive piece. The physical retentive piece may utilize implants as the attachment mechanism to the tissue of the mandibular arch.

Figure 31D:
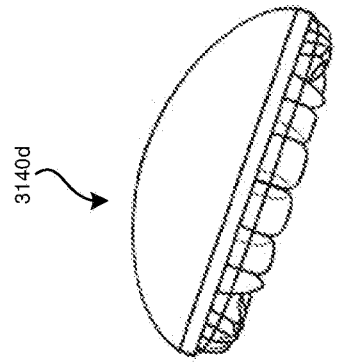
Figure 31D:
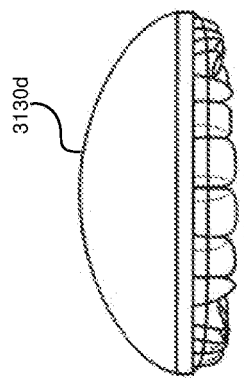
Figure 31D:
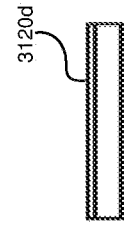
Figure 31D:
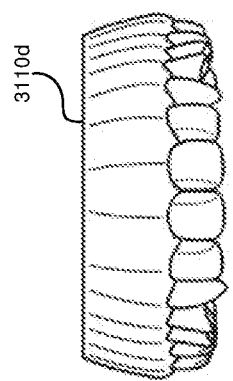

FIG. 31D illustrates a dentate arch 3110d with a potential virtual retentive piece 3120d placed thereon into the tissue 3130d, and utilizes the virtual curve of the tissue side surface 3140c to define a boundary of a 3D space for parameterization.

Figure 31E:
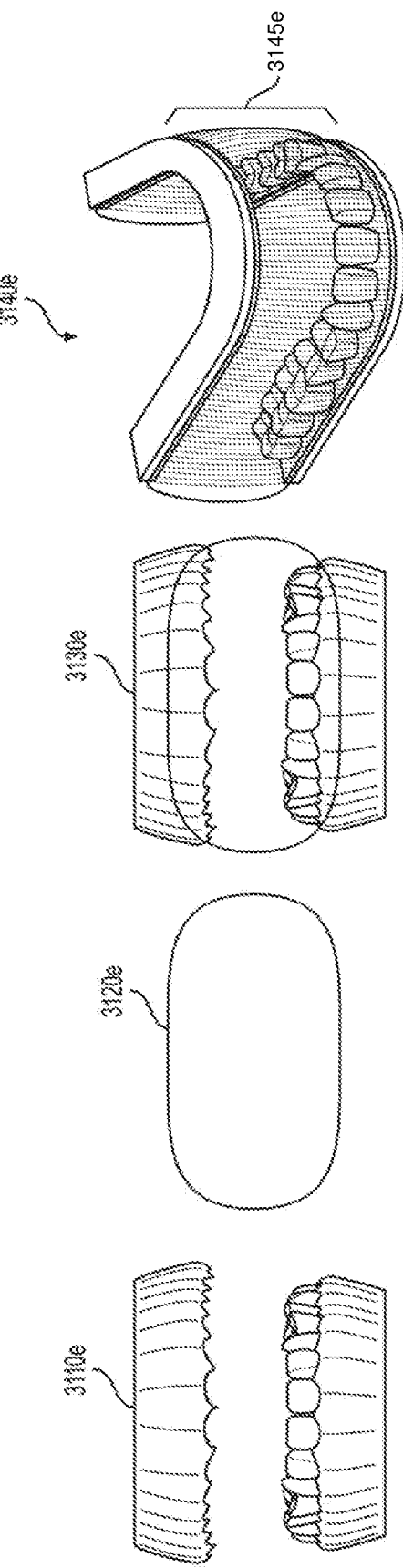

FIG. 31E illustrates an edentulous arch opposing a dentate arch 3110e. In this example, the clinician places a boundary of a 3D region using curves 3120e past the tissue 3130e of the arches, to define a 3D space 3145e without the use of virtual retentive pieces 3140e.

In some circumstances, the clinician may produce, from the parametric determination made of guidance and stops from an envelope of parametric choices, a restorative guide or stent to modify the dentate arch using adjustments, crowns, bridges or other prosthetics and also a printed opposing corollary restoration for the edentulous arch. All the surfaces (of the adjusted teeth or tissue, or not adjusted teeth or tissue and prosthetics of the modified arch and all the surfaces of the printed corollary restoration for the edentulous arch) of guidance and stops and retentive piece(s) can be derived from or included in the parametrical calculation of the guidance package system.

In some circumstances, an envelope region (virtual 3D region) for mathematical manipulation of the shape of the guidance profile and retentive piece(s) does not involve any tissue, may include only contact surface data of the arch, or may include the tissue past the guidance side surface of that arch. Accordingly, parameterizations of the movement profile (and therefore the potential guidance package derived modifications of that arch) the clinician intends to evaluate may include tissue, include only a surface of the tissue, or exclude all tissue from a given arch. On any given arch, an operator may provide, based on this data, appliances, restorations, restorative guides, surgical guides, and/or implant placement guides.

One of ordinary skill will understand that the dentate arch and the edentulous arch may be either a mandibular arch or a maxillary arch. It will also be understood that the examples in FIGS. 31A-E are non-limiting, and an envelope region may be variously defined to include or exclude various portions of tissue or tissue guidance side surfaces.

Figure 32:
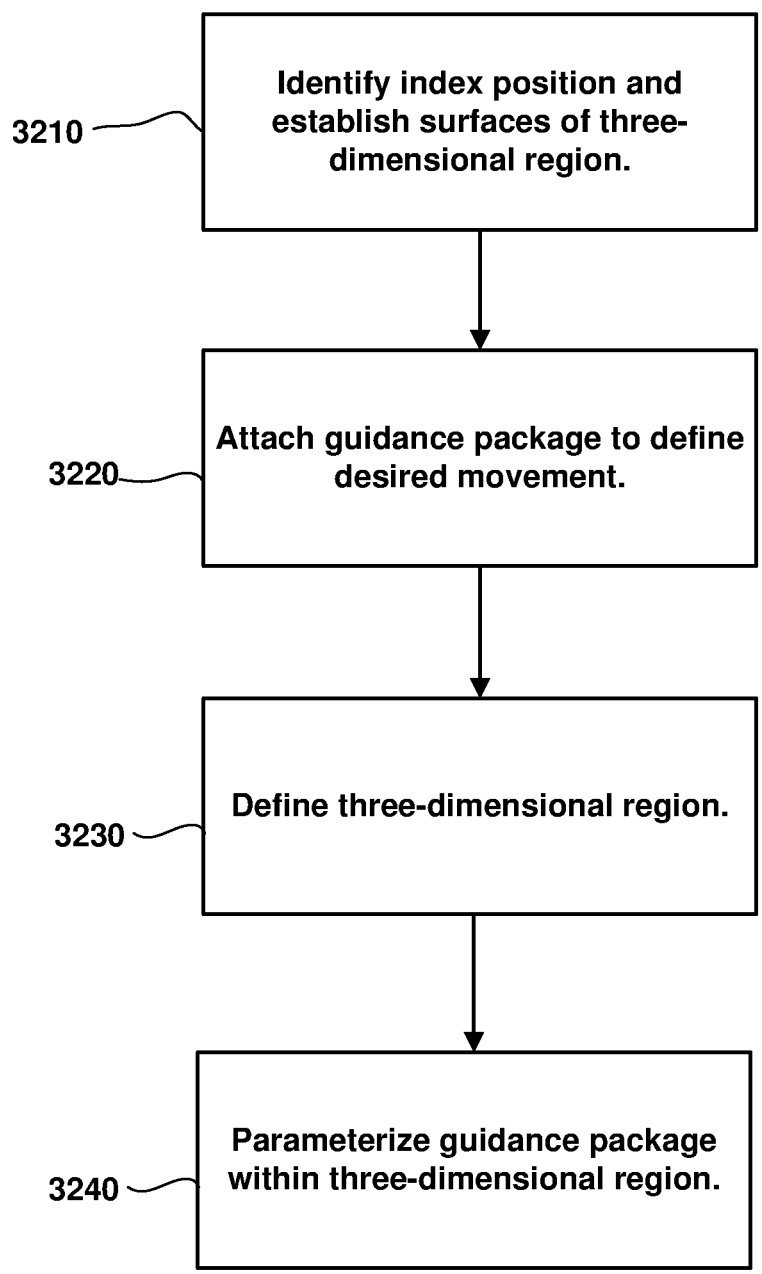
FIG. 32 is a flowchart of a method of developing a guidance solution according to an example embodiment.

FIG. 32 is a flowchart of a method 3200 in accordance with some embodiments of the present disclosure. An appropriate index position of the mandible in relation to the maxilla for a particular patient for a particular solution (e.g., a prescribed maximum closure position) is identified 3210. The appropriate canonical guidance package (movement and stop profile) for the solution is specified 3220. The canonical guidance package may be a virtual representation and/or a mathematical object. Using patient specific data (or average, generic, or other data) the canonical guidance package is sized, indexed into position, adjusted, and attached. A 3D region is defined 3230 within the model. For example, curves defining boundaries of the 3D region (e.g., planar curves, surfaces of retentive pieces, tissue surfaces, or internal portions of the surfaces) may be established, and a geometric shape of an arch form that comports to that patient's skeletal frame of maxilla and mandible is formed between the virtual curves of the retentive pieces at the prescribed index position. It will be understood that the 3D region and its boundaries may be determined at different times (e.g. before or after application of the guidance package and before or after identifying the index position) and in various manners. Finally, the method includes parameterizing 3240 the guidance package and/or additional guidance solution functions (e.g., retentive pieces or restorative guides) within a 3D region to establish one or more solutions for implementing a customized guidance profile of the patient's mandible.

Figure 33:
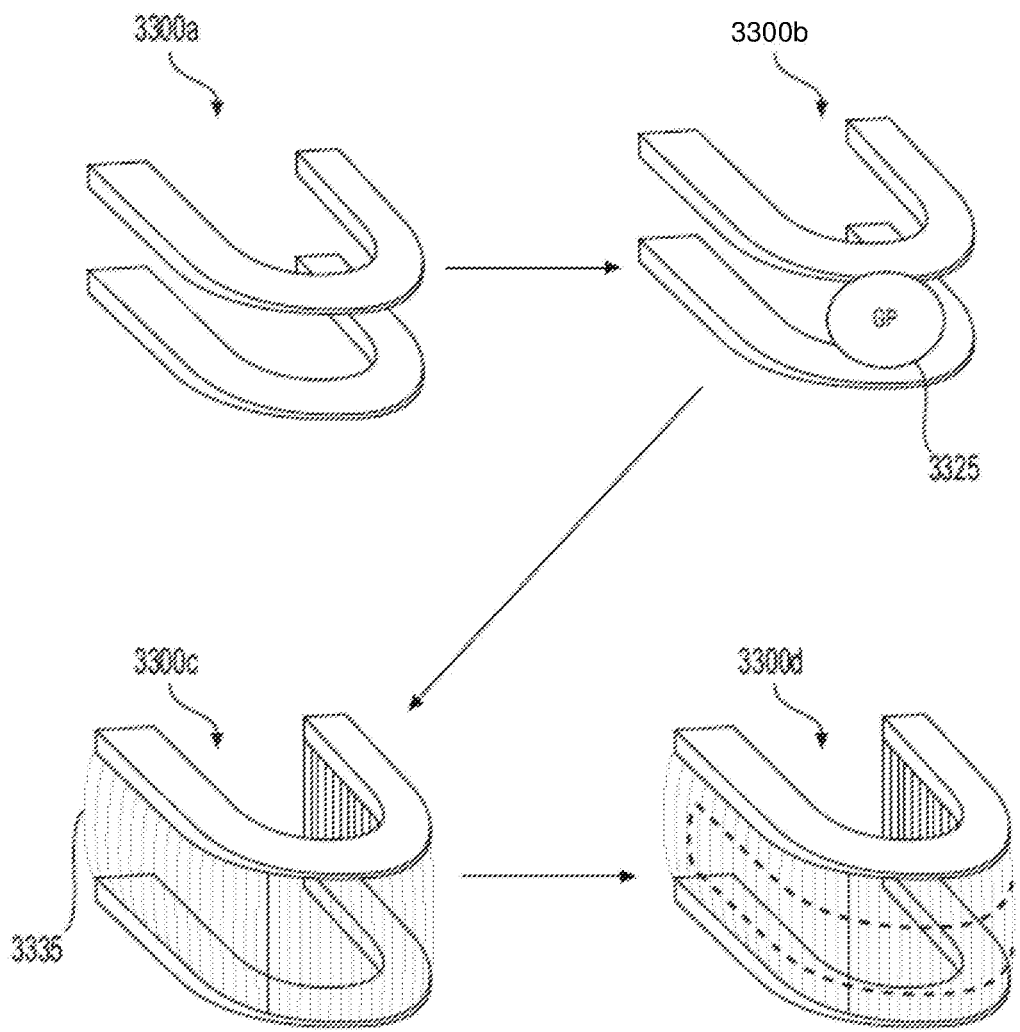
FIG. 33 illustrates developing of a guidance package according to an example embodiment.

FIG. 33 illustrates an example application of the method discussed with reference to FIG. 32. In 3300-a FIG. 33, an index position is identified (3210). 3300-b illustrates a guidance package 3325 ("GP") virtually applied (3220) to define a desired movement. The guidance package may be applied as, for example, a geometric object or a mathematical description of movement. 3300-c illustrates an envelope region (3D region) 3335 being defined (3230). For example, bounds of the envelope region may be set based on an application of one or more virtual retentive pieces or surfaces of retentive pieces, although this is merely an example. In some cases, the bounds of an envelope region may include the surface of tissue (e.g., teeth), or extend into tissue. For example, a geometric shape of an arch form that comports to that patient's skeletal frame of maxilla and mandible is formed between the surfaces of virtual retentive pieces at the prescribed index position.

3300-d illustrates that a customized guidance and stop profile is developed from within the envelope region 3335. This may be accomplished by parameterizing (3240) the applied guidance package and/or the retentive pieces within the envelope region. By parameterizing the space, an envelope within which the areas, volumes, and the topography of the contact surfaces of the guidance and stop components can now be changed in concert with each other in a way that maintains the customized movement and stop profile derived from the indexed, sized, adjusted and attached appropriate guidance package. This can form the desired appliances and restorations. According to some embodiments, any guidance or other mechanisms (e.g., implants, retention pieces, tissue surfaces) of the final solution must fall within the bounds of an envelope region. In some cases, the guidance surfaces of the final solution must fall within the bounds of an envelope region.

Figure 34:
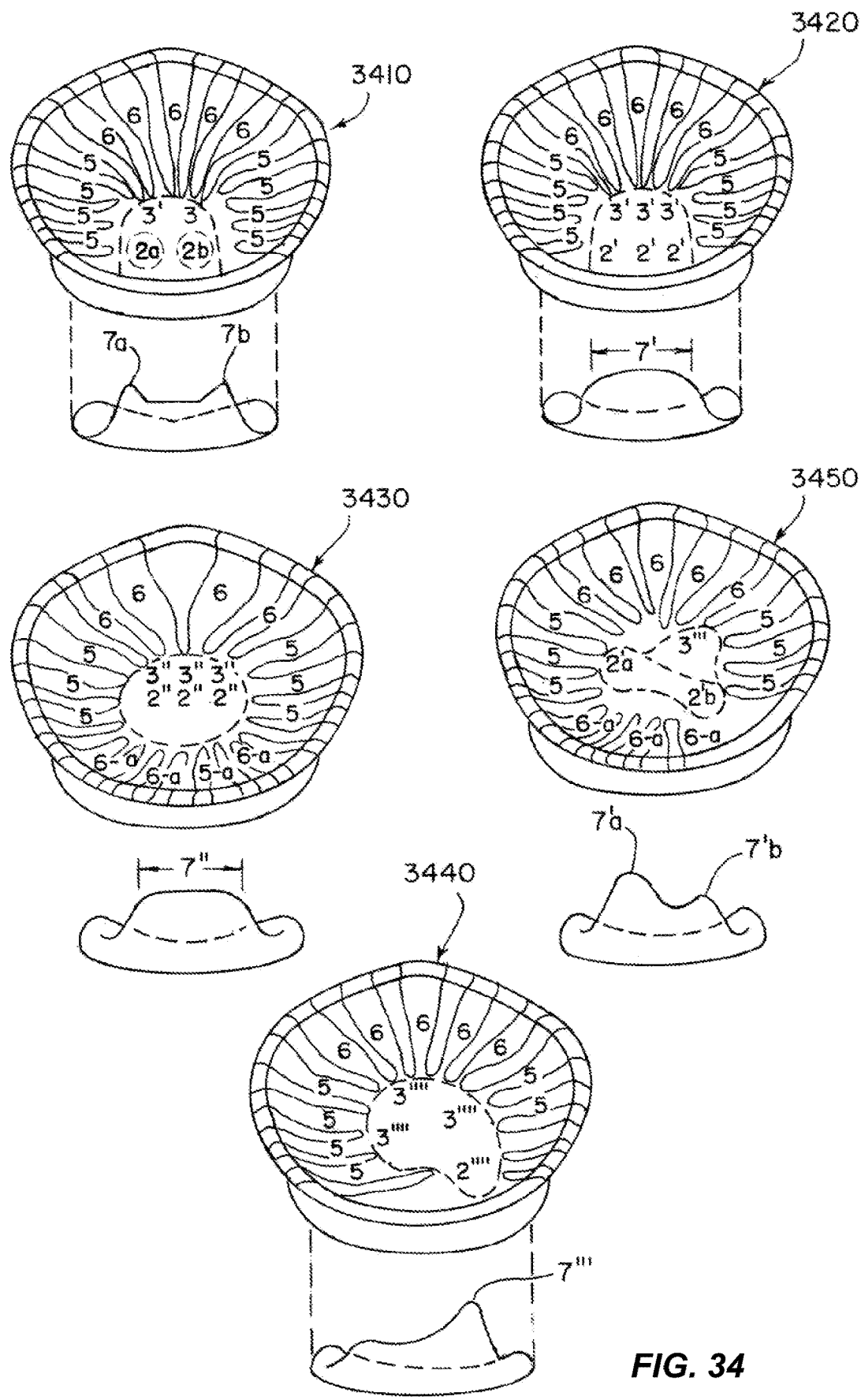
FIG. 34 illustrates guidance packages according to some example embodiments.

FIG. 34 illustrates visual representations of five guidance and stop profiles (guidance packages). Canine Guidance 3410 and Group Function Guidance 3420 packages are movement and stop profiles that are often expressed in the teeth and arches of the stomatognathic systems of the human population. It has been observed and noted by dentists that these guidance and stop patterns can provide to that particular person "normal" or "ideal" guidance and function in the context of the neuromuscular system of the stomatognathic system. Bilateral anterior repositioning 3430, Asymmetric 3440, and Asymmetric protrusive 3450 guidance packages are movement and stop profiles that are generally not expressed in the stomatognathic systems of human beings. These guidance and stop profiles may be applied to provide therapeutic scenarios of function to include sleep apnea and TMD. These movement and stop profiles have been observed and noted by dentists to provide successful therapies (e.g., TMD and sleep apnea) in the context of the neuromuscular system of the stomatognathic system. The physical representations of FIG. 34 are for explanation purposes only. In some cases, these guidance and stop profiles may be virtually represented and applied to a virtual articulator.

One of ordinary skill will understand that motion defined by guidance and stop profiles (e.g., 3410-3450) may be represented as geometric or mathematical functions, which may be applied to a virtual representation of a patient's arches. In both situations, the guidance and stop profiles may only define requirements of ultimate solutions (e.g., a path that must be followed), but not define the ultimate solutions (e.g., whether the solution includes one or more of a restorative guide, a surgical guide, a retentive piece, or tissue surfaces). For example, the customized movement profile may be understood as a mathematical object and a 3D region (envelope region) available for manipulation of the mathematical object, a continuum within this envelope of other parameterized synergistic shapes (e.g., shapes that work together to guide the mandible along the prescribed path) can be mathematically derived that will allow final product considerations and other patient considerations.

Figure 35A:
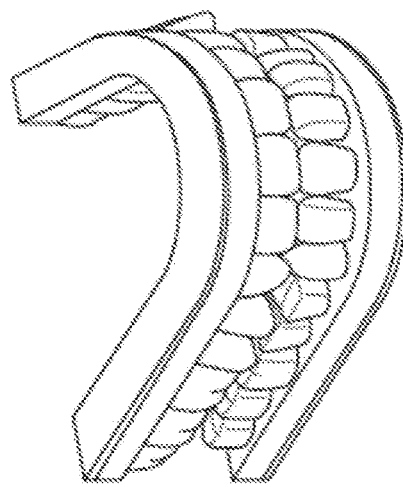
FIGS. 35A-35G illustrate patient solutions developed according to certain example embodiments.
Figure 35B:
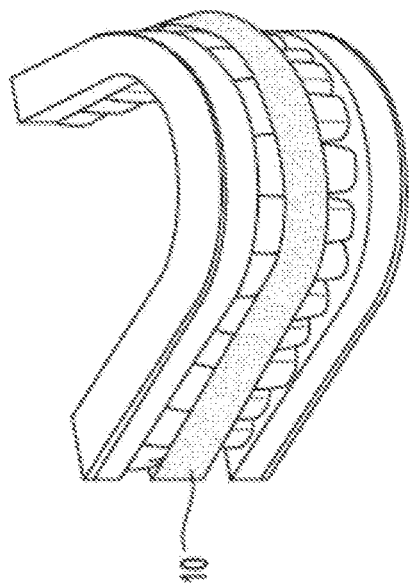
Figure 35C:
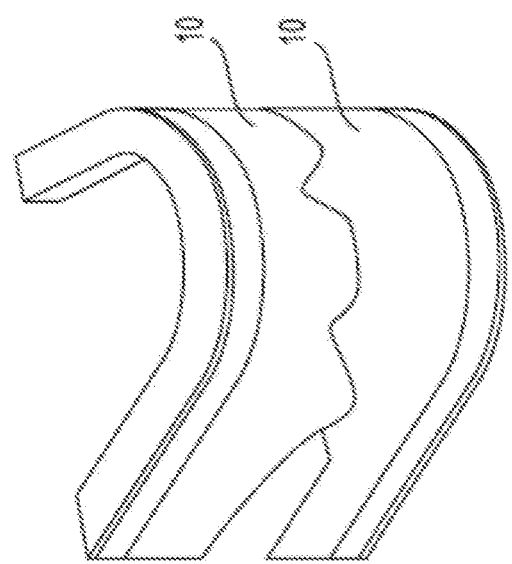
Figure 35C:
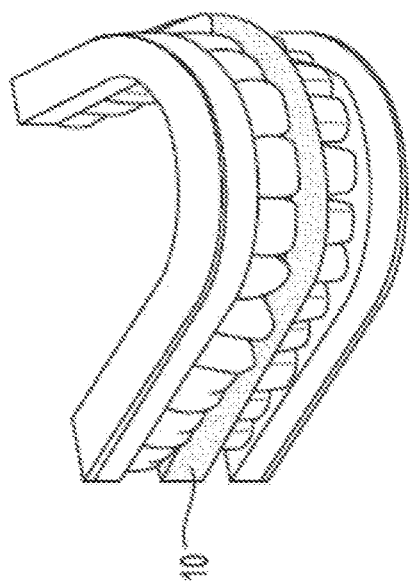
Figure 35D:
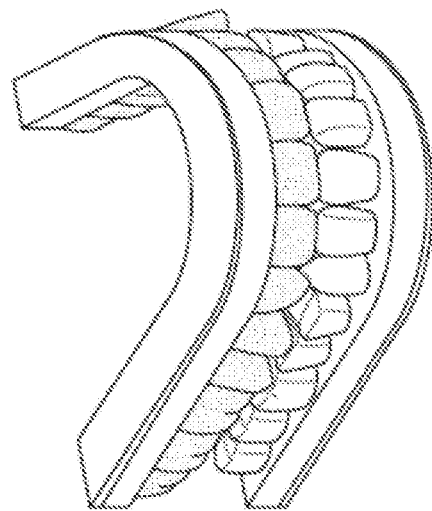
Figure 35D:
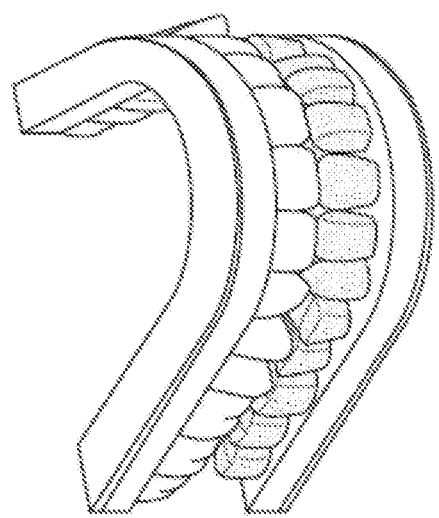
Figure 35E:
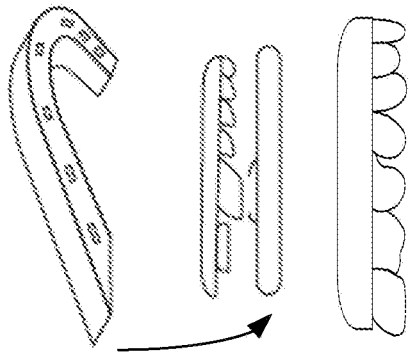
Figure 35G:
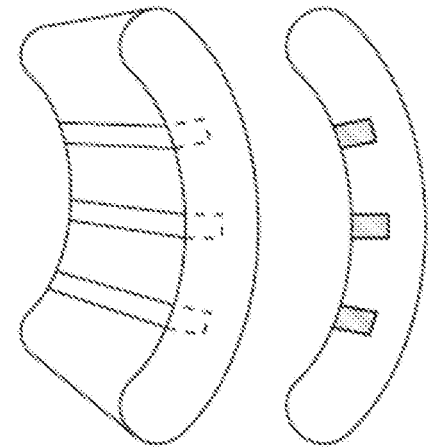
Figure 35F:
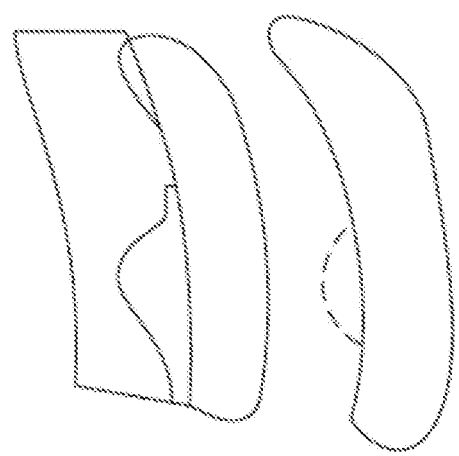

From the continuum of parametrical possibilities a clinician may produce many different one or two arch solutions as shown in FIGS. 35A-35G. FIG. 35A illustrates a solution with two-arch retentive pieces 10 in accordance with various embodiments of the present disclosure. In this case, surfaces of the retentive pieces 10 are designed to interact in guiding the mandible to the index position. In some circumstances, a two-arch solution can be used to treat bruxism, TMD, sleep apnea, and other conditions. FIG. 35B illustrates a solution with two-arch restoration in accordance with various embodiments of the present disclosure. The restorations may include dentures, modified natural teeth or other tissue, unmodified natural teeth or other tissue, crowns, bridges, removable partial dentures, other fixed prosthetics, other removable prosthetics, and combinations thereof. In the two-arch restoration, the surfaces of the various components (e.g., dentures, artificial teeth, and natural teeth) are designed to interact to guide the mandible into the index position. FIG. 35C illustrates solutions with one-arch retentive piece 10 in accordance with various embodiments of the present disclosure. In this case, surfaces of the retentive piece 10 are designed to interact with tissue surfaces on the opposing arch in guiding the mandible to the index position. FIG. 35D illustrates solutions with one-arch restoration in accordance with various embodiments of the present disclosure. In the one-arch restorations, the surfaces of the various components (e.g., dentures, artificial teeth, and natural teeth) are designed to interact with the tissue in the opposing arch to guide the mandible into the index position.

FIGS. 35E-35G illustrate a guidance package derived restorative guide FIG. 35E, a surgical guide FIG. 35F, and an implant placement guide FIG. 35G in accordance with an example embodiment of the present disclosure. Surgical guides FIG. 35F could include major arch shape change stents/guides for a surgeon to aid in the manipulation of bone, sinus, gum and other tissues of the arch, or more conservatively a custom full arch restorative guide FIG. 35E with breaks or openings to indicate adjustment points for existing dentition or prosthetics. A restorative guide FIG. 35E can be used in the case where a clinician may want to modify the arch form to be consistent to a guidance package solution to include teeth, and/or other tissue, and/or existing prosthetics. A surgical guide FIG. 35F can be used in the case where a clinician may want to surgically modify the arch form to be consistent to a guidance package solution to include teeth, and/or bone, and/or gum, and/or other tissue, and/or existing prosthetics. For example, one of these classes of material, e.g., bone, may be modified, e.g., the mandible is modified, such that the resulting shape of that arch allows the application of the determined parameterization. An implant placement guide FIG. 35G can be used in the case where a clinician may want to place implants at appropriate angulations according to the arch form according to a guidance package solution to include one or both arches. For example, it may be desirable to use an implant placement guide to create the appropriate angles of implant placement for a specific curve of Spee and Wilson, respectively or relative to the angles of occlusion (See, e.g., FIGS. 44A-44B).

Figure 36A:
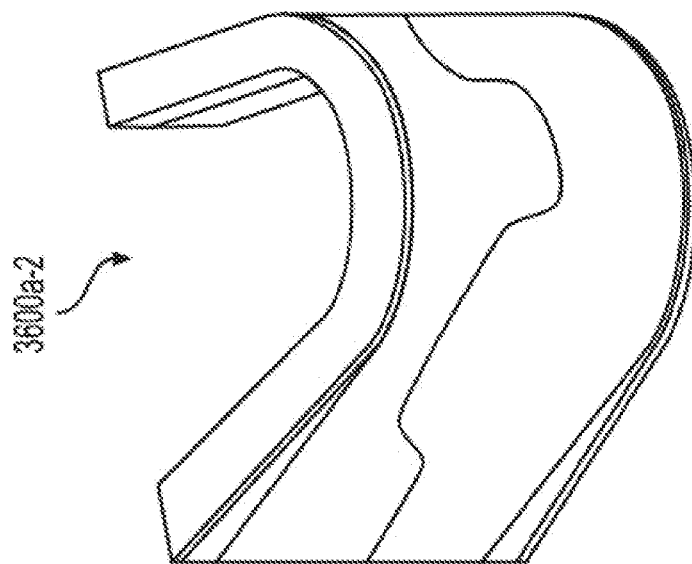
FIGS. 36A-42 illustrate different solutions from example guidance packages according to some example embodiments.
Figure 36A:
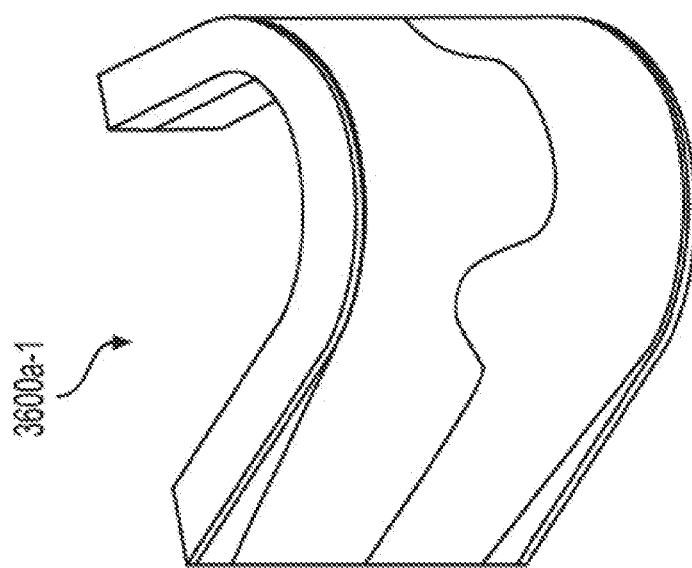
Figure 36B:
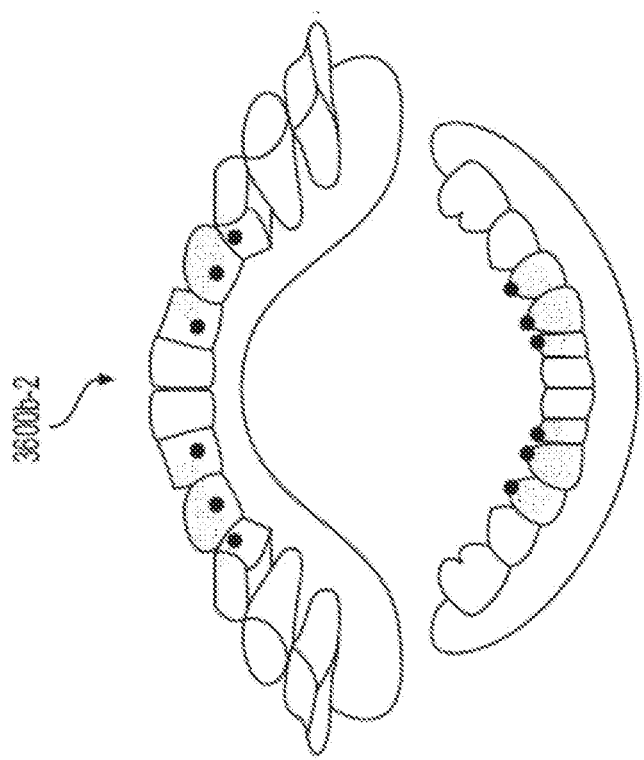
Figure 36B:
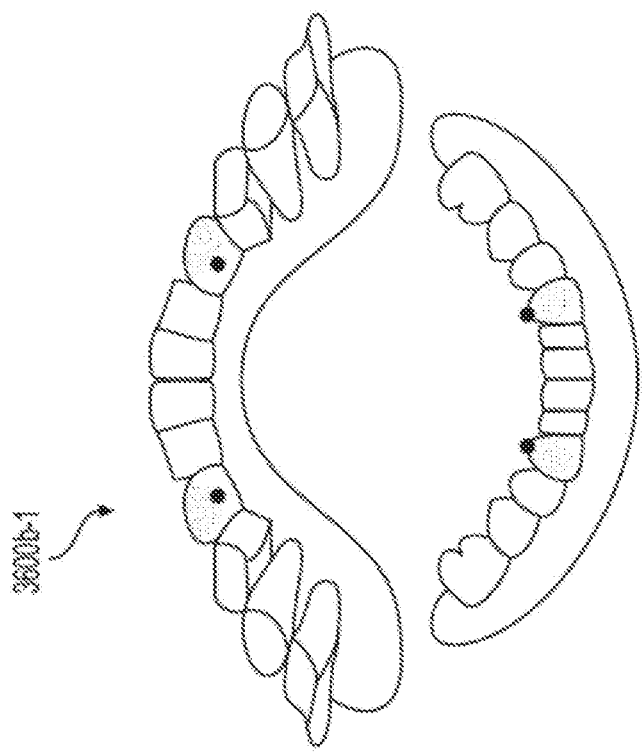

FIGS. 36A and 36B illustrate example final solutions where a canonical canine guidance package (e.g., 3410 of FIG. 34) in accordance with some embodiments of the present disclosure is applied, for example, using the method described with reference to FIGS. 32 and 33. Referring to both 36A and 36B, boundaries of an envelope region can be defined, the index position may be identified (e.g., a centric relation at appropriate vertical dimensions), the canonical canine guidance package is customized for the patient (sized, indexed, adjusted, and positioned virtually), creating a customized movement and stop profile. This may be considered, for example, a geometrical object. An envelope region may be defined by the available space between the boundaries, and then customized movement and stop profile can be parameterized within the envelope region to create solutions. In some cases, the form of the solution may be based on whether the arches are dentulous, edentulous, or partially edentulous. In some cases, a form of solution may be selectable, for example, by a dentist or clinician or operator of the system. It will be understood that the final solution may be, for example, an appliance solution, arch reconstruction, restoration, rehabilitation, and/or optimization, or some combination of the proceeding.

Referring to FIG. 36A, in a case where both mandible and maxilla are dentulous, partially edentulous or other, the parameterization may result in one or more designs for a two-piece appliance. Each appliance piece could be inserted over a corresponding arch and the surfaces of the appliances would interact to control the customized movement and stop profile. For example, 3600a-1 and 3600a-2 illustrate two possible customized solutions. In 3600a-1, the two-piece appliance is characterized by guidance located in the canine areas. In comparison, 3600a-2 is characterized by guidance centered in the canine areas of the retentive pieces with broader contact areas. One of ordinary skill will recognize that 3600a-1 and 3600a-2 represent just two examples from within a parametrical continuum of different shapes that would control a same customized guidance and stop profile to the index position for the patient. The final appliances may be smoothly flowing plastic (or other material) shapes that have a certain geometry to include the contact surfaces (guidance and stops) that may appear very different from the canonical canine guidance package, but with shapes determined from within an envelope of possibilities mathematically derived from the sized, indexed, adjusted and attached canine guidance package and will feature the same movement and stop profile.

Referring to FIG. 36B, in a case where both mandible and maxilla are edentulous, the parameterization may result in one or more designs for a two-piece restoration. These guidance package derived restorations may serve to guide the patient's mandible utilizing the surfaces of the replacement dentition (i.e., the false teeth) to interact to control the customized movement and stop profile. The edentulous circumstance (FIG. 36B) may provide a greater envelope region than the dentulous (FIG. 36A), as the natural teeth would not serve as a barrier. As non-limiting examples of edentulous solutions, 3600b-1 and 3600b-2 illustrate two possible customized solutions. In 3600b-1, the two-piece restoration is characterized by a certain complement of stops (dots) and guidance (shading) located on the prosthetic teeth and angulations of the prosthetic teeth to perform the guidance. In comparison, 3600b-2 is characterized by a different complement of stops and guidance located on the prosthetic teeth and angulations of the prosthetic teeth to perform the guidance. For example, if the index position is centric relation at an appropriate vertical dimension, the stops, guidance, and angulations may be consistent with ideal canine guidance. One of ordinary skill will recognize that 3600b-1 and 3600b-2 represent just two examples from within a parametrical continuum of virtual morphing shapes of dentate arches in synergy that would control a same customized guidance and stop profile to the index position for the patient. The final restoration(s) may be of materials that mimic patient tissue in certain geometric shapes to provide the same movement and stop profile as derived from the sized, indexed, adjusted and attached canine guidance package. The mimicked tissue can include very different shapes from the canonical canine guidance package, but the shapes are chosen from within an envelope of possibilities of canine guidance restorative choices mathematically derived from that guidance package to feature that same movement and stop profile.

It will be understood that the stomatognathic system includes a neuromuscular system. In some cases, neuromuscular considerations should be included when considering different parameterizations (e.g., solutions) of a movement and stop profile for either an appliance or a restoration. It the context of the stomatognathic system, different synergistic shapes of the same movement profile may produce different responses from the neuromuscular system. For example, the neuromuscular system reacts differently for stress placed on the posterior teeth as compared to stress placed on anterior teeth, and, therefore, may react differently to guides and stops anchored near the posterior teeth as compared guides and stops anchored anteriorly. An operator may use different parameterizations of the same movement and stop profile to utilize different areas of the arches for guidance and stops to provide different neuromuscular responses. These considerations may be included in the customization of the guidance package before or after parameterization. Using a system or method according to the present disclosure may therefore provide greater flexibility and range of options over the related art. Neuromuscular considerations may influence a selection of parameterization for various guidance profiles both disclosed herein and as would be known by one of ordinary skill.

Figure 37A:
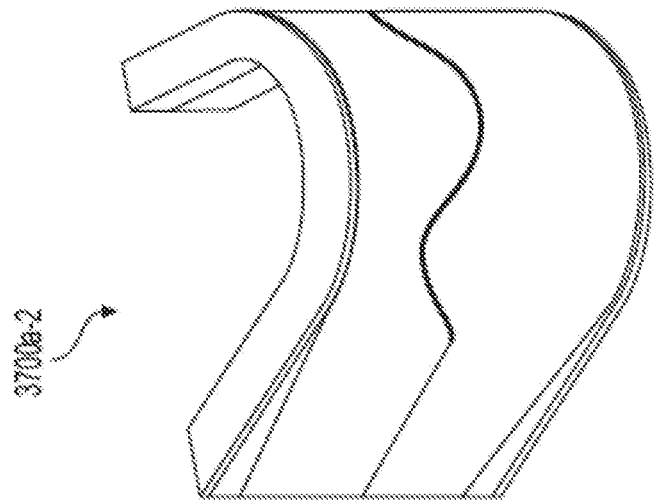
Figure 37A:
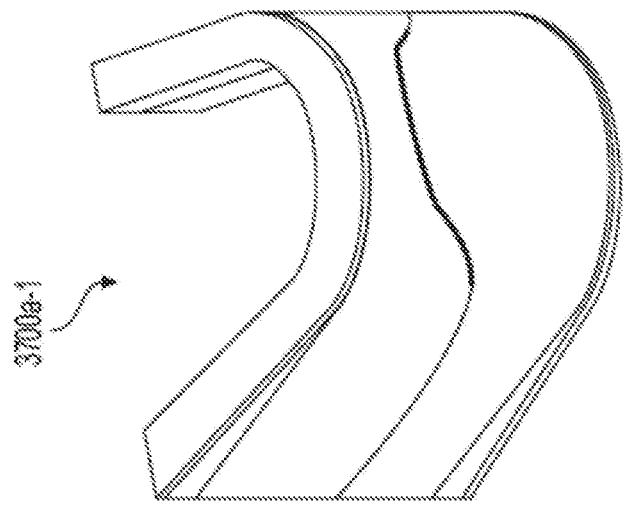
Figure 37B:
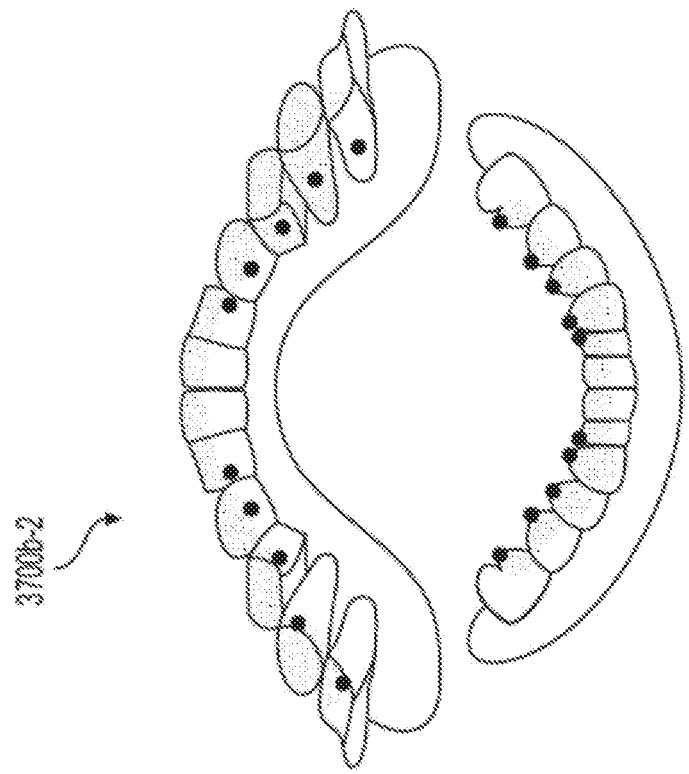
Figure 37B:
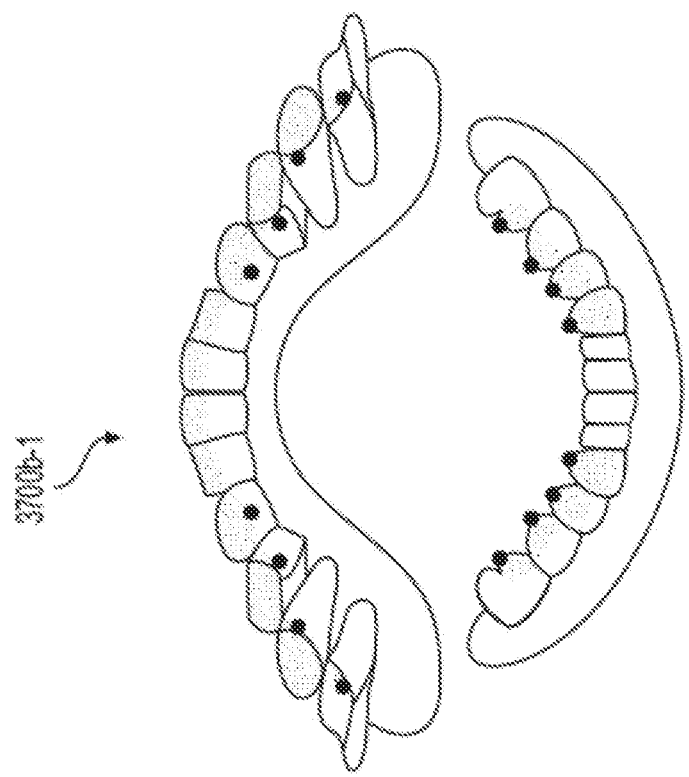

FIGS. 37A and 37B illustrate example final solutions where a canonical group function guidance package (e.g., 3420 of FIG. 34) in accordance with some embodiments of the present disclosure is applied, for example, using the method described with reference to FIGS. 32 and 33. The method may be implemented substantially similar to that described above with Reference to FIGS. 36A and 36B, and thus a description will not be repeated here for compactness. It will be understood that the final solution may be, for example, an appliance solution, arch reconstruction, restoration, rehabilitation, and/or optimization, or some combination of the proceeding.

Referring to FIG. 37A, in a case where both mandible and maxilla are dentulous, partially edentulous, or other, the parameterization may result in one or more designs for a two-piece appliance (e.g., a two-piece bruxism appliance). Each appliance piece could be inserted over a corresponding arch and the surfaces of the appliances would interact to control the customized movement and stop profile. For example, 3700a-1 and 3700a-2 illustrate two possible customized solutions within a parametrical continuum of different shapes that would control a same customized guidance and stop profile to the index position for the patient. In 3700a-1, the two-piece appliance is characterized by guidance located primarily in the midline. In comparison, 3700a-2 is characterized by guidance that extends further into the posterior areas of the appliance. The clinician may consider neuromuscular implications of different parameterizations when making a determination. The final appliances may be smoothly flowing plastic (or other material) shapes that have a certain geometry to include the contact surfaces (guidance and stops) that may appear very different from the canonical group function guidance package, but with shapes determined from within an envelope of possibilities mathematically derived from the sized, indexed, adjusted and attached group function guidance package and will feature the same movement and stop profile.

Referring to FIG. 37B, in a case where both mandible and maxilla are edentulous, the parameterization may result in one or more designs for a two-piece restoration. The guidance package designed restorations may serve to guide a patient's mandible to the index position using surfaces of the replacement dentition (i.e., the false teeth) to interact to control the customized movement and stop profile. As non-limiting examples of edentulous solutions, 3700b-1 and 3700b-2 illustrate two possible customized solutions within a parametrical continuum of virtual morphing shapes of dentate arches in synergy that would control a same customized guidance and stop profile. In 3700b-1, the two-piece restoration is characterized by a certain complement of stops (dots) and guidance (shading) located on the prosthetic teeth and angulations of the prosthetic teeth to perform the guidance consistent with the customized profile. Meanwhile, 3700b-2 is characterized by a different complement of stops and guidance located on the prosthetic teeth and angulations of the prosthetic teeth to perform the guidance. For example, the stops, guidance, and angulations may be consistent with ideal group function guidance. The final restoration(s) may be of materials that mimic patient tissue in certain geometric shapes to provide the same movement and stop profile as derived from the sized, indexed, adjusted and attached group function guidance package. The mimicked tissue can include very different shapes from the canonical group function guidance package, but the shapes are chosen from within an envelope of possibilities of group function guidance restorative choices mathematically derived from that guidance package to feature that same movement and stop profile.

Figure 38A:
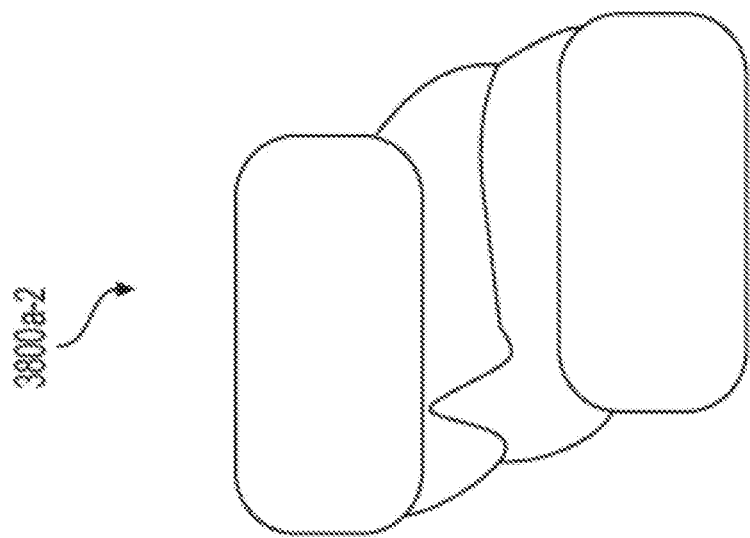
Figure 38A:
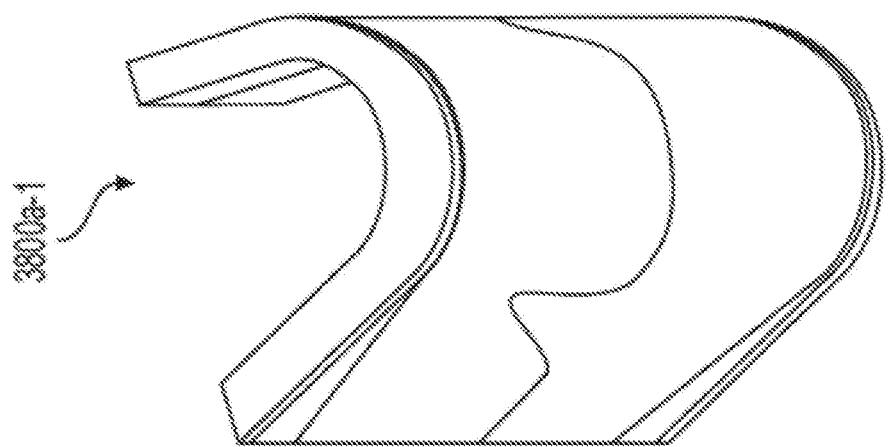
Figure 38B:
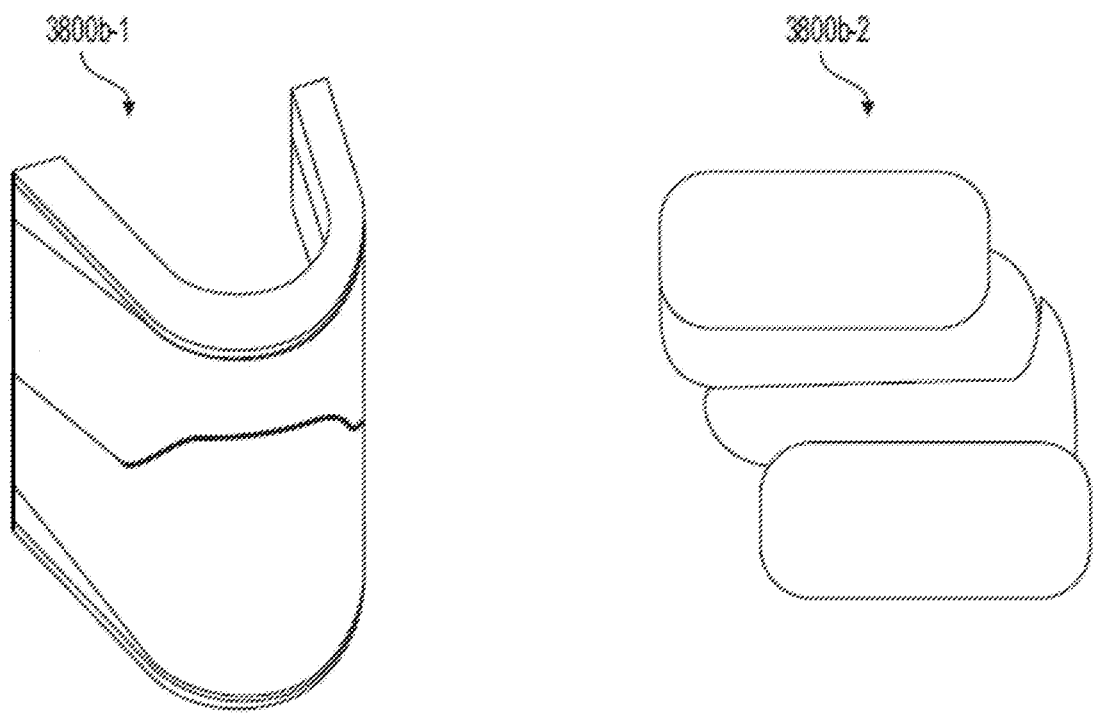

FIGS. 38A and 38B illustrate example final solutions where an asymmetric guidance package (e.g., 3440 of FIG. 34) in accordance with some embodiments of the present disclosure is applied, for example, using the method described with reference to FIGS. 32 and 33. In one example, a two piece TMD (TMJ Dysfunction) appliance may be planned for a dentate patient, and the index position may be the prescribed respective asymmetric index positions for that particular patient and that particular purpose. A canonical asymmetric guidance package is customized (e.g., sized, indexed, adjusted, and attached) to the retentive pieces, such that it is now customized for that patients' data and can be defined as a geometrical object. The data for this particular patient could include specific TMD (TMJ dysfunction) data. This data could be collected through the use of clinical evaluation, 3D x-ray, a Jaw Motion Analyzer (e.g., as illustrated in FIG. 14), or other methods. This data could influence envelope region(s) and the parameterizations within that (those) envelope region(s). For a given TMD patient, certain movements and stops may be favored or avoided based on the particular TMD malady of that particular patient. Because the retentive pieces are placed on the dentate arches in the prescribed asymmetric orientation, the defined space (envelope region) may be very different as compared to the previous examples.

Understanding the customized movement profile as a mathematical object and the defined space (envelope region) available for manipulation, a continuum within this envelope of other parameterized synergistic shapes can be mathematically derived that will allow other patient considerations. As non-limiting examples of dentulous, partially edentulous and other solutions, FIGS. 38A and 38B illustrate two possible customized solutions within this continuum of synergistic, interacting shapes and contact areas that were derived from the customized guidance profile, which was in turn derived from an asymmetric guidance package. FIG. 38A illustrates front (3800*a*-1) and lateral views (3800*a*-2) of an asymmetric TMD treatment appliance in which the guidance is located on the posterior lateral or posterior facial aspects of the retentive pieces. Meanwhile, FIG. 38B illustrates front (3800*b*-1) and lateral views (3800B-2) views of an asymmetric TMD treatment appliance in which the guidance is located in the anterior area of the retentive pieces. As with the other examples, the shapes of the contact surfaces may not appear to be the same as those of the canonical asymmetric guidance package, but were chosen from within an envelope of possibilities mathematically derived from the customized asymmetric guidance package to feature that same movement and stop profile. In some cases, such as for a rare asymmetric restoration, an asymmetric restoration can include materials that mimic patient tissue in certain geometric shapes to contribute to the movement and stop profile (e.g., prosthetic teeth that feature inclinations and geometry of the teeth surfaces and angles and inclinations of the teeth cusps).

Figure 39A:
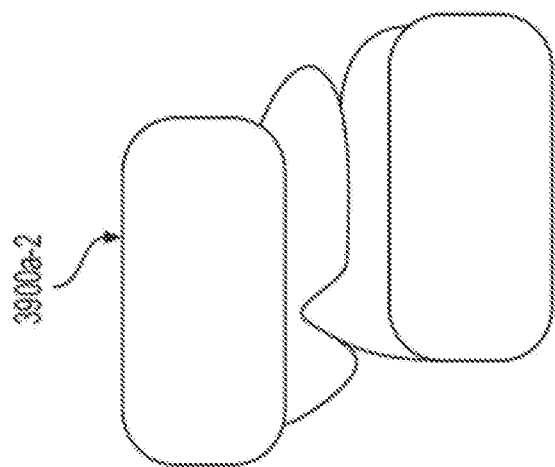
Figure 39A:
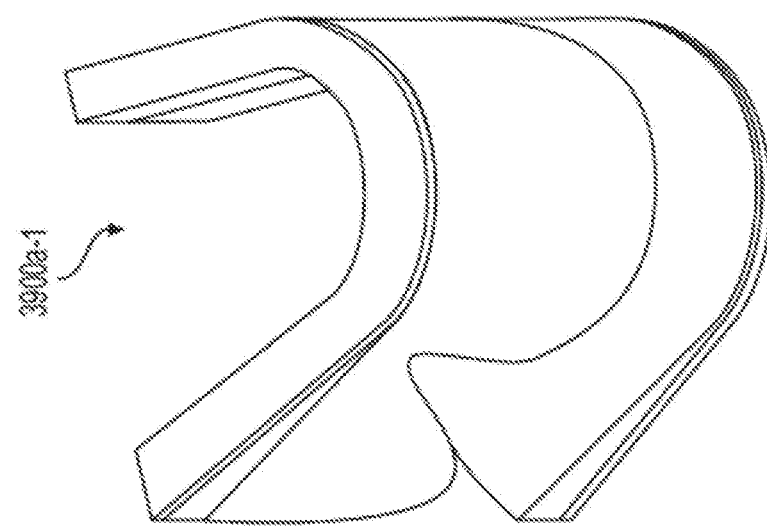
Figure 39B:
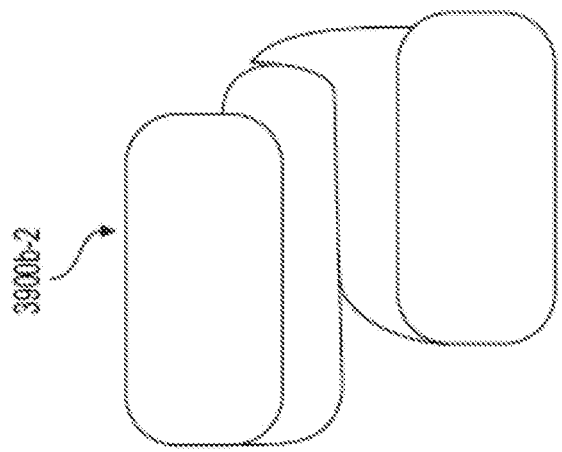
Figure 39B:
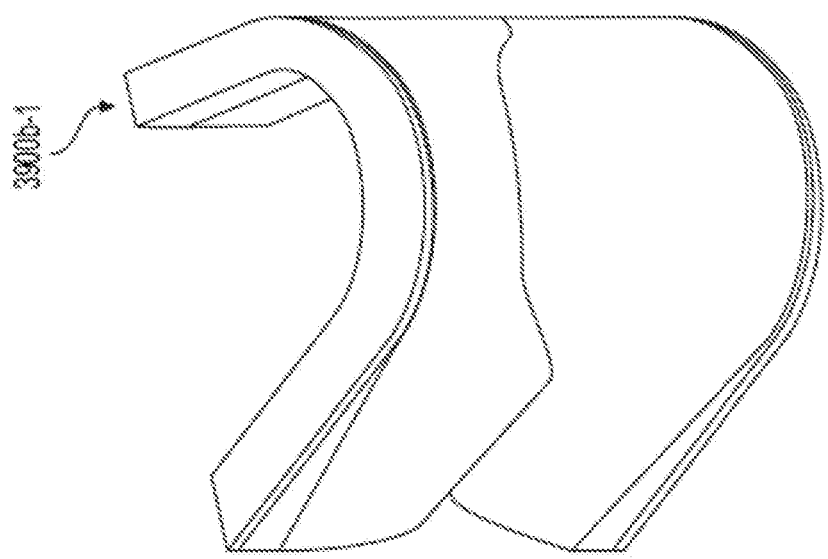

FIGS. 39A and 39B illustrate example final solutions where a bilateral anterior repositioning guidance package (e.g., 3430 of FIG. 34) in accordance with some embodiments of the present disclosure is applied, for example, using the method described with reference to FIGS. 32 and 33. Potential uses of a bilateral anterior repositioning guidance package (that may be a virtual representation and/or a mathematical object) in accordance with an example embodiment of the present disclosure include TMD appliances, other appliances, a series of step therapeutic appliances for rehabilitation (e.g., for displaced meniscus discs), sleep apnea appliances (e.g., by bringing the jaw forward in the index position), symmetrical protrusive arch reconstruction (which is likely to be a rare), restoration, rehabilitation, and/or optimization.

As an example, a clinician may plan a bilateral anterior repositioning two arch sleep apnea appliance. As non-limiting examples of dentulous, partially edentulous and other solutions, FIGS. 39A and 39B illustrate two possible customized solutions from within an envelope of synergistic, interacting shapes and contact areas that were derived from the customized guidance profile, which was in turn derived from a bilateral anterior repositioning guidance package. FIG. 39A illustrates front (3900*a*-1) and lateral views (3900*a*-2) of a symmetric protrusive sleep apnea appliance in which the guidance is located on the posterior lateral or posterior facial aspects of the retentive pieces. Meanwhile, FIG. 39B illustrates front (3900*b*-1) and lateral views (3900*b*-2) of a symmetrical protrusive sleep apnea appliance in which the guidance is located in the anterior area of the retentive pieces.

Another example of an appliance that could be derived from a bilateral anterior repositioning guidance package (3430 of FIG. 34) according to the present disclosure would be a bilateral anterior repositioning appliance to treat bilateral anterior disc displacement of both TMJs. In this case, the same protocol would be used except that the prescribed index position (maximum closure position) would be consistent with the patient arches in a position therapeutic to treat a bilateral anterior disc displacement of both TMJs in a patient, and the data for this particular patient could include specific TMD (TMJ dysfunction) data. This data could be collected through the use of clinical evaluation, 3D x-ray, a Jaw Motion Analyzer (e.g., as illustrated in FIG. 14), sonography, Mill, or other methods. This data could affect envelope region(s) and the parameterizations within that (those) envelope region(s). For a TMD patient there could be areas of both movement and stops that may be favored or avoided based on the particular TMD malady of that particular patient. This different appliance derived from a same canonical bilateral anterior repositioning guidance package illustrates the flexibility of the guidance package system to treat a wide variety of ailments and situations, often with the same guidance package.

Figure 40A:
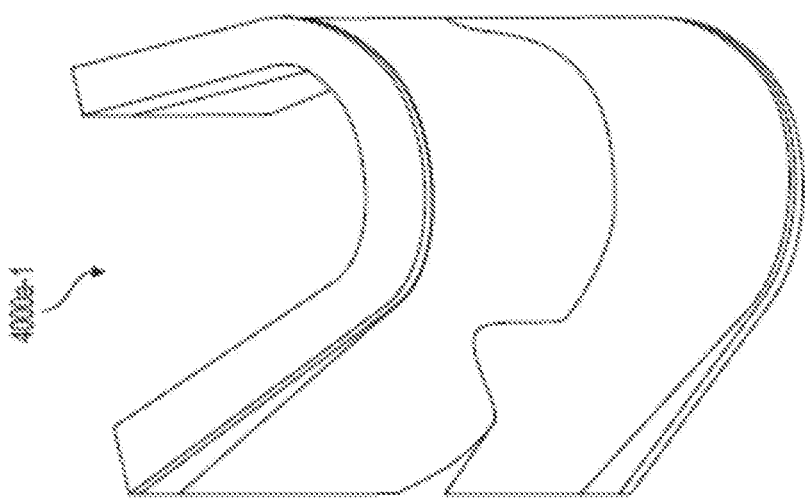
Figure 40B:
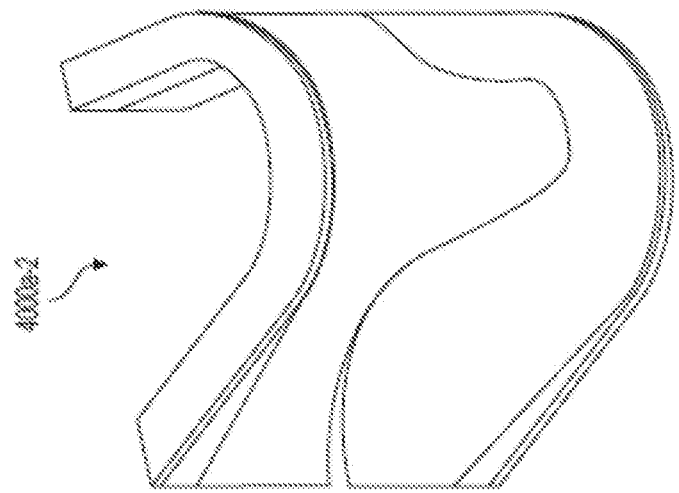

FIGS. 40A and 40B illustrate example final solutions where an asymmetric protrusive guidance package (3450 of FIG. 34) in accordance with some embodiments of the present disclosure is applied, for example, using the method described with reference to FIGS. 32 and 33. Potential uses of an asymmetric protrusive guidance package include TMD appliances, unilateral anterior repositioning appliances, other appliances, a series of step therapeutic appliances for rehabilitation, appliances for asymmetric protrusive arch reconstruction (rare), restoration, rehabilitation, and/or optimization. A canonical asymmetric protrusive guidance package is customized (sized, indexed, and adjusted), and attached (for example to retentive pieces), such that it is now customized for that patients' data and can be defined as a geometrical object.

Data for this particular patient could include specific TMD (TMJ dysfunction) data. As discussed above, this data could affect envelope region(s) and the parameterizations within that (those) envelope region(s).

As an example, a clinician may plan a two arch TMD appliance. As non-limiting examples of dentulous, partially edentulous and other solutions, FIGS. 40A and 40B illustrate two possible customized solutions from within this continuum of synergistic, interacting shapes and contact areas that were derived from the customized guidance profile, which was in turn derived from an asymmetric protrusive guidance package (3450 of FIG. 34). FIG. 40A illustrates a front view of an asymmetric protrusive appliance in which the majority of the guidance is located on the posterior lateral or posterior facial aspects of the retentive piece. Meanwhile, FIG. 40B illustrates a front view of an asymmetric protrusive appliance in which the majority of the guidance is located in the anterior area of the retentive pieces. As discussed above with reference to other examples, the specific shape may differ from the canonical guide, but will control a same movement and stop profile.

In many of the previous examples the guidance package system has been used to create two arches of guidance and stops working in synergy with each other to provide the appliances or restorations that provide the new movement profile to the new index position (prescribed maximum closure position). The guidance package systems can also provide the tools to produce one arch solutions to be combined with the patient's existing, unmodified opposing arch to provide the new movement profile to the new index position. After the continuum of shapes is determined, the one-arch solution to be created will be evaluated by the clinician such that when the created arch is combined with the patient's unmodified opposing arch the prescribed movement profile to the new index position (prescribed maximum closure position) is provided.

In some cases, retentive pieces are mounted virtually and then combined with the guidance and stop features. Then, after printing, the retentive pieces may be physically connected to the surface of the patient's tissue of that respective arch. In other embodiments, the retentive pieces or other guidance solutions are developed within a global envelope region defined by planar curves.

In some cases, a guidance package system according to the present disclosure (e.g., a CAD-CAM guidance package system) can provide the tools to consider existing tissue, not to be modified for a solution (e.g., use the naturally occurring guidance or stop features on the surface of teeth and other tissues to adjust an index position or guide path). In some embodiments, the guidance package system can also enable a clinician to consider existing tissue for manipulation/modification in consideration of a particular guidance package solution.

In some embodiments, the retentive pieces may be virtualized and placed into the tissue for consideration as part of the solution. An envelope region for parametrical calculation can be defined in many ways; in this example the retentive pieces and/or surfaces of retentive pieces may be virtualized for that purpose.

In some embodiments, a 3D region may be defined by virtual curves. These curves may or may not be associated with anatomical features, virtual retentive pieces, tissue, or many other considerations of how to include or portion 3D regions.

Figure 41:
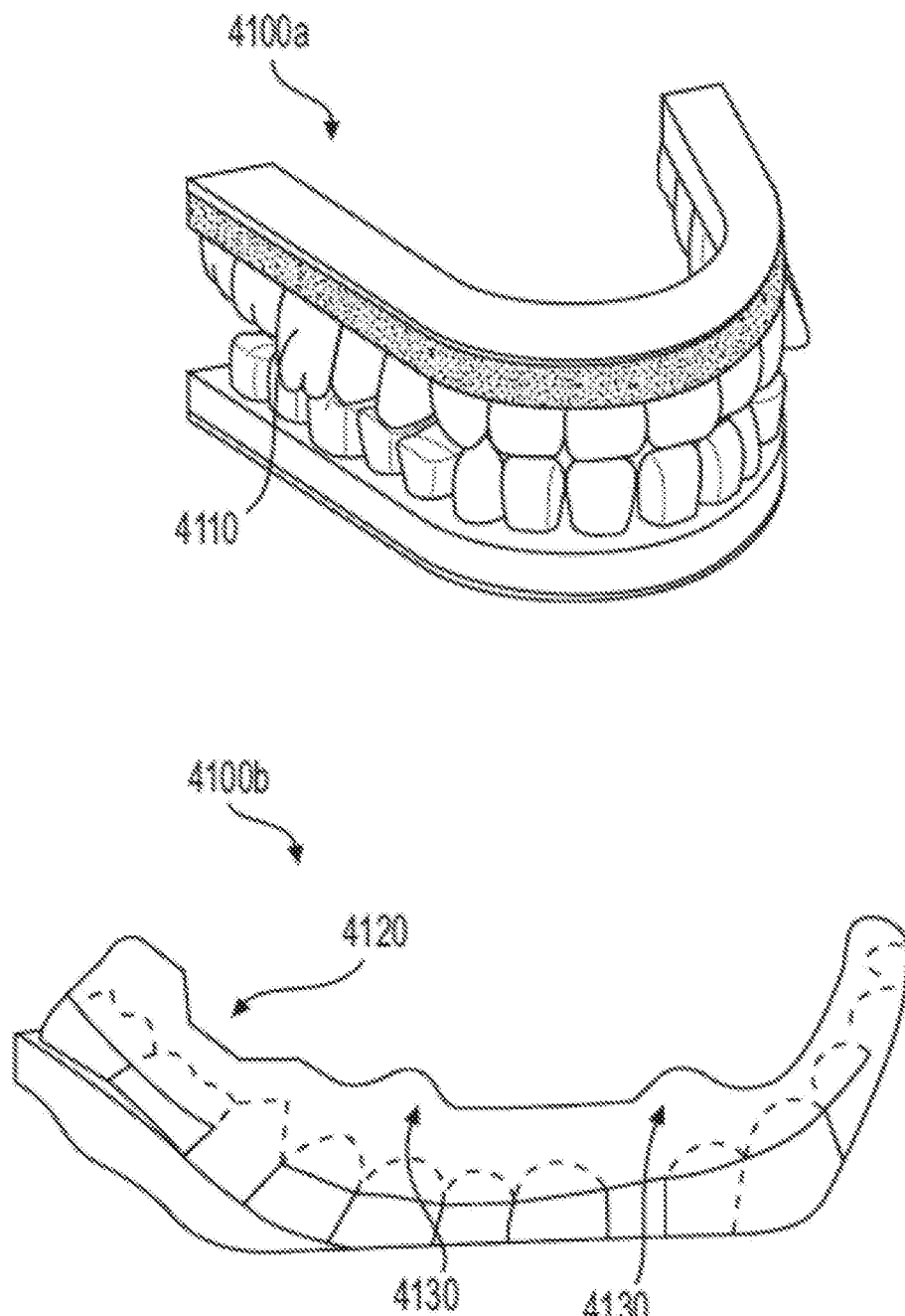

FIG. 41 illustrates an example final solution where a canine guidance package (3410 of FIG. 34) in accordance with some embodiments of the present disclosure is applied, for example, using the method described with reference to FIGS. 32 and 33. In FIG. 41, the final solution takes the form of a one-piece (one arch) appliance (e.g., bruxism appliance) on a dentate patient with a major interference in the maxillary arch using a canonical canine guidance package (3410 of FIG. 34) (that may be a virtual representation and/or a mathematical object), in accordance with an example embodiment of the present disclosure. In this example, a canonical canine guidance package is used to produce a one arch canine guidance appliance that interacts with this patient's unmodified maxillary arch to provide a canine guidance movement profile to the designated index position (e.g., prescribed maximum closure position). In this case, the boundaries of the envelope region would be the contact surfaces of one arch (e.g., a virtual curve positioned to expose a surface of the one arch) and an appliance disposed on the other arch (e.g., a virtual retentive piece whose inferior surface exhibits the region defining curve virtually positioned on the other arch). As seen in 4100-*a*, the patient has a major interference 4110 in the tooth #3 (according to the Universal Numbering System a/k/a the American System) area of the maxillary arch. Due to the major interference 4110, possibilities of acceptable opposing (one) arch appliances will likely come from within a narrow continuum. That is, any solution must provide canine guidance in the context of this unmodified maxillary arch that includes a major interference.

Once the canonical canine guidance package is customized and appropriately attached, this now customized for that patient movement profile can be defined as a geometrical object. As a non-limiting example, 4100-*b* is a one arch mandibular appliance selected from within a continuum of possibilities mathematically derived from the canine guidance package that feature the same movement and stop profile. In this example, the one arch appliance 4100-*b* features thin material on the mandibular retentive piece in the area (4120) opposing the maxillary arch interference (tooth #3) and strong canine guidance in the canine area (4130) of the mandibular retentive piece to guide over that major maxillary (#3) interference. The surface of the mandibular retentive piece is shaped to interact with the surface of the tissue of the maxillary arch (e.g., teeth). Although the shape of the mandibular retentive piece may differ from the customized canonical guidance package, but will feature the same movement and stop profile.

Figure 42:
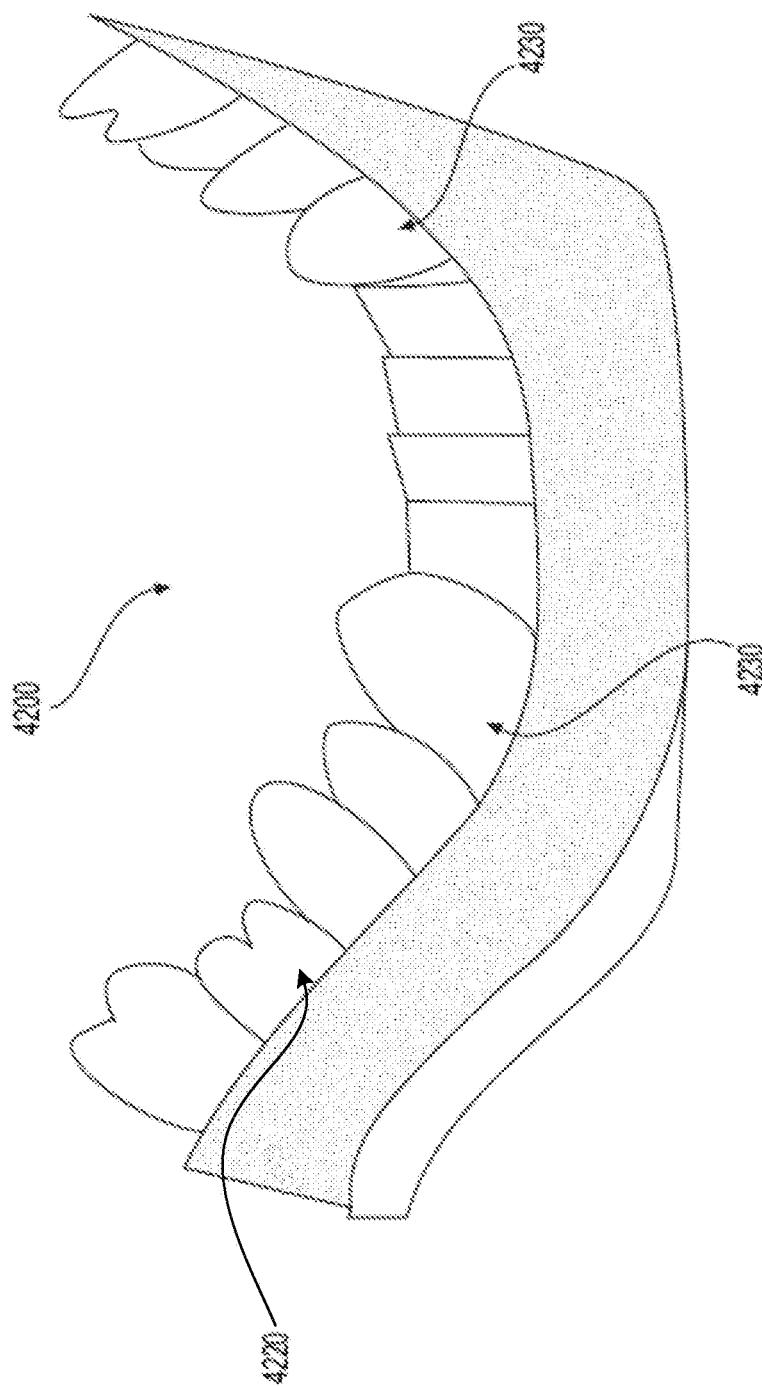

FIG. 42 illustrates another example final solution where a canine guidance package (3410 of FIG. 34) in accordance with some embodiments of the present disclosure is applied, for example, using the method described with reference to FIGS. 32 and 33. In FIG. 41, the final solution takes the form of a one-piece (one arch) restoration on a patient who is dentate on the maxillary arch with a major interference and an edentulous mandibular arch. This formation is similar to the example described above with reference to FIG. 41, except the patient's mandibular arch is edentulous and the final solution takes the form of a restoration.

Referring to FIG. 42, the final solution takes the form of a one arch mandibular restoration 4200. In this example, the printed restoration features very thin material (a very small prosthetic tooth (4220) on the mandibular restoration opposing the maxillary interference and strong canine guidance on the mandibular restoration in the form of prosthetic teeth at the correct angulations on the canine areas (4230) of the retentive piece to guide over that major maxillary (#3) interference. The inclinations and geometry of the prosthetic teeth, including the angles and inclinations of cusps and other features, may provide the guidance and stops via interaction with the unmodified maxillary arch.

In many of the examples above, the guidance package system according to some embodiments of the present disclosure have been used in the creation of two piece appliance systems, two piece restorative systems, one piece appliance systems, and one piece restorative systems that can guide a patients mandible by a prescribed 3D route (dependent upon the guidance package used) to a prescribed index position (e.g., prescribed maximum closure position). In some circumstances, however, it may be beneficial to adjust the shape and size of one or both arches of the patient, which may otherwise be incompatible with a desired guidance package solution. According to some embodiments of the present disclosure, the clinician in the surgical/restorative/reconstructive/optimizing work that may need to occur on an arch or arches of a patient to change the shape, size, volume, contact area topography and other aspects of an arch in the form that will be compatible with the desired guidance package solution. In certain circumstances, a patient's existing tissue may make the application of certain solutions either uncomfortable, or not reasonably feasible (for example, multiple excessively large interferences).

Accordingly, some embodiments of the present disclosure may provide tools for producing surgical or restorative guides (see, e.g., 35E-F). These guides can indicate areas to remove tissue or to add tissue. In some cases, it may be advantageous to utilize a conservative treatment plan to one arch (e.g., retentive piece) that enables minimal adjustments to the opposing arch. The envelope of parametrical possibilities enables a clinician to evaluate both arches simultaneous regarding shape and evaluate to find conservative two arch approaches. In some cases, the guidance package system may be configured to identify conservative approaches based on an amount of tissue added or removed, or a number of areas where tissue is to be added and removed. In some cases, a clinician may choose a guidance package derived restorative guide for a dentate arch that allows him conservative adjustment of the dentate arch to enable him to plan for the printed opposing arch he prefers in the context of the overall guidance package solution.

Figure 43A:
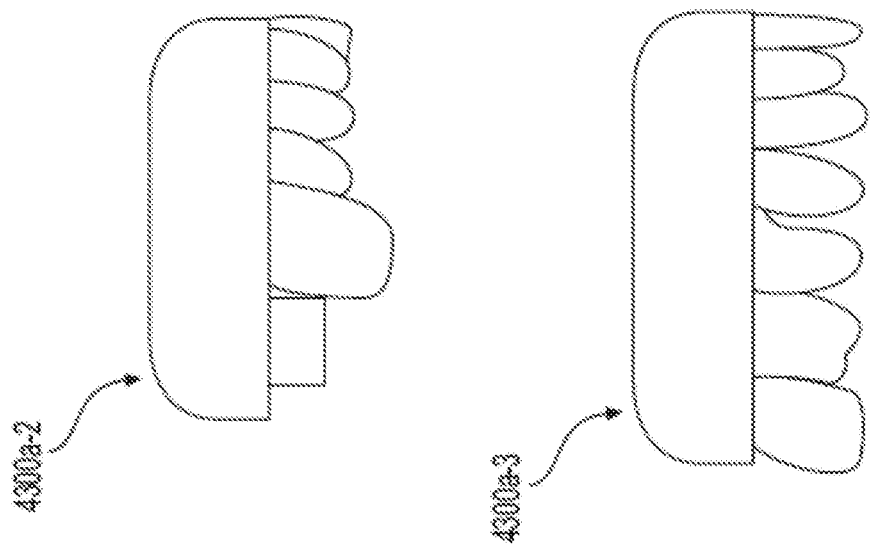
FIG. 43A illustrates an example maxillary arch before and after modification using a guidance package derived restorative guide according to an example embodiment.
Figure 43A:
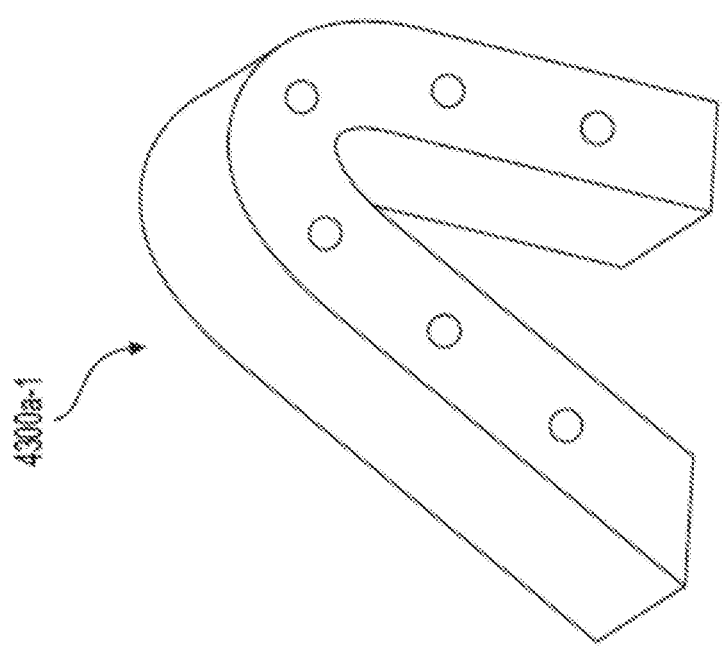
Figure 43B:
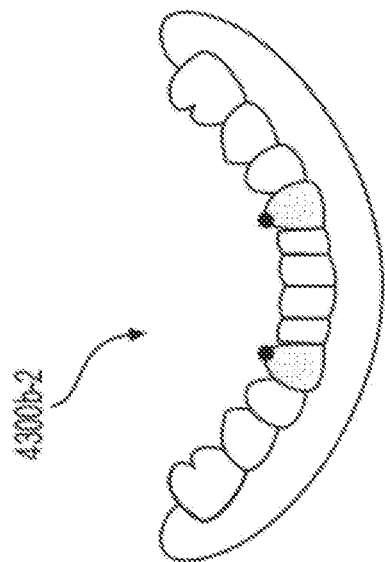
FIG. 43B illustrates two parametric restorative choices derived from a canonical canine guidance package that have corollary restorative guides to modify the opposing arch according to some example embodiments.
Figure 43B:
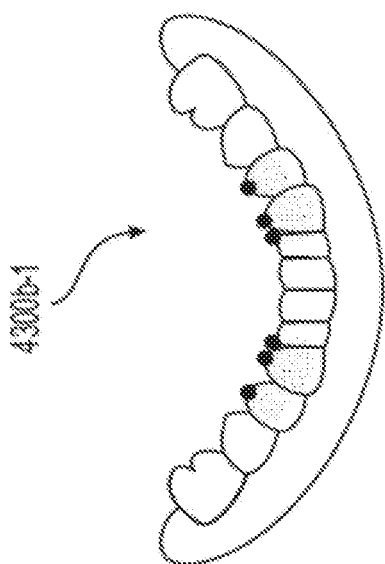

For example, FIGS. 43A and 43B illustrate final solutions taking the form of a two-arch modification and restorative solution on a patient who is dentate on the maxillary arch with a major interference opposing an edentulous mandibular arch using a canonical canine guidance package, in accordance with an example embodiment of the present disclosure. This situation may be identical to that described with reference to FIG. 42, except that the desired solution differs. Accordingly, the boundary for the envelope region will extend into the tissue of the maxillary arch. In some embodiments, this is accomplished by placing a virtual curve within the tissue of the maxillary arch. This patient has a major interference in the maxillary arch #3 tooth area as well as some minor interferences of the maxillary arch as defined by the two-arch canine guidance package solution the clinician has determined.

Referring to FIG. 43A, the canine guidance package derived restorative guide 4300a-1 may be used on the maxillary arch for reducing interferences (i.e., may guide a dentist, dental surgeon, or oral surgeon in reducing the interference or otherwise altering the tissue of the maxillary arch). 4300a-2 illustrates the maxillary arch before interference reduction and 4300a-3 illustrates the maxillary arch after interference reduction. The opposing mandibular produced arch (4300b-1 or 4300b-2) that will be applied to the patient's edentulous mandibular arch may be formed to interact with the maxillary arch as modified according to the restorative guide 4300a-1 in to provide the prescribed movement profile to the new prescribed index position (prescribed maximum closure position). As will be understood, the restorative guide 4300a-1 and the opposing mandibular arch (4300b-1 or 4300b-2) are just example solutions from a continuum of mathematically derived possibilities.

In some cases, a desired restorative guide 4300a-1 may first be selected, and then a compatible arch restoration (e.g., 4300b-1 or 4300b-2) may be selected from a continuum of mathematically derived possibilities. In some cases, a desired arch restoration (e.g., 4300b-1 or 4300b-2) may be selected and the compatible restorative guide 4300a-1 may be selected from a continuum of mathematically derived possibilities. In some cases, a single restorative guide 4300a-1 may be used to adjust the arch. In other cases, two or more restorative guides may be designed and printed to guide in two or more procedures. In the example discussed with reference to FIGS. 43A and 43B, parametric considerations (e.g., possible solutions) include surgical/restorative guides or stents for modifying the maxillary arch along with formed, printed, or CAM-produced opposing arch corollaries. A two arch restorative solution is determined from a continuum of shapes. In this example, the shape possibilities could include those that, when conservative changes are accomplished on the maxillary arch using guidance package derived surgical/restorative guides or templates, a certain range of printed opposing full arch mandibular restorative choices become available.

Figure 44A:
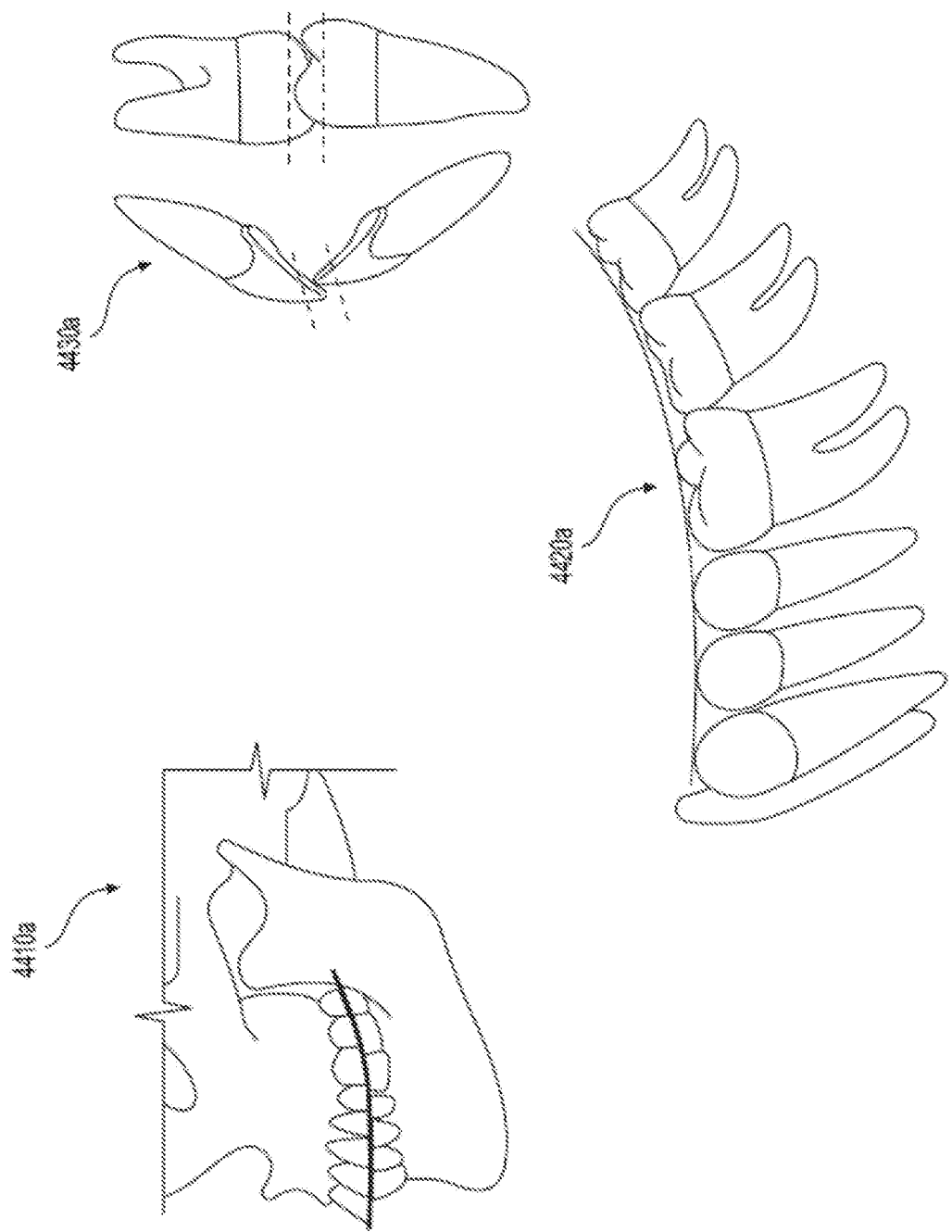
FIG. 44A illustrates the curve of Spee.
Figure 44C:
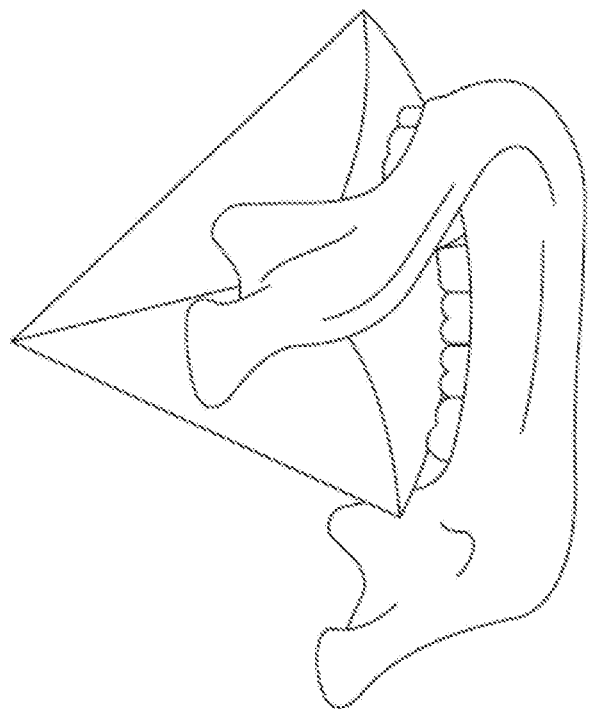
FIG. 44C illustrates the sphere of Monson.

In some cases, a clinician may determine that shape changes of the arch form of a patient may be needed because the patient's current arch architecture does not function well with the parameters of their particular TMJ set. It is understood by many dentists that the curves of occlusion, including the curve of Wilson FIG. 44B and the curve of Spee FIG. 44A, are important to the health and function of both the teeth and the TMJs. It is believed by many dentists that the mandibular teeth move over the surface of the maxillary teeth as over the surface of a sphere with an approximate diameter of eight inches, the sphere of Monson FIG. 44C. These curves allow the harmony of teeth and TMJs in function and in rest.

Regarding the curve of Spee FIG. 44A, it is the anatomic curve established by the occlusal alignment of the teeth or arch as projected onto the median plane from the tip of the mandibular canine to the mandibular condyle (4410A and 4420A). It is believed by many dentists that the anterior/posterior tilting of teeth (4430A and 4420A) enabled by the curve of Spee is appropriate to keep the individual teeth at right angles to the forces of occlusion. Some dentists regard the curve of Spee as an extension of the arc of closure. As an example, the curve of Spee combined with inclination of the canine surfaces (canine teeth) provides the guidance that provides for the appropriate disclusion of the posterior teeth in a protrusive excursion of the mandible.

Figure 44B:
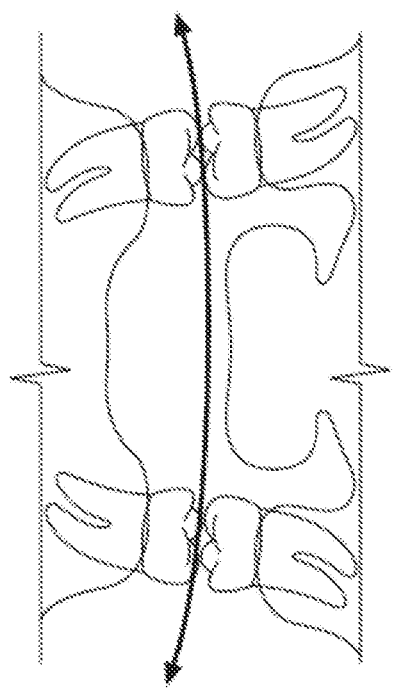
FIG. 44B illustrates the curve of Wilson.

Regarding the curve of Wilson FIG. 44B, it is the mediolateral curvature of the occlusal plane of the posterior teeth. Many dentists believe the purpose of the arc or curve is to complement the paths of condyles during movements of the mandible. It is further understood that the increased heights of the mandibular buccal cusps (due to their angulations provided by the curve of Wilson) and the complementary form of the upper posterior teeth (due to their angulations due to the curve of Wilson) cusps allow the food to remain in the chewing area and not spill out laterally.

Additional or alternative functions of the curves of occlusion in addition to those listed above may include force accepting structure of the arch form (the curves of occlusion) that may be manipulated using one or more embodiments of the present disclosure. The shape of the final restored arch using the guidance package system can produce prosthetic teeth and individual cusps of those prosthetic teeth inclined in the image of the curves of Wilson and Spee (when combined is the sphere of Monson) (FIGS. 44A-44C), in a shape that brings harmony with the TMJs (or other therapeutic goal).

The guidance package system can distribute guidance and stops strategically over any of the available surface area or a subset of available surfaces to accommodate all the curves of occlusion (the "teeth" are in many ways the final extension of these curves). While the teeth themselves have a certain shape, their inclination is also important for guidance and accommodation of the curves of occlusion. The curves of occlusion or the "shape" of the arch is important. It is not just the features of the teeth, but the inclination of those teeth in regard to each other. In certain embodiments, the guidance package system can provide both the overall 3D shape of the arch form, and the final guidance and stop features (teeth) blended together. This is one advantage of certain embodiments, as the related art does not allow parametric considerations of that patient's particular TMJ set.

Figure 45B:
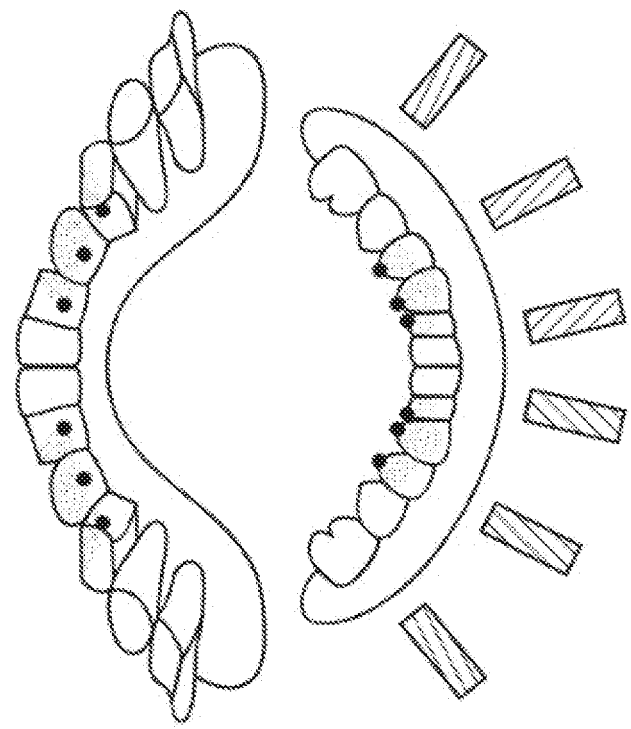
FIGS. 45A-45D illustrate development, selection, and implementation of a guidance solution according to an example embodiment.
Figure 45A:
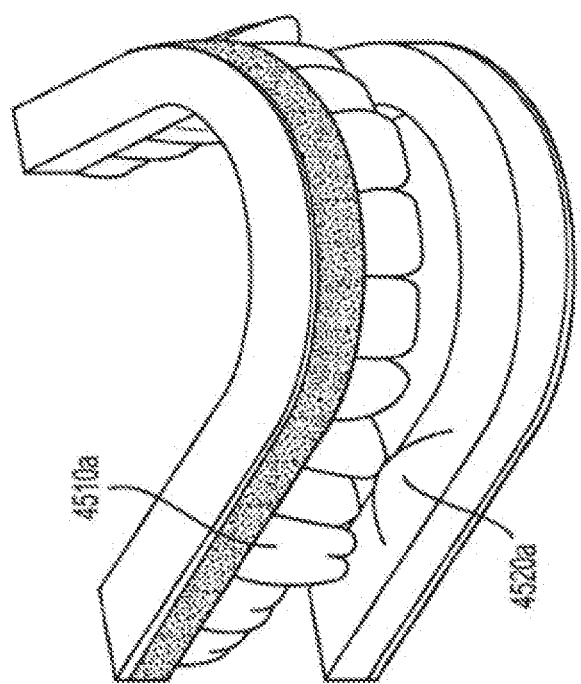
Figure 45D:
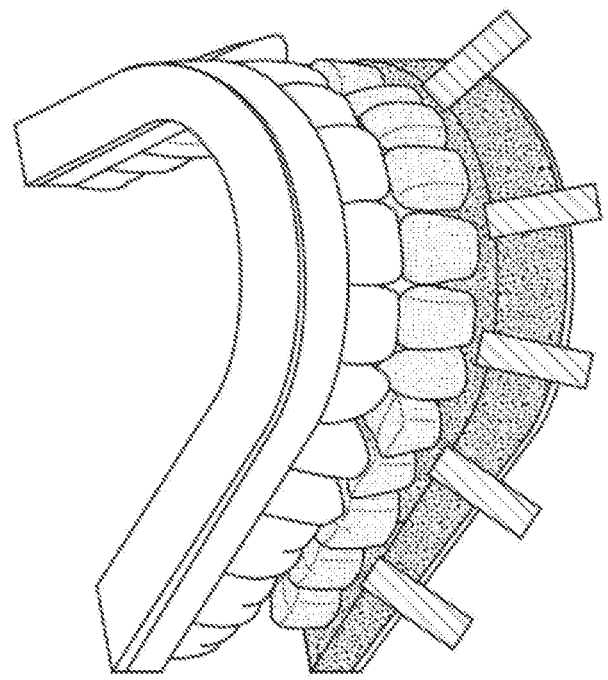
Figure 45C:
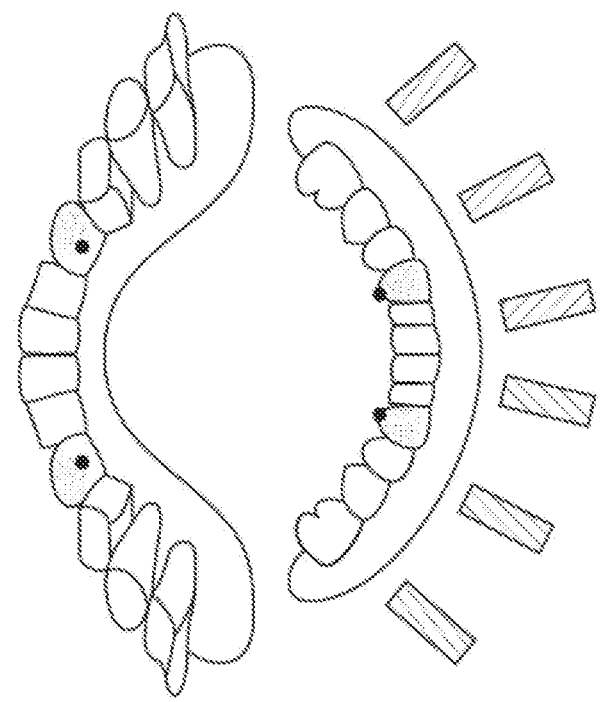

FIGS. 45A-45C will be referred to in developing solutions of a two-arch modification and restorative solution on a patient who is dentate on the maxillary arch with a major interference opposing an edentulous mandibular arch with an inappropriate tissue mass using a canonical canine guidance package (e.g., 3410 of FIG. 34) is applied, for example, using the method described with reference to FIGS. 32 and 33. In this example the patient has a dentate maxillary arch incompatible 4510A (e.g., a major interference similar to that discussed above with reference to FIG. 41) with the two-arch solution desired. The patient's mandibular arch is edentulous and has a tissue mass 4520A that is incompatible with the two-arch solution desired. This patient's TMJ values are considered in the solution to provide appropriate curves of occlusion (FIGS. 43A-43C) to optimize occlusal/TMJ synergy. In the present example, the boundary of the envelope region will be defined to include tissue of the mandibular arch and the maxillary arch, for example, by placing virtual curves beneath the surface of some portion of the maxillary and mandibular arches.

In some circumstances, the two-arch modification may modify the maxillary arch using a guidance package derived restorative guide. In some circumstances, the two-arch modification may modify an edentulous mandibular arch by removing the inappropriate tissue mass using a surgical guide.

In some implementations, implants may be placed into the surgically modified mandibular arch at appropriate angulations based on the curves of occlusion, provided by the guidance package system in the form of restorative and surgical guides, using a guidance package derived implant placement guide FIG. 35G. Using a guidance package derived implant placement guide will enable an operator to place implants at angulations appropriate to the curvatures and force vectors of the guidance package solution.

Referring to FIGS. 45A-45C, once the boundaries of the envelope region are defined and the guidance package is attached (and/or customized), one or more restorative guides may be generated for the maxillary arch, and one or more surgical guides may be generated for the mandibular arch to address the incompatible tissue. In addition, a mandibular implant placement guide and mandibular restoration (e.g., false teeth) may be designed to interact with the tissue (e.g. teeth) of the maxillary arch to provide the customized movement profile. FIGS. 45B and 45C illustrate two possible solutions. In some embodiments the two arch solution may be determined not only based on an envelope region and guidance and stop profile, but also to include the appropriate curves of occlusion for a particular patient based on TMJ data (FIGS. 45B and 45C).

In some cases, the parameterization of a movement profile may enable generation of surgical and/or restorative guides to change an arch form based on TMJ values (e.g., change to an ideal or near-ideal arch form based on the TMJ value consistent with the curves of occlusion).

Movement and stop profile and parameterizations are a continuum of virtual (and mathematical) morphing shapes of the maxillary arch and the mandibular arch in synergy with each other. This continuum of possibilities within the envelope region provides different areas of contact and guidance that may interact differently with the stomatognathic system but will allow an operator to maintain the determined movement and stop profile. Ultimately in this example the dentate maxillary arch will be modified using restorative guide(s) (to address the interference 4510A), the edentulous mandibular arch will be modified with surgical guide(s) (to address the tissue 4520A) and an implant placement guide (to provide a base for a restoration and to accommodate the curves of occlusion), and the mandibular arch will be restored with a printed mandibular arch restoration (for interacting with the tissue of the modified maxillary arch). The final result will feature the manipulated maxillary dentate arch (and perhaps #3 restored using a crown as a subset of the overall guidance package solution) and a surgically manipulated mandible with implants appropriately placed to attach to the retentive piece of the printed mandibular restoration (FIG. 45D). This comprehensive modification/restoration will feature the appropriate curves of occlusion (Spee and Wilson) and guidance and stop profile determined by the clinician considering this particular patients' therapeutic situation to include that patients' particular TMJ values.

Referring to FIGS. 45A-45D, the final product will feature a guidance package derived modified maxillary arch, a surgically modified mandibular arch, implants placed in the mandibular arch using a guidance package derived implant placement guide, and a printed mandibular restoration to be mounted on the previously placed implants. This guidance package derived modification/restorative solution will provide the same guidance and stop profile as the customized guidance package, and may also provide the appropriate curves of occlusion for this particular patient based on his TMJ data.

It is to be understood that the embodiments and claims disclosed herein are not limited in their application to the details of construction and arrangement of the components set forth in the description and illustrated in the drawings. Rather, the description and the drawings provide examples of the embodiments envisioned. The embodiments and claims disclosed herein are further capable of other embodiments and of being practiced and carried out in various ways. Also, it is to be understood that the phraseology and terminology employed herein are for the purposes of description and should not be regarded as limiting the claims.

Accordingly, those skilled in the art will appreciate that the conception upon which the application and claims are based may be readily utilized as a basis for the design of other structures, methods, and systems for carrying out the several purposes of the embodiments and claims presented in this application. It is important, therefore, that the claims be regarded as including such equivalent constructions.

Furthermore, the purpose of the foregoing Abstract is to enable the United States Patent and Trademark Office and the public generally, and especially including the practitioners in the art who are not familiar with patent and legal terms or phraseology, to determine quickly from a cursory inspection the nature and essence of the technical disclosure of the application. The Abstract is neither intended to define the claims of the application, nor is it intended to be limiting to the scope of the claims in any way.

It should also be noted that, as used in the specification and the appended claims, the singular forms "a, an" and "the" include plural references unless the context clearly dictates otherwise. References to a composition containing "a" constituent is intended to include other constituents in addition to the one named. Also, in describing the preferred embodiments, terminology will be resorted to for the sake of clarity. It is intended that each term contemplates its broadest meaning as understood by those skilled in the art and includes all technical equivalents which operate in a similar manner to accomplish a similar purpose.

Herein, the use of terms such as "having," "has, including," or "includes" are open ended and are intended to have the same meaning as terms such as "including" or "includes" and not preclude the presence of other structure, material, or acts. Similarly, though the use of terms such as "can" or "may" is intended to be open-ended and to reflect that structure, material, or acts are not necessary, the failure to use such terms is not intended to reflect that structure, material, or acts are essential. To the extent that structure, material, or acts are presently considered to be essential, they are identified as such.

Further, used herein the terms "dentist," "dental professional," operator, clinician, ', and the like shall be interchangeable to refer to a person providing dental care or medical care or treating using the disclosed systems, methods, or devices.

It is also to be understood that the mention of one or more method steps does not preclude the presence of additional method steps or intervening method steps between those steps expressly identified. Moreover, although the term "step" may be used herein to connote different aspects of methods employed, the term should not be interpreted as implying any particular order among or between various steps herein disclosed unless and except when the order of individual steps is explicitly required. The components described herein as making up various elements of one or more example embodiments are intended to be illustrative and not restrictive. Many suitable components that would perform the same or similar functions as the components described herein are intended to be embraced within the scope of the invention. Such other components not described herein can include, but are not limited to, for example, similar components that are developed after development of the presently disclosed subject matter.

What is claimed is:

1. A method of producing a guidance-equipped solution configured to provide a desired movement profile for mandibular and maxillary arches of a recipient relative to each other, the method comprising:
    obtaining data descriptive of the mandibular and maxillary arches, an index position of the mandibular arch with respect to the maxillary arch, and one or more boundaries of a three-dimensional region, and boundaries of a three-dimensional region, wherein a boundary of the three-dimensional region comprises a region embedded within surfaces of at least one of the mandibular arch and the maxillary arch;
    specifying a virtual guidance package based on the desired movement profile, the virtual guidance package associated with a movement profile;
    positioning the specified virtual guidance package in virtual space;
    parameterizing the specified guidance package, once positioned, to create one or more virtual guidance equipped solutions, each of the one or more virtual guidance equipped solutions being configured to provide the movement profile of the specified virtual guidance package, and wherein the one or more virtual guidance equipped solutions comprise a series of virtual guidance equipped solutions designed to progressively correct damage of the recipient; and
    generating data that can be used to create at least one physical guidance-equipped solution based on a virtual guidance equipped solution of the one or more virtual guidance equipped solutions configured to provide the movement profile associated with the specified virtual guidance package for the mandibular and maxillary arches relative to each other.

2. The method of claim 1, wherein the at least one of the one or more virtual guidance equipped solutions incorporates portions of the region embedded within the surfaces of at least one of the mandibular arch and the maxillary arch.

3. The method of claim 1 further comprising generating a virtual model of the maxillary and mandibular arches,
    wherein the specified virtual guidance package is positioned in virtual space within the virtual model.

4. The method of claim 1 further comprising customizing the specified virtual guidance package by adjusting at least one of a size, position, and orientation of the specified virtual guidance package within the virtual space, creating a customized movement profile,
    wherein the at least one physical guidance-equipped solution is configured to provide the customized movement profile for the mandibular and maxillary arches relative to each other.

5. The method of to claim 1, wherein the boundary of the three-dimensional region comprises tissue surfaces of at least one of the mandibular arch and the maxillary arch.

6. The method of claim 1, wherein the one or more virtual guidance equipped solutions comprise a plurality of synergistically shaped guidance solutions each configured to provide the movement profile associated with the specified virtual guidance package.

7. The method of claim 1, wherein the one or more virtual guidance equipped solutions comprises at least one of a surgical guide, a restorative guide, and an implant placement guide for at least one of the mandibular arch and the maxillary arch.

8. The method according to claim 7, wherein the boundary of the three-dimensional region defines a maximum possible depth of the surgical guide, restorative guide, and implant placement guide.

9. The method according to claim 1, wherein the at least one physical guidance-equipped solution comprises a therapeutic device.

10. The method of claim 1 further comprising selecting a virtual guidance equipped solution from the one or more virtual guidance equipped solutions based on a desired response from a neuromuscular system of the recipient.

11. The method of claim 1 further comprising selecting a virtual guidance equipped solution from the one or more virtual guidance equipped solutions based on curves of occlusion for the recipient.

12. The method of claim 1, wherein the one or more virtual guidance equipped solutions comprise a retentive piece for one of the mandibular and maxillary arches comprising surfaces configured to interact with tissue of the other one of the mandibular and maxillary arches to provide the movement profile associated with the specified virtual guidance package for the mandibular and maxillary arches relative to each other.

13. The method of claim 1 further comprising generating the data descriptive of the one or more boundaries of the three-dimensional region based on the data descriptive of the mandibular and maxillary arches.

14. The method of claim 1 further comprising identifying a desired form of the one or more virtual guidance equipped solutions,
    wherein the created one or more virtual guidance equipped solutions conform to the desired form.

15. The method of claim 1 further comprising generating the data descriptive of the one or more boundaries of the three-dimensional region based on the data descriptive of the mandibular and maxillary arches and the desired form of the one or more virtual guidance equipped solutions.

16. A non-transitory computer readable apparatus having stored thereon computer program code for performing a method of producing a guidance-equipped solution configured to provide a desired movement profile for mandibular and maxillary arches of a recipient relative to each other, the method comprising:

obtaining data descriptive of the mandibular and maxillary arches, an index position of the mandibular arch with respect to the maxillary arch, and one or more boundaries of a three-dimensional region, and boundaries of a three-dimensional region, wherein a boundary of the three-dimensional region comprises a region embedded within surfaces of at least one of the mandibular arch and the maxillary arch;

specifying a virtual guidance package based on the desired movement profile, the virtual guidance package associated with a movement profile;

positioning the specified virtual guidance package in virtual space;

parameterizing the specified guidance package, once positioned, across the three-dimensional region to create one or more virtual guidance equipped solutions, each of the one or more virtual guidance equipped solutions being configured to provide the movement profile of the specified virtual guidance package, wherein the one or more virtual guidance equipped solutions comprise a plurality of synergistically shaped guidance solutions each configured to provide the movement profile associated with the specified virtual guidance package; and generating data that can be used to create at least one physical guidance-equipped solution based on a virtual guidance equipped solution of the one or more virtual guidance equipped solutions configured to provide the movement profile associated with the specified virtual guidance package for the mandibular and maxillary arches relative to each other.

17. The non-transitory computer readable apparatus of claim 16, wherein at least one of the one or more virtual guidance equipped solutions incorporates portions of the region embedded within the surfaces of at least one of the mandibular arch and the maxillary arch.

18. The non-transitory computer readable apparatus of claim 16, wherein the method further comprises generating a virtual model of the maxillary and mandibular arches, and wherein the specified virtual guidance package is positioned in virtual space within the virtual model.

19. A method of producing a retention piece having a guidance package configured to provide a desired movement profile for mandibular and maxillary arches of a recipient relative to each other, the method comprising:

obtaining data descriptive of the mandibular and maxillary arches, an index position of the mandibular arch with respect to the maxillary arch at a predetermined maximum closure position, and at least one temporomandibular joint of the recipient;

specifying a guidance package based on the desired movement profile for the mandibular and maxillary arches relative to each other;

scaling the specified guidance package, based on at least a part of the obtained data;

positioning a virtual representation of a retention piece comprising the scaled specified guidance package about virtual representations of at least one of the mandibular and maxillary arches within a virtual articulator;

modeling, with the virtual representation of the retention piece positioned about the at least one of the mandibular and maxillary arches, relative movement of the virtual representations of the mandibular and maxillary arches within the virtual articulator to determine whether the specified guidance package provides the desired movement profile, the relative movement resulting from the guidance provided by the virtual representation of the specified guidance package;

generating data that can be used by a computer aided machining (CAM) process to create at least one physical retention piece comprising the specified guidance package configured to provide the desired movement profile; and instructing a three-dimensional printer to create the at least one physical retention piece based on the generated data, wherein the specified guidance package is specified from a plurality of guidance packages, each preprogrammed to provide a different movement profile, and wherein the at least one physical retention piece is configured to be embedded within surfaces of at least one of the mandibular arch and the maxillary arch and to provide the desired movement profile based on interference with at least a portion of tissue in a mouth of the recipient.

* * * * *